(12) United States Patent
Rothenberg et al.

(10) Patent No.: US 9,803,244 B2
(45) Date of Patent: Oct. 31, 2017

(54) METHODS OF DETERMINING EOSINOPHILIC GASTRITIS STATUS BASED ON MARKER OR GENE EXPRESSION

(71) Applicant: CHILDREN'S HOSPITAL MEDICAL CENTER, Cincinnati, OH (US)

(72) Inventors: Marc E. Rothenberg, Cincinnati, OH (US); Julie Caldwell, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/096,358

(22) Filed: Apr. 12, 2016

(65) Prior Publication Data
US 2016/0312282 A1  Oct. 27, 2016

Related U.S. Application Data

(63) Continuation of application No. 14/128,887, filed as application No. PCT/US2012/044061 on Jun. 25, 2012, now Pat. No. 9,345,763.

(60) Provisional application No. 61/500,508, filed on Jun. 23, 2011.

(51) Int. Cl.
| | |
|---|---|
| *C12Q 1/68* | (2006.01) |
| *A61K 31/7088* | (2006.01) |
| *A61K 31/713* | (2006.01) |
| *A61K 39/395* | (2006.01) |
| *A61K 48/00* | (2006.01) |
| *C07K 16/18* | (2006.01) |
| *C12N 15/11* | (2006.01) |
| *C12N 15/113* | (2010.01) |
| *G01N 33/68* | (2006.01) |

(52) U.S. Cl.
CPC ........ *C12Q 1/6883* (2013.01); *A61K 31/7088* (2013.01); *A61K 31/713* (2013.01); *A61K 39/395* (2013.01); *A61K 48/00* (2013.01); *C07K 16/18* (2013.01); *C12N 15/11* (2013.01); *C12N 15/113* (2013.01); *C12Q 1/6881* (2013.01); *G01N 33/6893* (2013.01); *C07K 2319/30* (2013.01); *C12N 2310/11* (2013.01); *C12N 2310/141* (2013.01); *C12N 2310/531* (2013.01); *C12Q 2600/118* (2013.01); *C12Q 2600/158* (2013.01); *C12Q 2600/16* (2013.01); *G01N 2800/06* (2013.01); *G01N 2800/52* (2013.01)

(58) Field of Classification Search
CPC ............... C12Q 1/6881; C12Q 1/6883; C12Q 2600/118; C12Q 2600/158; C12Q 2600/16; A61K 48/00; A61K 39/395; A61K 31/7088; A61K 31/713; G01N 33/6893; G01N 2800/52; G01N 2800/06; C07K 2319/30; C07K 16/18; C12N 2310/11; C12N 2310/141; C12N 2310/531; C12N 15/11; C12N 15/113
See application file for complete search history.

(56) References Cited

U.S. PATENT DOCUMENTS

| | | | |
|---|---|---|---|
| 4,522,811 | A | 6/1985 | Eppstein et al. |
| 5,530,101 | A | 6/1996 | Queen et al. |
| 5,888,510 | A | 3/1999 | Kishimoto et al. |
| 6,403,782 | B1 | 6/2002 | Luster et al. |
| 6,780,973 | B1 | 8/2004 | Luster et al. |
| 7,879,547 | B2 | 2/2011 | Rothenberg et al. |
| 8,030,003 | B2 | 10/2011 | Rothenberg |
| 8,409,565 | B2 | 4/2013 | Levi-Schaffer et al. |
| 9,260,756 | B2 | 2/2016 | Rothenberg et al. |
| 9,345,763 | B2 | 5/2016 | Rothenberg et al. |
| 9,517,238 | B2 | 12/2016 | Rochman et al. |
| 2003/0157479 | A1 | 8/2003 | Bachmann et al. |
| 2003/0194404 | A1 | 10/2003 | Greenfeder et al. |
| 2004/0141951 | A1 | 7/2004 | Rothenberg et al. |
| 2008/0187908 | A1 | 8/2008 | Adra |
| 2009/0233275 | A1 | 9/2009 | Rothenberg |
| 2009/0269774 | A1 | 10/2009 | Rothenberg et al. |
| 2011/0123530 | A1 | 5/2011 | Arron et al. |
| 2011/0195500 | A1 | 8/2011 | Rothenberg |
| 2011/0301046 | A1 | 12/2011 | Rothenberg et al. |
| 2012/0004205 | A1 | 1/2012 | Rothenberg |
| 2013/0324435 | A1 | 12/2013 | Rothenberg et al. |
| 2014/0228315 | A1 | 8/2014 | Rothenberg et al. |

FOREIGN PATENT DOCUMENTS

| | | |
|---|---|---|
| CN | 101275941 A | 10/2008 |
| EP | 0 949 271 A1 | 10/1999 |
| WO | WO-2005/106492 A2 | 11/2005 |
| WO | WO-2005/106492 A3 | 11/2005 |
| WO | WO-2006/119343 A1 | 11/2006 |
| WO | WO-2012/094643 A2 | 7/2012 |
| WO | WO-2012/094643 A3 | 7/2012 |

(Continued)

OTHER PUBLICATIONS

Collins MH, et al. Clin Gastroenterol Hepatol. 6(6):621-629. Jun. 2008. Available online at—doi:10.1016/j.cgh.2008.01.004.*

(Continued)

*Primary Examiner* — Robert Landsman

(74) *Attorney, Agent, or Firm* — Mintz Levin Cohn Ferris Glovsky and Popeo, P.C.; Muriel Liberto, Esq.

(57) ABSTRACT

The disclosure provides compositions and methods related to the diagnosis, prognosis, and treatment of inflammatory diseases and disorders, especially allergic inflammatory diseases and disorders.

12 Claims, 37 Drawing Sheets

(56) References Cited

FOREIGN PATENT DOCUMENTS

| WO | WO-2012/174549 A2 | 12/2012 |
|---|---|---|
| WO | WO-2012/174549 A9 | 12/2012 |
| WO | WO-2012/177945 A2 | 12/2012 |
| WO | WO-2012/177945 A3 | 12/2012 |
| WO | WO-2013/126834 A1 | 8/2013 |

OTHER PUBLICATIONS

April et al., "Whole-genome gene expression profiling of formalin-fixed, paraffin-embedded tissue samples," PloS One, Dec. 3, 2009, pp. e8162, vol. 4(12).

Berkman, et al. (Jun. 2001). "Eotaxin-3 but not eotaxin gene expression is upregulated in asthmatics 24 hours after allergen challenge," Am. J. Respir. Cell Mol. Biol. 24(6):682-687.

Blanchard C. et al. (Aug. 2005). "Inhibition of human interleukin-13-induced respiratory and oesophageal inflammation by anti-human-interleukin-13 antibody (CAT-354)," Clinical and Experimental Allergy 35(8): 1096-1103.

Blanchard et al., "Eosinophilic esophagitis: pathogenesis, genetics, and therapy," J. Allergy Clin. Immunol., Nov. 2006, pp. 1054-1059, vol. 118(5).

Blanchard et al., "Eotaxin-3 and a uniquely conserved gene-expression profile in eosinophilic esophagitis," J. Clin. Invest., Feb. 2006, pp. 536-547, vol. 116(2).

Blanchard et al., "IL-13 involvement in eosinophilic esophagitis: transcriptome analysis and reversibility with glucocorticoids," J. Allergy Clin. Immunol., Dec. 2007, pp. 1292-1300, vol. 120(6).

Blanchard et al., "Coordinate interaction between IL-13 and epithelial differentiation cluster genes in eosinophilic esophagitis," J. Immunol., Apr. 1, 2010, pp. 4033-4041, vol. 184(7).

Boeuf et al., "CyProQuant-PCR: a real time RT-PCR technique for profiling human cytokines, based on external RNA standards, readily automatable for clinical use," BMC Immunol., Mar. 4, 2005, p. 5, vol. 6.

Bullens et al., "IL-17 mRNA in sputum of asthmatic patients: linking T cell driven inflammation and granulocytic influx?," Respir. Res., Nov. 3, 2006, p. 135, vol. 7.

Caldwell et al., "Global Gene Expression Profile Analysis in Eosinophilic Gastritis Identifies CDH26," J. Allergy Clin. Immunol., Feb. 2011, pp. AB216, vol. 127(2).

Carriere et al., "IL-33, the IL-1-like cytokine ligand for ST2 receptor, is a chromatin-associated nuclear factor in vivo," Proc. Natl. Acad. Sci. U.S.A., Jan. 2, 2007, pp. 282-287, vol. 104(1).

Ehlers et al., "Differentiation of T cell lymphokine gene expression: the in vitro acquisition of T cell memory," J. Exp. Med. 1991, pp. 25-36, vol. 173(1).

Faubion, W.A. Jr. et al. (Jul. 1998). "Treatment of eosinophilic esophagitis with inhaled corticosteroids," Journal of Pediatric Gastroenterology and Nutrition 27(1):90-93.

Flower, "Modelling G-protein-coupled receptors for drug design," Biochim. Biophys. Acta., Nov. 16, 1999, pp. 207-234, vol. 1422(3).

Furuta et al., "Eosinophilic esophagitis in children and adults: a systematic review and consensus recommendations for diagnosis and treatment," Gastroenterology, Oct. 2007, pp. 1342-1363, vol. 133(4).

Garrett, J.K. et al. (Jan. 2004, e-published Dec. 12, 2003). "Anti-interleukin-5 (mepolizumab) therapy for hypereosinophilic syndromes." Journal of Allergy and Clinical Immunology, 113(1):115-119.

Hogan, S.P. et al. (Dec. 2004). "Review article: Theeosinophil as a therapeutic target in gastrointestinal disease," Alimentary Pharmacology and Therapeutics 20(11-12):1231-1240.

Huang et al., "RegRNA: an integrated web server for identifying regulatory RNA motifs and elements," Nucleic Acids Res., Jul. 1, 2006, W429-W434, vol. 34.

Hwang et al., "Expression of IL-17 homologs and their receptors in the synovial cells of rheumatoid arthritis patients," Mol. Cells, Apr. 30, 2005, pp. 180-184, vol. 19(2).

Klingelhöfer et al., "Dynamic interplay between adhesive and lateral E-cadherin dimers," Mol. Cell Biol., Nov. 2002, pp. 7449-7458, vol. 22(21).

Komiya, A. et al. (Oct. 2003). "Concerted expression of eotaxin-1, eotaxin-2, and eotaxin-3 in human bronchial epithelial cells," Cellular Immunology 225(2):91-100.

Letunic et al., "Smart 7: recent updates to the protein domain annotation resource," Nucleic Acids Res., Jan. 2012, pp. D302-305, vol. 40.

Lu et al., "MicroRNAsignature in patients with eosinophilic esophagitis, reversibility with glucocorticoids, and assessment as disease biomarkers," J. Allergy Clin. Immunol., Apr. 2012, pp. 1064-1075.e9, vol. 129(4).

Markowitz, J.E. et al. (Apr. 2003). "Elemental diet is an effective treatment for eosinophilic esophagitis in children and adolescents," American Journal of Gastroenterology 98(4):777-782.

Milgrom, H. et al. (Dec. 23, 1999). Treatment of allergic asthma with monoclonal anti-IgE antibody. N. Engl. J. Med. 341(26):1966-1973.

Mishra, A. et al. (Jan. 2001). "An etiological role for aeroallergens and eosinophils in Experimental esophagitis," Journal of Clinical Investigation 107(1):83-90.

Patent Cooperation Treaty, "International Preliminary Report on Patentability and Written Opinion" in corresponding International application No. PCT/US2012/044061, dated Dec. 23, 2013, 7 pgs.

Patent Cooperation Treaty, "International Search Report" in corresponding International application No. PCT/US2012/044061, dated May 25, 2013, 5 pgs.

Rothenberg, "Eosinophilic gastrointestinal disorders (EGID)," J. Allergy Clin. Immunol., Jan. 2004, pp. 11-28, vol. 113(1).

Schöneberg et al., "Structural basis of G protein-coupled receptor function," Mol. Cell. Endocrinol., May 25, 1999, pp. 181-193, vol. 151(1-2) (abstract only).

Schultz et al., "SMART, a simple modular architecture research tool: identification of signaling domains," Proc. Natl. Acad. Sci. U.S.A., May 26, 1998, pp. 5857-5864, vol. 95(11).

Sexton, "Recent advances in our understanding of peptide hormone receptors and RAMPS," Cum Opin. Drug Discov. and Devel., Sep. 1999, pp. 440-448, vol. 2(5) (abstract only).

Stappert et al., "A short core region of E-cadherin is essential for catenin binding and is highly phosphorylated," Cell Adhes. Commun., Aug. 1994, pp. 319-327, vol. 2(4) (abstract only).

Stothard, "JavaScript programs for analyzing and formatting protein and DNA sequences," BioTechniques, Jun. 2000, pp. 1102,1104, vol. 28(6).

Talley et al., "Eosinophilic gastroenteritis: a clinicopathological study of patients with disease of the mucosa, muscle layer, and subserosal tissues," Gut., Jan. 1990, pp. 54-58, vol. 31(1).

Teitelbaum, J.E. et al. (May 2002). "Eosinophilic esophagitis in children: Immunopathological analysis and response to fluticasone propionate," Gastroenterology, 122(5):1216-1225.

Vicario et al., "Local B cells and IgE production in the oesophageal mucosa in eosinophilic oesophagitis," Gut, Jan. 2010, pp. 12-20, vol. 59(1).

Yang et al., "Th17 and natural Treg cell population dynamics in systemic lupus erythematosus," Arthritis Rheum., May 2009, pp. 1472-1483, vol. 60(5).

\* cited by examiner

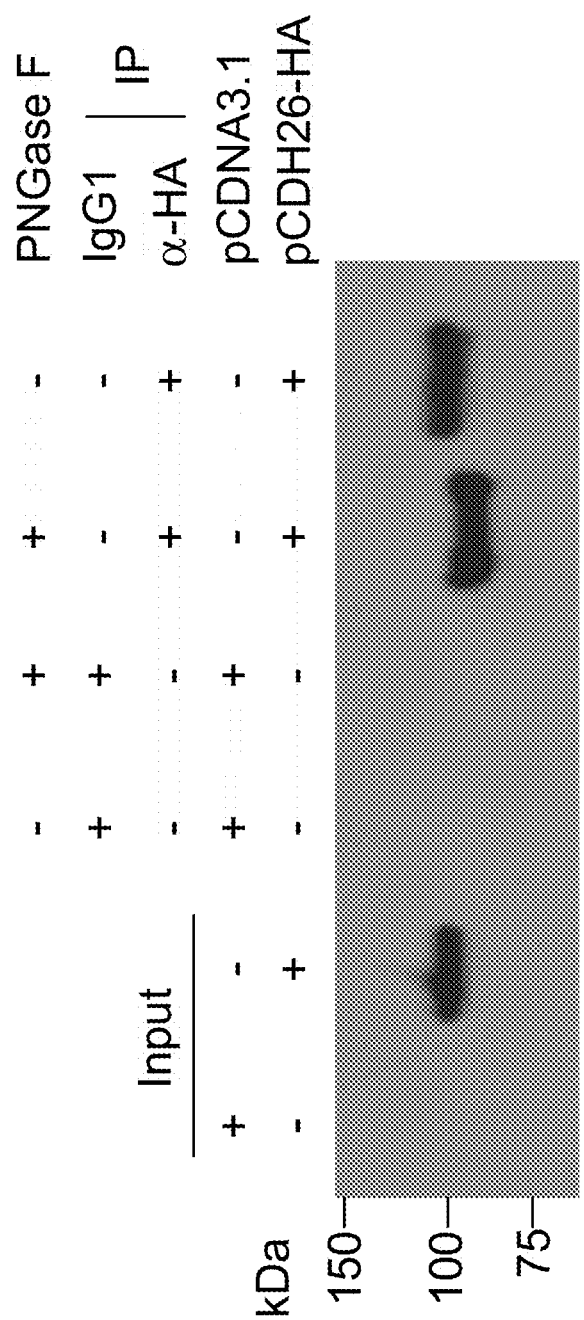

aaaaaaaagtctatttggagaattgaaataattcatggaagggaatcactattcagggattttccccttttgctctctttttccctccttaaa agaaaaattaccttctagtcctaggatgagggacacactattagtttgaattaaatgctttgatattctcagatcagccatcttgaaccaaag
             GAIT 1 caaaaccacaagttacactttcttaaaatttgatttgtcatattttctagagaaacttgaattaattgtgttattcttagcttccactggcagc
        GAIT 2          GAIT 3 ctagctttgaggg taa atgaaatgaaaatataacccatagattaccagccacttgggaacagcaggtaatactgaagaaaataaaaatagat
t ttgaaaacgtta

*Fig. 14A*

METHODS OF DETERMINING EOSINOPHILIC GASTRITIS STATUS BASED ON MARKER OR GENE EXPRESSION

CROSS REFERENCE TO RELATED APPLICATION

The present application is a Continuation Application of U.S. patent application Ser. No. 14/128,887, filed May 30, 2014, now U.S. Pat. No. 9,345,763, which is the National Stage of International Application Serial No. PCT/US2012/044061 filed Jun. 25, 2012, which claims the benefit of priority under 35 U.S.C. §119(e) to U.S. Provisional Application No.: 61/500,508, MOLECULAR DIAGNOSTIC PANEL OF EOSINOPHILIC GASTROINTESTINAL DISORDERS, filed Jun. 23, 2011, which is incorporated by reference in its entirety.

STATEMENT REGARDING FEDERALLY-SPONCERED RESEARCH

This invention was made with government support under DK076893 and AI070235 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. The ASCII copy was created on Apr. 28, 2017, is named Substitute Sequence Listing and is 100,090 bytes in size. The internal file name at <130> is 47108-513C01US.

FIELD OF THE INVENTION

The invention disclosed herein generally relates to methods and compositions for diagnosis and treatment of an eosinophilic gastritis (EG) disease state in a subject.

BACKGROUND

Eosinophilic gastrointestinal disorders (EGIDs) constitute a diverse spectrum of disorders that affect one or more parts of the gastrointestinal (GI) tract and are characterized by increased numbers of eosinophils in one or more parts of the wall of the affected GI segment(s) (Rothenberg, M. *J. Allergy Clin. Immunol.* 113:11-28 (2004); Talley, N. et al. *Gut* 31:54-8 (1990)). EGIDs include eosinophilic esophagitis (EoE, also referred to as EE in some publications), eosinophilic gastritis (EG), eosinophilic duodenitis (ED), eosinophilic jejunitis (EJ), eosinophilic ileitis (EI), and eosinophilic colitis (EC).

The EGID that has been studied the most is EoE, partly because the diagnosis is made with increasing frequency (Furuta, G. et al. *Gastroenterology* 133:1342-63 (2007)). Other EGIDs, such as EG, have been less well-studied than EoE, and diagnostic criteria are less well-established than for EoE. EG and EoE represent diseases characterized by accumulation of eosinophils in the stomach or esophagus, respectively.

SUMMARY OF THE INVENTION

Methods and compositions described herein are provided by way of example and should not in any way limit the scope of the invention.

Embodiments of the invention encompass methods of determining an eosinophilic gastritis (EG) status in a subject, including: applying a sample from the subject to a diagnostic panel that includes at least one marker or gene selected from Table 9 and/or Table 10, to obtain a result; analyzing the result to determine a level of expression of the at least one marker or gene; and determining the EG status of the subject based upon the level of expression. In some embodiments of the methods, the status includes a diagnosis of EG.

In some embodiments of the methods, the at least one marker or gene can be mRNA. In some embodiments, the at least one marker or gene can be protein. In some embodiments, the subject can be a human patient.

In some embodiments, the sample can be a tissue, an exudate, saliva, serum, plasma, blood, oral, urine, stool, or a buccal sample. In some embodiments, the sample can be a tissue sample. In some embodiments, the tissue sample can be a gastric tissue sample.

In some embodiments of the methods, the determining step includes analyzing a subset of the markers or genes in Table 9 and/or Table 10 using at least one algorithm. In some embodiments, a subset of 76 markers or genes from Table 10, or from Tables 9 and 10, can be analyzed. In some embodiments, a subset of 28 markers or genes from Table 9 and/or Table 10 can be analyzed. In some embodiments, the panel includes at least two markers or genes selected from Table 9 and/or Table 10. In some embodiments, the at least one marker or gene includes CDH26.

In some embodiments, the panel includes at least 10 markers or genes from Table 9 and/or Table 10. In some embodiments, the panel includes at least 20 markers or genes from Table 9 and/or Table 10. In some embodiments, the panel includes at least 30 markers or genes selected from Table 10, or from Tables 9 and 10. In some embodiments, the panel includes at least 60 markers or genes selected from Table 10, or from Tables 9 and 10. In some embodiments, the panel includes at least 90 markers or genes selected from Table 10, or from Tables 9 and 10. In some embodiments, the panel includes at least 100 markers or genes selected from Table 10, or from Tables 9 and 10. In some embodiments, the panel includes all of the markers or genes listed in Tables 9 and 10.

In some embodiments, the methods further include detecting, from the patient sample, a level of eotaxin-3 mRNA expression or eotaxin-3 protein.

In some embodiments, the status includes distinguishing EG from a normal condition in the subject.

In some embodiments, the status includes distinguishing EG from at least one other eosinophilic disorder in the subject. In some embodiments, the at least one other eosinophilic disorder can be eosinophilic esophagitis.

In some embodiments, the status includes distinguishing eosinophilic gastritis from at least one other inflammatory gastrointestinal disorder in the subject. In some embodiments, the at least one other inflammatory gastrointestinal disorder can be inflammatory bowel disease, *H. pylori* gastritis, or non-steroidal anti-inflammatory drug-induced gastritis.

Some embodiments of the methods further include developing or modifying a therapy for the subject based upon the results of the diagnostic panel analysis. Some embodiments further include exposure of the subject to a specific therapy. In some embodiments, the specific therapy includes targeting at least one molecule involved in EG disease pathogenesis, and/or at least one downstream gene affected by the same. In some embodiments, the at least one molecule involved in EG disease pathogenesis, and/or at least one downstream gene affected by the same, can be CDH26.

In some embodiments, the specific therapy includes an anti-CDH26-based therapeutic. In some embodiments, the anti-CDH26-based therapeutic includes at least one of a compound or composition that suppresses CDH26 activity. In some embodiments, the compound or composition that suppresses CDH26 activity includes a CDH26-Fc fusion protein, a CDH26 anti-sense polynucleotide, a CDH26-directed miRNA, a CDH26-directed shRNA, or a CDH26-directed humanized antibody. In some embodiments, the compound or composition that suppresses CDH26 activity can be one that targets a binding site and/or protein of at least one gamma-interferon-activated inhibitor of translation (GAIT) consensus sequence within a CDH26 3' untranslated region (UTR).

In some embodiments, the sample can be an archival sample. In some embodiments, the archival sample can be a formalin-fixed, paraffin-embedded (FFPE) sample.

Some embodiments of the invention further include characterizing a molecular EG profile of the subject based upon expression of the at least one marker and determining compliance with medical management based upon the profile.

Some embodiments of the invention further include determining and/or monitoring exposure to one or more therapeutic compounds in the subject based upon the level of expression.

Some embodiments of the invention further include making a determination as to the pathological development of EG in the subject based upon the expression levels of the markers.

Some embodiments of the invention further include providing personal prognostic medicine guidance to the subject based upon a determination as to the pathological development of EG in the subject, based upon the expression levels of the markers.

Some embodiments of the invention further include determining the specific genes engaged by a therapeutic, wherein the therapeutic can be administered to the subject, and a sample from the subject following therapeutic administration can be subjected to the same diagnostic panel in order to obtain a result, wherein differences between the two results determine the specific genes engaged by the administered therapeutic. In some embodiments, the results can be analyzed by comparison with normal and EG cohorts to identify genes that can be up- or down-regulated in response to environmental factors.

Embodiments of the invention also encompass EG molecular diagnostic panels including at least two genes or markers selected from Table 9 and/or Table 10. Some embodiments relate to an EG molecular diagnostic panel includes at least two genes or markers selected from Table 9. Some embodiments relate to an EG molecular diagnostic panel including at least two genes or markers selected from Table 10. Some embodiments relate to an EG molecular diagnostic panel including CDH26. Some embodiments relate to an EG molecular diagnostic panel including all of the genes or markers in Table 9 and Table 10. In some embodiments, the invention encompasses an EoE molecular diagnostic panel including eotaxin-3 mRNA and at least one marker or gene selected from Table 9 and/or Table 10.

Embodiments of the invention also encompass kits for the detection of a level of one or more genes associated with EG, including: one or more oligonucleotide probes complementary to subsequences of said one or more markers or genes, wherein the one or more markers or genes can be selected from Table 9 and/or Table 10. In some embodiments, the one or more probes can be used in at least one of a gene chip, an expression array-based protocol, a PCR protocol, or an RNA level-based protocol.

Embodiments of the invention also encompass methods of determining an allergic inflammation status in a subject, including: applying a sample from the subject to a diagnostic panel including the CDH26 marker or gene, to obtain a result; analyzing the result to determine a level of expression of CDH26; and determining the allergic inflammation status of the subject based upon the level of expression. In some embodiments, the diagnostic panel further includes at least one marker or gene selected from Table 9 and/or Table 10.

Embodiments of the invention also encompass methods of treating an allergic inflammatory condition in a subject in need thereof, including: identifying a subject with an allergic inflammatory condition; and administering to the subject an anti-CDH26-based therapeutic, wherein administration of the anti-CDH26-based therapeutic results in treatment of the allergic inflammatory condition.

In some embodiments, the anti-CDH26-based therapeutic includes at least one compound or composition that suppresses CDH26 activity. In some embodiments, the compound or composition that suppresses CDH26 activity includes at least one of a CDH26-Fc fusion protein, a CDH26 anti-sense polynucleotide, a CDH26-directed miRNA, a CDH26-directed shRNA, or a CDH26-directed humanized antibody. In some embodiments, the compound or composition that suppresses CDH26 activity can be one that targets a binding site and/or protein of at least one gamma-interferon-activated inhibitor of translation (GAIT) consensus sequence within a CDH26 3' untranslated region (UTR).

BRIEF DESCRIPTION OF THE DRAWINGS

Those of skill in the art will understand that the drawings, described below, are for illustrative purposes only. The drawings are not intended to limit the scope of the present teachings in any way.

FIG. 1A depicts hematoxylin and eosin-stained gastric antrum biopsy specimens. FIG. 1B depicts the peak eosinophil count for the gastric tissue obtained at the index endoscopy for all patients. FIG. 1C depicts the peak eosinophil count for the gastric tissue obtained at the index endoscopy for patients with active EG.

FIG. 3A depicts the relative gene expression microarray analysis of RNA isolated from the gastric antrum tissue of control patients or patients with active EG. FIG. 3B depicts eotaxin-3 gene expression in gastric tissue.

FIG. 4A depicts cadherin family member expression levels in inflamed gastric tissue. FIG. 4B depicts cadherin family member expression levels in inflamed esophageal tissue. FIG. 4C depicts CDH26 transcript levels in gastric antrum tissue as determined by microarray analysis. FIG. 4D depicts CDH26 and GAPDH transcript levels using cDNA derived from the gastric antrum tissue of the same population of patients used in the microarray study. FIG. 4E depicts relative CDH26 levels from a replication cohort of patients.

FIG. 5A depicts representative normal and EG biopsy specimens. FIG. 5B depicts high magnification of gastric antrum tissue derived from a patient with active EG stained for CDH26. FIG. 5C depicts quantification of the intensity and prevalence of CDH26-positive cells. FIG. 5D depicts CDH26 protein levels in gastric antrum.

FIG. 6A depicts cytokine gene expression in the gastric antrum tissue of the same population of patients used in the microarray study. FIG. 6B depicts cytokine gene expression in the gastric antrum tissue of the population of patients used in the replication cohort.

FIG. 7A depicts CDH26 transcript from the esophageal tissue of either normal patients or patients with EoE. FIG. 7B depicts CDH26 transcript levels from the esophageal tissue of patients obtained during the index endoscopy from which the gastric specimens were obtained. FIG. 7C depicts CDH26 protein expression and localization in esophageal tissue. FIG. 7D depicts CDH26 and beta-actin (top) and their ratio (bottom) from total protein lysates prepared from esophageal biopsy specimens from an independent cohort of patients who either had active EoE or no history of EGID.

FIG. 8A depicts primary esophageal epithelial cells were cultured from distal esophageal biopsy specimens. FIG. 8B depicts TE-7 cells after being treated with IL-13. FIG. 8C depicts NCI-N87 cells after being treated with IL-13. FIG. 8D depicts TE-7 cells that were transduced with either pMIRNA1-puro-control or -CDH26. FIG. 8E depicts surface biotinylation of TE-7 cells. FIG. 8F depicts surface biotinylation of NCI-N87 cells.

FIGS. 9A-F depict the biochemical characterization of CDH26 and investigation of CDH26 protein-protein interactions. FIG. 9A depicts western blot analysis after transiently transfecting HEK 293T cells with the indicated construct(s). FIG. 9B depicts the western blot analysis following post-translational modification of CDH26. FIG. 9C depicts the similarity between the beta-catenin binding domain of CDH1 (E-cadherin, SEQ ID NO: 139) and the corresponding domain of CDH26 (SEQ ID NO: 140). FIG. 9D depicts western blot analysis after transiently transfecting HEK 293T cells with the indicated construct(s). FIG. 9E depicts western blot analysis after transiently transfecting HEK 293T cells with the indicated construct(s). FIG. 9F depicts western blot analysis after transiently transfecting HEK 293T cells with the indicated construct(s).

FIG. 10A depicts western blot analysis for CDH26 and beta-actin for cells that were treated with sulfo-NHS-LC-biotin to biotinylate surface proteins. FIG. 10B depicts FACS analysis of cells stained with either anti-CDH26 or an equivalent amount of IgG control antibody. FIG. 10C depicts immunofluorescence microscopy of cells stained with either anti-CDH26 or an equivalent amount of IgG control antibody.

FIG. 13A depicts results showing that CDH26 overexpression increases HEK 293T cell adhesion. FIG. 13B depicts results demonstrating that TE-7 cells that overexpress CDH26 exhibit increased secretion of eotaxin-3 after stimulation with IL-13 compared to control cells.

FIGS. 14A-B depict the CDH26 3' untranslated region (UTR) sequence and show that deletion of particular sequences within this 3' UTR result in increased protein expression. FIG. 14A depicts the CDH26 3' UTR sequence (SEQ ID NO: 141). FIG. 14B depicts the ratio of Firefly to *Renilla* luciferase for each sample.

DETAILED DESCRIPTION OF THE INVENTION

Figure 1A:
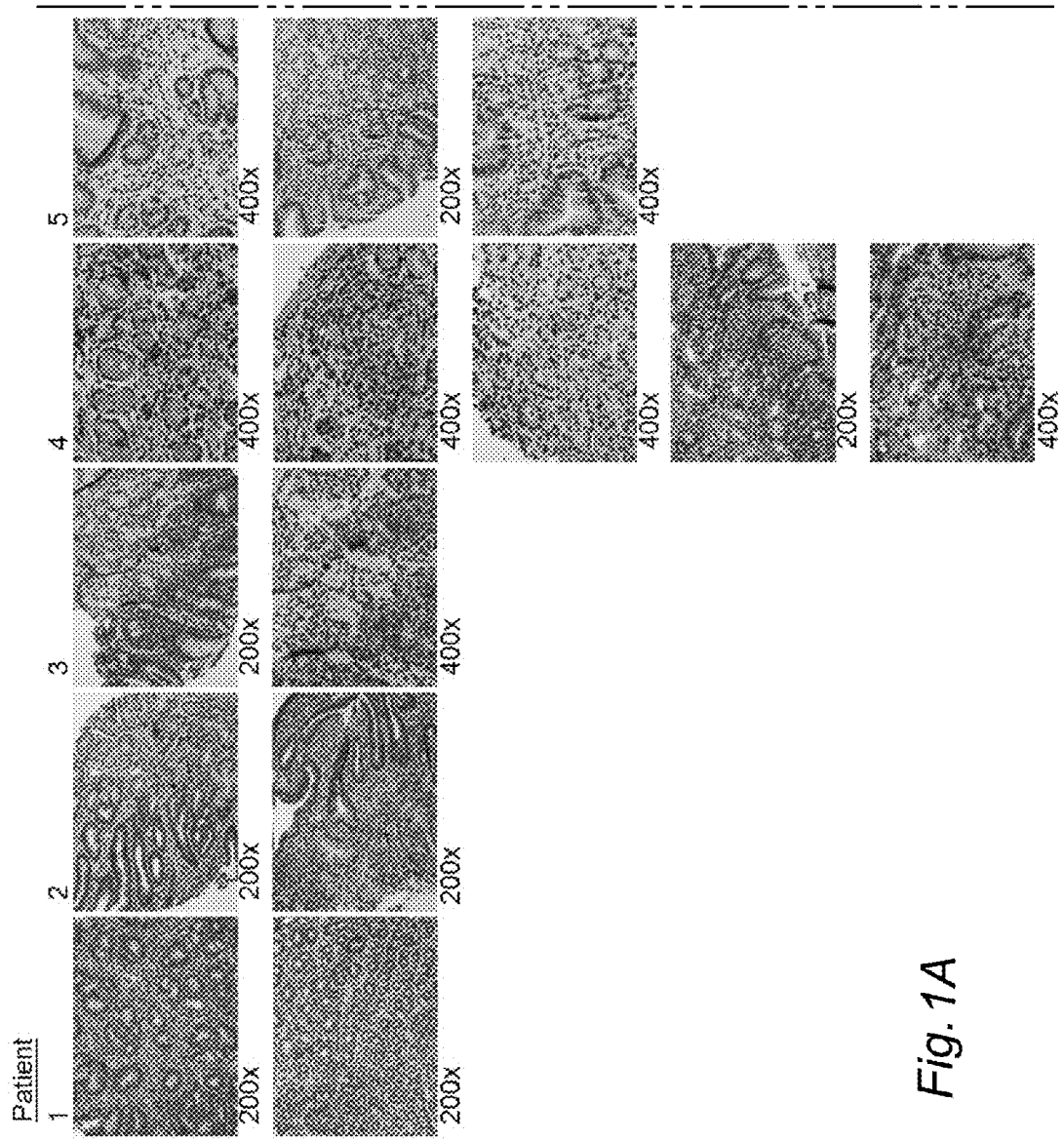
FIGS. 1A-C depict results demonstrating that the gastric tissue of patients with eosinophilic gastritis (EG) displays marked eosinophilic inflammation that correlates with peripheral blood eosinophil counts.
Figure 1A:
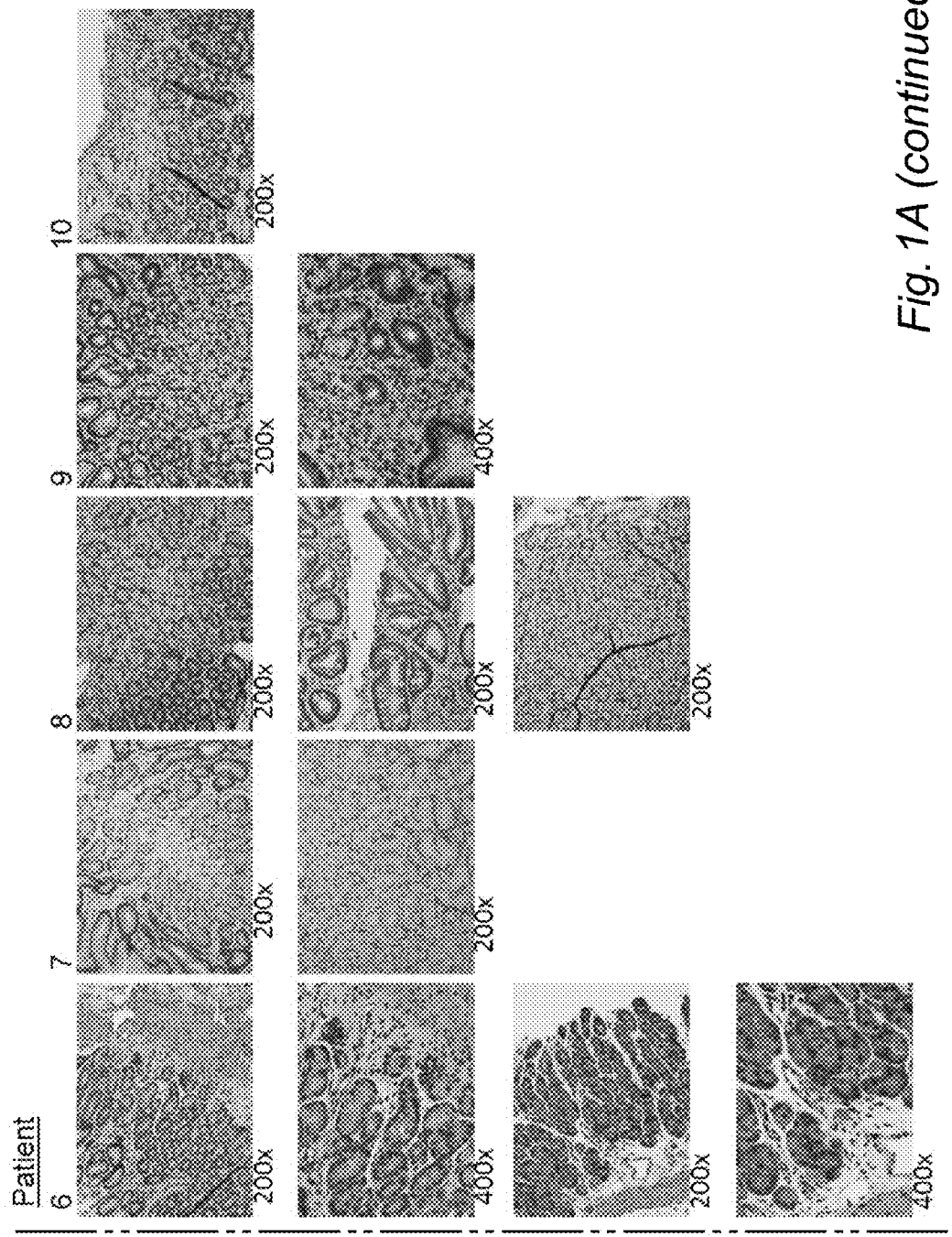

All references cited herein are incorporated by reference in their entirety. Also incorporated herein by reference in their entirety include: U.S. Patent Application No. 60/633,909, EOTAXIN-3 IN EOSINOPHILIC ESOPHAGITIS, filed on Dec. 27, 2004; U.S. Pat. No. 8,030,003, DIAGNOSIS OF EOSINOPHILIC ESOPHAGITIS BASED ON PRESENCE OF AN ELEVATED LEVEL OF EOTAXIN-3, issued Oct. 4, 2011 and filed as U.S. patent application Ser. No. 11/721,127 on Jun. 7, 2007; U.S. patent application Ser. No. 12/492,456, EVALUATION OF EOSINOPHILIC ESOPHAGITIS, filed on Jun. 26, 2009; U.S. patent application Ser. No. 12/628,992, IL-13 INDUCED GENE SIGNATURE FOR EOSINOPHILIC ESOPHAGITIS, filed on Dec. 1, 2009; U.S. Provisional Application No. 61/430,453, A STRIKING LOCAL ESOPHAGEAL CYTOKINE EXPRESSION PROFILE IN EOSINOPHILIC ESOPHAGITIS, filed on Jan. 6, 2011; U.S. patent application Ser. No. 13/051,873, METHODS AND COMPOSITIONS FOR MITIGATING EOSINOPHILIC ESOPHAGITIS BY MODULATING LEVELS AND ACTIVITY OF EOTAXIN-3, filed on Mar. 18, 2011; U.S. patent application Ser. No. 13/132,884, DETERMINATION OF EOSINOPHILIC ESOPHAGITIS, filed on Jun. 3, 2011; U.S. Provisional Application No. 61/497,796, NEGATIVE REGULATION OF EOSINOPHIL PRODUCTION BY TOLL-LIKE RECEPTORS, filed on Jun. 16, 2011; U.S. Provisional Application No. 61/571,115, DIAGNOSTIC METHODS OF EOSINOPHILIC ESOPHAGITIS, filed on Jun. 21, 2011; U.S. patent application Ser. No. 13/132,295, METHODS OF DETERMINING EFFICACY OF GLUCOCORTICOID TREATMENT OF EOSINOPHILIC ESOPHAGITIS, filed on Aug. 22, 2011; PCT Patent Application No. US2012/020556, ESOPHAGEAL CYTOKINE EXPRESSION PROFILES IN EOSINOPHILIC ESOPHAGITIS, filed on Jan. 6, 2012; U.S. Provisional Application No. 61/602,897, ESOPHAGEAL MICRORNA EXPRESSION PROFILES IN EOSINOPHILIC ESOPHAGITIS, filed on Feb. 24, 2012; PCT Patent Application No. TBD, BLOCKAGE OF EOSINOPHIL PRODUCTION BY TOLL-LIKE RECEPTORS, filed on Jun. 18, 2012; and PC Patent Application No. TBD, DIAGNOSTIC METHODS FOR EOSINOPHILIC ESOPHAGITIS, filed on Jun. 21, 2012.

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, plasma, blood cells (e.g., white cells), circulating cells (e.g., stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom, and the like. Samples can also include sections of tissues such as frozen or fixed sections taken for histological purposes or microdissected cells or extracellular parts thereof. A sample to be analyzed is tissue material from a gastric tissue biopsy obtained by aspiration or punctuation, excision or by any other surgical method leading to biopsy or resected cellular material. Such a sample can comprise cells obtained from a subject or patient. In some embodiments, the sample is a body fluid that include, for example, blood fluids, serum, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "modulated" or "modulation," or "regulated" or "regulation" and "differentially regulated" refers to both upregulation (i.e., activation or stimulation, e.g., by agonizing or potentiating) and down regulation (i.e., inhibition or suppression, e.g., by antagonizing, decreasing or inhibiting).

As used herein, the term "diagnosing or monitoring" with reference to eosinophilic gastritis (EG) refers to a method or process of determining if a subject has or does not have EG, or determining the severity or degree of EG, or determining the remission status of EG.

As used herein, the term "subject" refers to any member of the animal kingdom. In some embodiments, a subject is a human patient.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "transcriptome" refers to the set of all messenger RNA (mRNA) molecules, or "transcripts," produced in one or a population of cells. This term can also include non-translated RNAs which affect cellular characteristics because of gene regulation functions (silencing or activation or stabilization or degradation of other genes and transcripts). The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all RNA transcripts in the cell, the transcriptome reflects the genes that are being actively expressed at any given time, with the exception of mRNA degradation phenomena such as transcriptional attenuation. It also includes posttranscriptional events such as alternative splicing.

As used herein, the term "expression levels" refers, for example, to a determined level of gene expression. The term "pattern of expression levels" refers to a determined level of gene expression compared either to a reference gene (e.g. a housekeeping gene or inversely regulated genes) or to a computed average expression value (e.g. in DNA-chip analyses). A pattern is not limited to the comparison of two genes but is more related to multiple comparisons of genes to reference genes or samples. A certain "pattern of expression levels" can also result and be determined by comparison and measurement of several genes as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, an "eosinophilic disorder", or "eosinophilia-associated condition", or "eosinophilia-associated disease" can refer to any condition that features an enhanced level of eosinophils or their activation state or a disease with clinical or pathological features caused by eosinophils, at least in part. Such conditions include, but are not limited to, eosinophil-associated gastrointestinal disorder, eosinophilic esophagitis, eosinophilic gastritis, eosinophilic gastroenteritis, eosinophilic colitis, eosinophilic jejunitis, eosinophilic duodenitis, eosinophilic pneumonia, eosinophilic fascitis, eosinophilic cellulitis, eosinophilic vasculitis, eosinophilic myositis, allergies, asthma, atopic dermatitis, nasal polyposis, allergic rhinitis, drug eruption, drug hypersensitivity, eosinophilic cystitis, interstitial cystitis, bullous pemhigoid, bullous vegetans, primary immunodeficiency, acquired immunodeficiency syndrome (AIDS), infection such as invasive *aspergillus fumigatus*, allergic bronchopulmonary aspergillosis, eosinophilic leukemia, Churg-Strauss syndrome, and hypereosinophilic syndrome, and the like.

As used herein, an "inflammatory gastrointestinal disorder" can refer to any condition that features a level of inflammation in the gastrointestinal tract, with or without the presence of eosinophils. Such conditions include, but are not limited to, inflammatory bowel disease (IBD), *H. pylori* gastritis, non-steroidal anti-inflammatory drug (NSAID) gastritis, acute gastritis, alcohol-induced gastritis, peptic ulcer disease, and the like.

As used herein, an "allergic inflammatory condition" or "allergic inflammatory disorder" can refer to any condition that features eosinophil and/or mast cell-associated inflammation, allergen-induced gastrointestinal inflammation, and/or symptoms associated therewith. Such conditions include, but are not limited to, eosinophilic disorders, inflammatory gastrointestinal disorders, food-protein gastroenteritis, and the like.

Eosinophilic esophagitis (EoE) has a unique transcriptome identified in gene microarray studies of esophageal biopsies from affected patients (Blanchard, C. et al. *J. Allergy Clin. Inmnunol.* 118:1054-9 (2006)). The most upregulated gene in EoE is eotaxin-3, a cytokine that attracts eosinophils into tissue. Eotaxin-3 is expressed by esophageal epithelial cells in EoE in vivo and in vitro, and the T helper ($T_H2$) cytokine interleukin-13 (IL-13) is markedly increased in EoE biopsies and induces esophagcal epithelial cells cultured from EoE to increase eotaxin-3 expression (Blanchard, C. et al. *J. Allergy Clin. Immunol.* 118:1054-9 (2006); Blanchard, C. et al. *J. Immunol.* 184:4033-41 (2010)).

While EoE has been described considerably, other forms of eosinophilic gastrointestinal disorders (EGIDs), such as eosinophilic gastritis (EG), are less well understood, with poorly defined diagnostic criteria. As described herein, biopsies from EG patients were studied using a variety of methods in order to increase knowledge of the genetic and molecular abnormalities in EG. Global transcript analysis was performed to identify genes differentially expressed in the gastric tissue of patients with active EG compared to control individuals. Further characterization of the gene and protein expression patterns of cadherin-like 26 (CDH26), a heretofore undescribed cadherin that seems to be specific for allergic inflammation, was undertaken through real-time PCR, immunohistochemistry, and western blot analysis, as CDH26 was found to be a gene product markedly overexpressed in EGID tissue. CDH26 protein interactions were examined using transient transfection and immunoprecipitation analysis.

As described herein, gastric tissue of patients with EG was found to exhibit a conserved pattern of gene expression. A conserved set of 28 genes were found to be up-regulated and 76 found to be down-regulated in gastric tissue of patients with active EG compared to control patients. Of these genes, only 11 overlapped with those previously identified as being dysregulated in the esophageal tissue of patients with EoE, including CDH26, which represented the most highly overexpressed gene in EG biopsies (20.9-fold, p <0.01). Epithelial cells exhibited increased CDH26 protein expression in both esophageal and gastric tissue of patients with active EoE or EG, respectively. Similar to EoE, IL-13 transcript levels were highly increased in the gastric tissue of patients with active EG (375-fold, p <0.01). IL-13 was found to induce CDH26 expression in primary esophageal epithelial cells, TE-7 esophageal epithelial cells, and NCI-N87 gastric cells in vitro. CDH26, an uncharacterized member of the cadherin superfamily of proteins, exhibited homotypic interaction and additionally interacted with beta-catenin, alpha-catenin, and p120/delta-catenin when expressed ectopically in HEK 293T cells.

The results presented herein define a molecular signature in the gastric tissue of patients with EG and demonstrate EG inflammation mechanisms by identifying a signature of genes commonly dysregulated in the gastric tissue of EG patients, thereby elucidating the molecular pathways that underly the pathogenesis of this disease. These findings provide a set of genes that can be used for the molecular diagnosis of EG. Because stomach biopsies are routinely obtained with esophageal biopsies during upper endoscopy, the EG diagnostic panel described herein can be combined with existing esophageal diagnostic panels to provide a powerful diagnostic tool for eosinophilic conditions. The EG diagnostic panel, or at least one marker or gene from Table 9 and/or Table 10 or a subset of markers or genes from Table 9 and/or Table 10, can be used alone or can be enhanced by combination with determination of eotaxin-3 mRNA expression levels or eotaxin-3 protein.

In addition, the expression pattern and function of CDH26, a gene product markedly overexpressed in EGID tissue, has been determined for EG and EoE. CDH26 transcripts and protein are highly upregulated in both the esophageal tissue of patients with active EoE and the gastric tissue of patients with active EG. CDH26 was found to have the functional activity of modifying eosinophil chemoattraction. Furthermore, CDH26 was found to have the functional activity of modifying cell adhesion. Additionally, CDH26 was found to have the functional activity of modifying the effects of IL-13 on epithelial cells.

IL-13 transcript levels were found to be significantly increased in the gastric tissue of patients with active EG, and CDH26 was found to be regulated in part by IL-13 in esophageal and gastric epithelial cells. Furthermore, CDH26 molecules were further found to exhibit homotypic interaction and form complexes containing catenin proteins, such as beta-catenin, alpha-catenin, and p120, similar to other molecules in the cadherin family of proteins; the catenin proteins link cadherin molecules to the actin cytoskeleton. These findings demonstrate the function of CDH26 in cell adhesion. In addition, eosinophil transmigration through monolayers of HEK 293T cells overexpressing CDH26 is increased compared to transmigration through control cells. As such, CDH26 was found to be a major cadherin that is regulated by IL-13, which is a $T_H2$- and allergy-promoting cytokine, and is found to be expressed in allergic GI tissue and with a key role in various aspects of allergic disease pathogenesis and diagnosis.

CDH26 is therefore involved with allergic inflammation in general, including EGIDs, inflammatory GI disorders, and other allergic diseases. Accordingly, anti-CDH26-based therapeutics can be used to treat allergic diseases.

Accordingly, embodiments of the invention are directed to methods of diagnosing EG in a subject, wherein the methods comprise applying a sample from the subject to a diagnostic panel that contains markers selected from Tables 9 and 10, analyzing the results to determine expression levels of the markers, and making a determination as to the EG status of the subject based upon the expression levels of the markers.

Embodiments of the invention are also directed to methods of distinguishing EG from other disorders in a subject, wherein the methods comprise applying a sample from the subject to a diagnostic panel that contains markers or genes selected from Tables 9 and 10, analyzing the results to determine expression levels of the markers, and making a determination as to the EG status of the subject based upon the expression levels of the markers. In some embodiments, the other disorder is an EGID. For example, some embodiments involve the differentiation of EG from EoE, which should not involve abnormal expression of markers or genes selected from Tables 9 and 10 in the stomach. In some embodiments, the other disorder is a non-eosinophilic inflammatory GI disorder. For example, some embodiments involve the differentiation of EG from inflammatory bowel disease (IBD) or non-eosinophilic gastritis, such as *H. pylori* gastritis or non-steroidal anti-inflammatory drug (NSAID) gastritis, or the like.

Embodiments of the invention are also directed to methods of distinguishing EG from other inflammatory GI disorders in a subject, wherein the methods comprise applying a sample from the subject to a diagnostic panel that contains markers selected from Tables 9 and 10, analyzing the results to determine expression levels of the markers, and making a determination as to the EG status of the subject based upon the expression levels of the markers.

Embodiments of the invention are also directed to methods of monitoring or guiding treatment for a subject suffering from EG, wherein the methods comprise applying a sample from the subject to a diagnostic panel that contains markers selected from Tables 9 and 10, analyzing the results to determine expression levels of the markers, and making a determination as to the EG status of the subject based upon the expression levels of the markers, and developing or modifying a therapy for the subject based upon the results of the diagnostic panel. In some embodiments, the monitoring of treatment includes identifying exposure to a specific therapy. In some embodiments, the specific therapy is one that targets EG molecules, or downstream genes affected by the same.

Embodiments of the invention also relate to methods of analyzing an archival sample obtained from a subject for indication of EG in the subject, the methods comprising obtaining the archival sample, applying the to a diagnostic panel that contains markers selected from Tables 9 and 10, analyzing the results to determine expression levels of the markers, and making a determination as to the EG status of the subject based upon the expression levels of the markers. In some embodiments, the archival sample is a formalin-fixed, paraffin-embedded (FFPE) sample.

Embodiments of the invention also relate to methods of developing or modifying a therapy for a subject in need thereof, the methods comprising applying a sample from the subject to a diagnostic panel that contains markers selected from Tables 9 and 10, analyzing the results to determine expression levels of the markers, and making a determination as to the EG status of the subject based upon the expression levels of the markers, and developing or modifying a therapy for the subject based upon the determination.

Embodiments of the invention also relate to methods of determining compliance with medical management in a subject undergoing therapy for EG, the methods comprising applying a sample from the subject to a diagnostic panel that contains markers selected from Tables 9 and 10, analyzing the results to determine expression levels of the markers, and making a determination as to the EG status of the subject based upon the expression levels of the markers, and determining compliance with medical management based upon the determination.

Embodiments of the invention are also directed to kits for the detection of a level of one or more genes associated with EG, comprising one or more oligonucleotide probes complementary to subsequences of said one or more markers or genes, wherein the one or more markers or genes are selected from Table 9 and/or Table 10. In some embodiments, the one or more probes are used in at least one of a gene chip, an expression array-based protocol, a PCR protocol, or an RNA level-based protocol, including, for example, RNA-seq, and the like.

Embodiments of the invention also relate to methods of determining an allergic inflammation status in a subject, including applying a sample from the subject to a diagnostic panel that comprises the CDH26 marker or gene, to obtain a result, analyzing the result to determine a level of expression of CDH26, and determining the allergic inflammation status of the subject based upon the level of expression. In some embodiments, the diagnostic panel further comprises at least one marker or gene selected from Table 9 and/or Table 10.

Embodiments of the invention are also directed to methods of treating an allergic inflammatory condition in a subject in need thereof, including identifying a subject with an allergic inflammatory condition, and administering to the subject an anti-CDH26-based therapeutic, wherein administration of the anti-CDH26-based therapeutic results in treatment of the allergic inflammatory condition. In some embodiments, wherein the anti-CDH26-based therapeutic includes compounds or compositions that suppress CDH26 activity. In some embodiments, the compound or composition that suppresses CDH26 activity includes CDH26-Fc fusion proteins, CDH26 anti-sense polynucleotides, CDH26-directed microRNAs (miRNAs), CDH26-directed short hairpin RNAs (shRNAs), CDH26-directed humanized antibodies, CDH-related peptides, or catenin-based inhibitors. In some embodiments, the compound or composition that suppresses CDH26 activity is one that targets a binding site and/or protein of at least one gamma-interferon-activated inhibitor of translation (GAIT) consensus sequence within a CDH26 3' untranslated region (UTR).

In an exemplary embodiment of the invention, the method disclosed herein can include three steps, which can be finished within 1 working day (6-8 hours with multiple sample capacity). RNA extraction can be performed on a patient gastric biopsy sample. After RNA quantity/quality measurement, RNA from the sample is subjected to reverse transcription (RT) reaction. Next, cDNA corresponding to the reverse-transcribed RNA or mRNA directly is analyzed for expression of at least one of the genes, or a subset of the genes or all of the genes, as listed in Tables 9 and 10, as a single or multiplex format using at least one of a variety of gene quantification techniques. The data is analyzed to determine expression levels of the markers or genes as disclosed herein to establish an EG diagnosis, which serves as the basis for the final diagnostic report. The EG diagnosis can serve as a basis for a final diagnostic report as well as in assisting selection or modification of an appropriate therapy for the patient.

In some embodiments, the EG markers or genes are measured using a fluidic card loaded with the EG markers or genes. In some embodiments, the representative EG genes described herein or a subset of these genes are measured using other methods and/or tools, including for example, but not limited to, Taqman (Life Technologies, Carlsbad, Calif.), Light-Cycler (Roche Applied Science, Penzberg, Germany), ABI fluidic card (Life Technologies), NanoString® (NanoString Technologies, Seattle, Wash.), NANODROP® technology (Thermo Fisher Scientific (Wilmington, Del.), and the like. The person of skill in the art will recognize such other formats and tools, which can be commercially available or which can be developed specifically for such analysis.

In some embodiments, CDH26, which can be used as a marker or gene for allergic inflammatory conditions, is measured using a fluidic card loaded with the CDH26 marker or gene. In some embodiments, CDH26 can be used alone or in combination with one or more of the representative EG genes described herein or a subset of these genes and can be measured using other methods and/or tools, including for example, but not limited to, Taqman (Life Technologies, Carlsbad, Calif.), Light-Cycler (Roche Applied Science, Penzberg, Germany), ABI fluidic card (Life Technologies), NanoString® (NanoString Technologies, Seattle, Wash.), NANODROP® technology (Thermo Fisher Scientific (Wilmington, Del.), and the like. The person of skill in the art will recognize such other formats and tools, which can be commercially available or which can be developed specifically for such analysis.

EG Diagnostic Genes

In embodiments of the invention, EG is diagnosed based upon a panel containing markers or genes selected from the representative EG genes listed in Tables 9 and 10.

In some embodiments the diagnostic panel contains at least one marker or gene selected from Tables 9 and 10. In some embodiments the at least one marker or gene includes CDH26. In some embodiments the diagnostic panel contains at least 10 markers or genes selected from Tables 9 and 10. In some embodiments, the diagnostic panel contains at least 20 markers or genes selected from Tables 9 and 10. In some embodiments, the diagnostic panel contains at least 30 markers or genes selected from Tables 9 and 10. In some embodiments, the diagnostic panel contains at least 40 markers or genes selected from Tables 9 and 10. In some embodiments, the diagnostic panel contains at least 50 markers or genes selected from Tables 9 and 10. In some embodiments, the diagnostic panel contains at least 60 markers or genes selected from Tables 9 and 10. In some embodiments, the diagnostic panel contains at least 70 markers or genes selected from Tables 9 and 10. In some embodiments, the diagnostic panel contains at least 80 markers or genes selected from Tables 9 and 10. In some embodiments, the diagnostic panel contains at least 90 markers or genes selected from Table Tables 9 and 10. In some embodiments, the diagnostic panel contains at least 100 markers or genes selected from Tables 9 and 10.

In some embodiments of the invention, the diagnostic panel contains 1, 2, 3, 4, 5, 6, 7, 8, or 9 markers or genes selected from Tables 9 and 10. In some embodiments of the invention, the diagnostic panel contains 10, 11, 12, 13, 14, 15, 16, 17, 18, or 19 markers or genes selected from Tables 9 and 10. In some embodiments of the invention, the diagnostic panel contains 20, 21, 22, 23, 24, 25, 26, 27, 28, or 29 markers or genes selected from Tables 9 and 10. In some embodiments of the invention, the diagnostic panel contains 30, 31, 32, 33, 34, 35, 36, 37, 38, or 39 markers or genes selected from Tables 9 and 10. In some embodiments of the invention, the diagnostic panel contains 40, 41, 42, 43, 44, 45, 46, 47, 48, or 49 markers or genes selected from Tables 9 and 10. In some embodiments of the invention, the diagnostic panel contains 50, 51, 52, 53, 54, 55, 56, 57, 58, or 59 markers or genes selected from Tables 9 and 10. In some embodiments of the invention, the diagnostic panel contains 60, 61, 62, 63, 64, 65, 66, 67, 68, or 69 markers or genes selected from Tables 9 and 10. In some embodiments of the invention, the diagnostic panel contains 70, 71, 72, 73, 74, 75, 76, 77, 78, or 79 markers or genes selected from Tables 9 and 10. In some embodiments of the invention, the diagnostic panel contains 80, 81, 82, 83, 84, 85, 86, 87, 88, or 89 markers or genes selected from Tables 9 and 10. In some embodiments of the invention, the diagnostic panel contains 90, 91, 92, 93, 94, 95, 96, 97, 98, or 99 markers or genes selected from Tables 9 and 10. In some embodiments of the invention, the diagnostic panel contains 100, 101, 102, 103, or 104 markers or genes selected from Tables 9 and 10.

In some embodiments, the diagnostic panel contains anywhere between 1 to 28 markers or genes selected from Tables 9 and 10. In some embodiments, the diagnostic panel contains anywhere between 1 to 76 markers or genes selected from Tables 9 and 10. In some embodiments, the diagnostic panel contains all of the markers or genes listed in Tables 9 and 10.

Allergic Inflammatory Diagnostic Genes

In embodiments of the invention, an allergic inflammatory condition is diagnosed based upon expression of the CDH26 marker or gene.

In some embodiments, diagnosis of an allergic inflammatory condition is based upon a panel containing CDH26 and markers or genes selected from the genes listed in Tables 9 and 10. In some embodiments, the diagnostic panel contains CDH26 and at least one marker or gene selected from Tables 9 and 10.

Anti-CDH-26-based Therapeutics

Some embodiments of the invention relate to blocking or suppressing CDH26 activity by administration of an anti-CDH26-based therapeutic, thereby treating an allergic inflammatory condition.

In some embodiments, anti-CDH26-based therapeutics that can be used in the treatment of allergic inflammatory conditions include for example, but are not limited to, CDH26-Fc fusion proteins, CDH26 anti-sense polynucleotides, CDH26-directed microRNAs (miRNAs), CDH26-directed short hairpin RNAs (shRNAs), CDH26-directed humanized antibodies, CDH-related peptides, catenin-based inhibitors, and the like. In some embodiments, anti-CDH26-based therapeutics that can be used in the treatment of allergic inflammatory conditions include for example, but are not limited to, compounds or compositions that target a binding site and/or protein of at least one GAIT consensus sequence within a CDH26 3' UTR.

In some embodiments, anti-CDH26-based therapeutics that can be used in the treatment of allergic inflammatory conditions include molecules that are structurally similar to those listed above. Structurally similar compounds are those that are not structurally identical but can have similar CDH26 inhibitory function, though the CDH26 inhibitory function can be substantially increased or decreased. Heretofore unknown anti-CDH26-based therapeutics can be contemplated and designed based on knowledge of a known anti-CDH26-based therapeutic. Anti-CDH26-based therapeutics for the treatment of eosinophilia-associated conditions can be identified by known methodologies. One of skill in the art can recognize anti-CDH26-based therapeutics that can be used in the present invention.

Heretofore unknown anti-CDH26-based therapeutics can be developed by the screening of various compounds. Compounds that can be screened to determine their utility as anti-CDH26-based therapeutics include for example, but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular libraries made of D- or L-configuration amino acids, or both, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), organic and inorganic molecules, and the like.

In addition to the more traditional sources of test compounds, computer modeling and searching technologies permit the rational selection of test compounds by utilizing structural information from the ligand binding sites relevant proteins. Such rational selection of test compounds can decrease the number of test compounds that must be screened in order to identify a therapeutic compound. Knowledge of the sequences of relevant proteins allows for the generation of models of their binding sites that can be used to screen for potential ligands. This process can be accomplished in several manners known in the art. A preferred approach involves generating a sequence alignment of the protein sequence to a template (derived from the crystal structures or NMR-based model of a similar protein(s), conversion of the amino acid structures and refining the model by molecular mechanics and visual examination. If a strong sequence alignment cannot be obtained then a model can also be generated by building models of the hydrophobic helices. Mutational data that point towards residue-residue contacts can also be used to position the helices relative to each other so that these contacts are achieved. During this process, docking of the known ligands into the binding site cavity within the helices can also be used to help position the helices by developing interactions that would stabilize the binding of the ligand. The model can be completed by refinement using molecular mechanics and loop building using standard homology modeling techniques. (General information regarding modeling can be found in Schoneberg, T. et. al. *Molecular and Cellular Endocrinology* 151:181-93 (1999); Flower, D. *Biochimica et Biophysica Acta* 1422:207-34 (1999); and Sexton, P. *Current Opinion in Drug Discovery and Development* 2:440-8 (1999).)

Once the model is completed, it can be used in conjunction with one of several existing computer programs to narrow the number of compounds to be screened by the screening methods of the present invention, like the DOCK program (UCSF Molecular Design Institute, San Francisco, Calif.). In several of its variants it can screen databases of commercial and/or proprietary compounds for steric fit and rough electrostatic complementarity to the binding site. Another program that can be used is FLEXX (Tripos Inc., St. Louis, Mo.).

Administration

Administration of anti-CDH26-based therapeutics as disclosed herein can be used in methods of treating or preventing an allergic inflammatory condition in a subject in need thereof. Anti-CDH26-based therapeutics include those that suppresses CDH26 activity. For example, anti-CDH26-based therapeutics include, but are not limited to, CDH26-Fc fusion proteins, CDH26 anti-sense polynucleotides, CDH26-directed miRNAs, CDH26-directed shRNAs, CDH26-directed humanized antibodies, CDH-related peptides, catenin-based inhibitors, and the like. Anti-CDH26-based therapeutics also include compounds or compositions that target a binding site and/or protein of at least one GAIT consensus sequence within a CDH26 3' UTR.

Anti-CDH26-based therapeutics can be administered by any pharmaceutically acceptable carrier, including, for example, any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional medium or agent is incompatible with the active compound, such media can be used in the compositions of the invention. Supplementary active compounds can also be incorporated into the compositions. A pharmaceutical composition of the invention is formulated to be compatible with its intended route of administration. Routes of administration include for example, but are not limited to, intravenous, intramuscular, and oral, and the like. Additional routes of administration include, for example, sublingual, buccal, parenteral (including, for example, subcutaneous, intramuscular, intraarterial, intradermal, intraperitoneal, intracisternal, intravesical, intrathecal, or intravenous), transdermal, oral, transmucosal, and rectal administration, and the like.

Solutions or suspensions used for appropriate routes of administration, including, for example, but not limited to parenteral, intradermal, or subcutaneous application, and the like, can include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose, and the like. The pH can be adjusted with acids or bases, such as, for example, hydrochloric acid or sodium hydroxide, and the like. The parenteral preparation can be enclosed in, for example, ampules, disposable syringes, or multiple dose vials made of glass or plastic, and the like.

Pharmaceutical compositions suitable for injectable use include, for example, sterile aqueous solutions (where water soluble) or dispersions and sterile powders for the extemporaneous preparation of sterile injectable solutions or dispersion, and the like. For intravenous administration, suitable carriers include, for example, physiological saline, bacteriostatic water, Cremophor EL™ (BASF, Parsippany, N.J.) or phosphate buffered saline (PBS), and the like. In all cases, the composition should be fluid to the extent that easy syringability exists. The carrier can be a solvent or dispersion medium containing, for example, water, ethanol, polyol (for example, glycerol, propylene glycol, and liquid polyethylene glycol, and the like), and suitable mixtures thereof, and the like. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, such as, for example, parabens, chlorobutanol, phenol, ascorbic acid, thimerosal, and the like. In many cases, it can be preferable to include isotonic agents, such as, for example, sugars, polyalcohols such as mannitol, sorbitol, and sodium chloride, and the like, in the composition. Prolonged absorption of the injectable compositions can be brought about by including in the composition an agent which delays absorption such as, for example, aluminum monostearate and gelatin, and the like.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets, for example. For oral administration, the agent can be contained in enteric forms to survive the stomach or further coated or mixed to be released in a particular region of the gastrointestinal (GI) tract by known methods. For the purpose of oral therapeutic administration, the active compound can be incorporated with excipients and used in the form of tablets, troches, or capsules, or the like. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following exemplary ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate; a glidant such as colloidal silicon dioxide; a sweetening agent such as sucrose or saccharin; or a flavoring agent such as peppermint, methyl salicylate, or orange flavoring, or the like.

For administration by inhalation, the compounds can be delivered in the form of an aerosol spray from pressured container or dispenser, which contains a suitable propellant, e.g., a gas such as carbon dioxide, or a nebulizer, or the like.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives, and the like. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems, and the like. Biodegradable, biocompatible polymers can be used, such as, for example, ethylene vinyl acetate, polyanhydrides, polyglycolic acid, collagen, polyorthoesters, and polylactic acid, and the like. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference in its entirety.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The details for the dosage unit forms of the invention are dictated by and directly dependent on the unique characteristics of the active compound and the particular therapeutic effect to be achieved, and the limitations inherent in the art of compounding such an active compound for the treatment of individuals. Such details are known to those of skill in the art.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Patient Selection

Entry criteria were that patients who had signs and symptoms consistent with upper GI tract disease and had biopsies that documented active eosinophilic gastritis (EG), with gastric tissue samples preserved for genetic and molecular analyses. The endoscopic procedure at which samples for histopathology, gene microarray, and PCR analyses were obtained was designated the incident endoscopy. All gastric samples used for ancillary studies were obtained from the antrum, and all samples obtained for routine histology and immunohistochemistry were obtained from the antrum or antrum/body.

Active EG was defined as increased numbers of eosinophils, which were the predominant inflammatory cells in some areas, in a gastric biopsy that showed architectural abnormalities, including excessively branched and/or coiled glands. Similar criteria were used to diagnose eosinophilic duodenitis (ED), eosinophilic jejunitis (EJ), and eosinophilic colitis (EC). Eosinophilic esophagitis (EoE) was diagnosed if at least 15 eosinophils were found per high power field (Furuta, G. et al. *Gastroenterology* 133:1342-63 (2007)).

EG patients who met entry criteria were identified in the Cincinnati Center for Eosinophilic Disorders (CCED) database. Controls were identified in the CCED database as patients without eosinophilic GI disease who otherwise met entry criteria and who were matched for age and sex to the EG patients. Clinical information was obtained from the CCED database and review of medical records.

Example 2

Histopathology and Genetic and Molecular Analysis

Biopsy Preparation

Samples were obtained at the incident endoscopy from the duodenum, stomach, and esophagus of all patients. Some patients also had colonoscopy. Biopsies for histologic evaluation were fixed in 10% formalin, routinely processed, and embedded in paraffin. Sections were cut at 5 microns thickness and stained with hematoxylin and eosin or antibody. Alcian blue/PAS stain (Polyscientific, Bay Shore, N.Y.) was also performed on all biopsies.

Immunohistochemistry

Antibody information is provided in Table 1. The antibodies used for immunohistochemical staining in this study, their source, the dilution at which they were used, and the antigen retrieval method applied to the tissue sections are listed. Immunohistochemical stains were performed using a Ventana Benchmark XT automated immunostainer (Ventana, Tucson, Ariz.).

Quantitative Microscopy

Multiple levels of gastric biopsies were surveyed, the area containing the greatest concentration of eosinophils was identified, and eosinophils were counted at 400× (0.3 mm$^2$) to generate a peak eosinophil count. A peak eosinophil count was also obtained for biopsies from other sites in the GI tract if eosinophils appeared excessive. In a similar manner, cells that stained with antibodies were counted at 400× magnification in the area showing the greatest concentration of stained cells. If possible, quantitative evaluations were performed in well-oriented areas.

Microarray Analyses

Gastric antrum samples collected during the incident endoscopy were stored in RNAlater until subjected to RNA isolation using the miRNeasy kit (Qiagen, Valencia, Calif.), per the manufacturer's instructions. Hybridization to DNA microarray using the GeneChip Human Genome U133 Plus 2.0 Array (Agilent, Santa Clara, Calif.) was performed by the Microarray Core at Cincinnati Children's Hospital Medical Center (CCHMC).

Quantitative PCR

Total RNA was isolated from biopsy specimens using the miRNeasy kit (Qiagen), per the manufacturer's suggested procedure. Total RNA was isolated from cells using Trizol (Invitrogen, Carlsbad, Calif.), per the manufacturer's protocol. Total RNA (100 ng-1 μg) was used to synthesize cDNA using Superscript IT Reverse Transcriptase (Invitrogen) using the protocol suggested by the manufacturer. Real-time (RT-) PCR was performed using the IQ5 system (Biorad, Hercules, Calif.). Reactions were carried out using SYBR green mix (BioRad). The value obtained for each primer set was normalized to the GAPDH value for the corresponding sample. Primer sequences (SEQ ID NOS: 105-126) used in the RT-PCR studies are listed in Table 2.

Constructs pCDNA3.1 (−) was obtained from Promega (Madison, Wis.). Expression plasmids were constructed by PCR amplification of the relevant open reading frame using primers (SEQ ID NOS: 127-138) listed in Table 3. The following primers were used: pCDH26-HA: 4177 and 4242 (SEQ ID NOS: 127 and 130), pCDH26-MYC: 4177 and 4241 (SEQ ID NOS: 127 and 129), pCDH26: 4177 and 4178 (SEQ ID NOS: 127 and 128), pHA-CTNNB1: 4590 and 4367 (SEQ ID NOS: 134 and 132), pCTNNB1-HA: 4366 and 4593 (SEQ ID NOS:131 and 135), pCTNNA1-HA: 4370 and 4701 (SEQ ID NOS: 133 and 136), pCTNND1: 4468 and 4469 (SEQ ID NOS: 137 and 138). PCR products were then ligated into the following restriction sites of pCDNA3.1 (−): pCDH26-HA: EcoRI/KpnI, pCDH26-MYC: EcoRI/KpnI, pCDH26: EcoRI/NotI, pHA-CTNNB 1 :XbaI/KpnI, pCTNNB 1-HA: XbaI/KpnI, pCTNNA1-HA: EcoRI/KpnI, pCTNND1:EcoRI/KpnI. pMIRNA1-puro-control has been described previously (Lu, et al., 2012). pMIRNA1-puro-CDH26 was made by introducing the CDH26 open reading frame into the EcoRI and NotI sites of pMIRNA1-puro-control.

Immunofluorescence Microscopy

TE-7 cells, NCI-N87 cells, or HEK 293T cells were grown on glass coverslips. Cells were fixed in ice-cold acetone for 10 minutes, incubated in blocking buffer (PBS, 1% saponin, 3% FBS), and then incubated with either primary antibody or an equal concentration of control antibody in blocking buffer: CDH26, 0.06 μg/ml (Sigma-Aldrich, St. Louis, Mo.); control, normal rabbit IgG (R & D Systems, Minneapolis, Minn.). Sections were incubated with Alexa 594-conjugated secondary antibody (1:250) (Invitrogen). Sections were washed 3 times with PBS after each antibody incubation. Fluromount G containing DAPI was used for mounting. Sections were visualized using the BX51 microscope, DP72 camera, and DP2-BSW imaging software (Olympus America Inc., Center Valley, Pa.).

TABLE 1

Immunohistochemical antibody information.

| Antibody | Vendor | Dilution | Antigen retrieval |
|---|---|---|---|
| Cadherin-like 26 | Sigma-Aldrich St. Louis, MO | 1:50 | EDTA, 30 min |
| MIB-1 | Ventana Medical Systems, Inc Tucson, AZ | Pre-dilute | EDTA, 30 min |
| CD117, c-kit | Cell Marque Corp Rocklin, CA | Pre-dilute | EDTA, 30 min |
| Tryptase | Ventana Medical Systems, Inc Tucson, AZ | Pre-dilute | None |
| IL-13 | Gene Tex, Inc Irvine, CA | 1:25 | None |
| FOXP3 | Abcam Inc. Cambridge, MA | 1:200 | EDTA, 30 min |
| Helicobacter pylori | Ventana Medical Systems, Inc Tucson, AZ | Pre-dilute | EDTA, 30 min |

TABLE 2

RT-PCR primers.

| Transcript | Forward Primer (5' to 3') | Reverse Primer (5' to 3') | SEQ ID NO | Reference |
|---|---|---|---|---|
| GAPDH | TGGAAATCCCATCACCATCT | GTCTTCTGGGTGGCAGTGAT | 105, 106 | * |
| CDH26 | TGCTTTTTCTGTTGCGATGCT | CTTGCCATAACCCCAGCTC | 107, 108 | This Study |
| IL-4 | ACATCTTTGCTGCCTCCAA | AGGCAGCGAGTGTCCTTCT | 109, 110 | ** |
| IL-5 | GCTTCTGCATTTGAGTTTGCTAGCT | TGGCCGTCAATGTATTTCTTTATTAAG | 111, 112 | *** |

TABLE 2-continued

RT-PCR primers.

| Transcript | Forward Primer (5' to 3') | Reverse Primer (5' to 3') | SEQ ID NO | Reference |
|---|---|---|---|---|
| IL-13 | ACAGCCCTCAGGGAGCTCAT | TCAGGTTGATGCTCCATACCAT | 113, 114 | ** |
| IFN-gamma | GTTTTGGGTTCTCTTGGCTGTTA | AAAAGAGTTCCATTATCCGCTACATC | 115, 116 | **** |
| TNF-alpha | CCCCAGGGACCTCTCTCTAATC | GGTTTGCTACAACATGGGCTACA | 117, 118 | **** |
| IL-17A | AATCTCCACCGCAATGAGGA | ACGTTCCCATCAGCGTTGA | 119, 120 | ***** |
| IL-17F | TGCCAGGAGGTAGTATGAAGCTT | ATGCAGCCCAAGTTCCTACACT | 121, 122 | ****** |
| IL-25 | TGAAGTGCTGTCTGGAGCAG | TCCTCAGAATCATCCATGTC | 123, 124 | ******* |
| IL-33 | CACCCCTCAAATGAATCAGG | GGAGCTCCACAGAGTGTTCC | 125, 126 | ******** |

*Blanchard, C. et al. J. Clin. Invest. 116:536-47 (2006),
**Vicario, M. et al. Gut 59:12-20 (2010),
***Ehlers, S. et al. J. Exp. Med. 173:25-36 (1991),
****Boeuf, P. et al. BMC Immunol. 6:5 (2005),
*****Bulens, D. et al. Respir. Res. 7:135 (2006),
******Yang, J. et al. Arthritis Rheum, 60:1472-83 (2009),
*******Hwang and Kim Mol. Cells 19:180-4 (2005),
********Carriere, V. et al. Proc. Natl. Acad. Sci. U.S.A. 104:282-7 (2007)

TABLE 3

Primers used to generate expression constructs.

| Primer Designation | Primer (5' to 3') | SEQ ID NO |
|---|---|---|
| 4177 | GGAATTCACCATGGCCATGAGATCCGGGAGG | 127 |
| 4178 | ATAAGAATGCGGCCGCTTAGGAAGGAACACCTGACT | 128 |
| 4241 | GGGGTACCTTACAGGTCCTCCTCGCTGATCAGCTTCTGCTCGGAAGGAACACCTGACT | 129 |
| 4242 | GGGGTACCTTAGGCGTAGTCGGGCACGTCGTAGGGGTAGGAAGGAACACCTGACT | 130 |
| 4366 | GCTCTAGACACCATGGCTACTCAAGCTGATTTG | 131 |
| 4367 | GGGGTACCTTACAGGTCAGTATCAAACC | 132 |
| 4370 | GGAATTCACCATGACTGCTGTCCATGCAGG | 133 |
| 4590 | GCTCTAGACACCATGTACCCCTACGACGTGCCCGACTACGCCGCTACTCAAGCTGATTTG | 134 |
| 4593 | GGGGTACCTTAGGCGTAGTCGGGCACGTCGTAGGGGTACAGGTCAGTATCAAACC | 135 |
| 4701 | GGGGTACCTTAGGCGTAGTCGGGCACGTCGTAGGGGTAGATGCTGTCCATAGCTTTG | 136 |
| 4468 | GGAATTCACCATGGACGACTCAGAGGTGG | 137 |
| 4469 | GGGGTACCCTAAATCTTCTGCATGGAGG | 138 |

Example 3

Cell Culture and Treatment

Culture of Primary Esophageal Epithelial Cells

A sample of distal esophageal epithelium was collected during incident or other endoscopy. Following digestion with trypsin/EDTA, biopsy samples were cultured in modified F-media (3:1 F-12/Dulbecco modified Eagle's medium) supplemented with FBS (5%), adenine (24.2 µg/ml), cholera toxin (10-4 µmol/L), insulin (5 µg/ml), hydrocortisone (0.4 µg/ml), and epidermal growth factor (10 ng/ml) in the presence of penicillin, streptomycin, and amphotericin (Invitrogen). Cultures were supplemented with 1 to 5×10$^5$ feeders (NIH 3T3 J2 cells irradiated 6000 rad). Media were changed twice weekly. Upon reaching confluency, cells were trypsinized and re-plated for experiments.

Culture of Cell Lines and Cytokine Treatment

Cells from human esophageal cell line TE-7 (IARC, Lyon, France) were maintained in RPMI medium (Invitrogen) supplemented with 5% FBS (Atlanta Biologicals, Lawrenceville, Ga.) and 1% penicillin/streptomycin (Invitrogen). HEK 293T cells were grown in DMEM medium (Invitrogen) supplemented with 10% FBS (Atlanta Biologicals) and 1% penicillin/streptomycin (Invitrogen). NCI-N87 cells were obtained from ATCC (Manassas, Va.) and cultured in RPMI medium (Invitrogen) supplemented with 10% FBS (Atlanta Biologicals) and 1% penicillin/streptomycin (Invitrogen). IL-13 (Peprotech, Rocky Hill, N.J.) was added to culture media at 10 or 100 ng/ml for 24 or 48 hours.

Example 4

Protein Analyses

Protein Extracts and Immunoprecipitation

To confirm and complement microscopic studies of biopsy samples using antibodies, additional analyses of protein expression were performed. For immunoprecipitation, cell lysates were prepared from HEK 293T cells generally, as previously described (Klingelhofer, J. et al. Mol. Cell Biol. 22:7449-58 (2002)). Cells (approximately 2×10$^6$) were washed one time with PBS and incubated in IP buffer (50 mM Tris-HCl (pH 7.4), 150 mM NaCl, 2 mM EDTA, 1 mM dithiothreitol, 1% Nonidet P-40 (NP-40), 20 µM phenylmethylsulfonyl fluoride) for 10 minutes on ice. Cells were scraped from the plate and rotated at 4° C. for 10 minutes. Lysates were cleared by centrifugation at 20,000×g at 4° C. for 10 minutes. An equal amount of protein was added to total 500 µl of IP buffer plus protease inhibitors (Roche, Indianapolis, Ind.). Antibodies (2 µg each for either α-HA (Covance, Princeton, N.J.), α-myc (Cell Signaling Technology, Danvers, Mass.), α-p120 (BD Transduction Laboratories, Lexington, Ky.), or mouse IgG 1 control (AbD Serotec, Raleigh, N.C.)) were added to the lysates and rotated overnight at 4° C. Subsequently, 20 µl of protein A/G agarose beads (Santa Cruz Biotechnology, Inc., Santa Cruz, Calif.) were added per sample. After 2 hours of rotation at 4° C., beads and immunoprecipitates were washed 5 times in IP buffer containing protease inhibitors. 2× Laemmli buffer was added to the immunoprecipitates or total cell lysates saved prior to IP (input) prior to SDS-PAGE analysis, as described below.

Western Blot Analyses

Total protein (5-10 µg for TE-7 and primary esophageal epithelial cells), inputs, or inmmunoprecipitates (as described above) were loaded onto 4-12% NuPage Tris-bis gels (Invitrogen), electrophoresed for 1.5 hours at 150 V, and transferred to nitrocellulose membranes, followed by western blot analysis. Primary antibodies were diluted in TBS/0.1% Tween 20 containing 5% milk in the following proportions: rabbit anti-CDH26 (Sigma-Aldrich), 1:500; rabbit anti-Beta-catenin (Cell Signaling Technology, Inc., Danvers, Mass.); mouse anti-HA (Covance), 1:1000; mouse anti-myc (Cell Signaling Technology, Inc.), 1:1000; mouse anti-beta-actin (Sigma-Aldrich), 1:5000. Secondary antibodies were incubated with the membranes in the following proportions: anti-goat HRP, 1:10,000 (Jackson ImmunoResearch Laboratories, Inc., West Grove, Pa.); anti-rabbit HRP, 1:10,000 (Cell Signaling Technology, Inc.); anti-mouse HRP, 1:10,000 (Cell Signaling Technology, Inc.). Blots were developed using ECL Plus reagent (GE Healthcare, Piscataway, N.J.). Densitometry measurements were performed using Multi Gauge V3.0 (Fujifilm, Japan).

Protein Extracts from Esophageal and Gastric Tissue

Biopsy samples collected from the distal esophagus or the gastric antrum samples designated for protein isolation were stored in RNAlater at −80° C. prior to protein isolation. Tissue was transferred into 100 µl of IP buffer (50 mM Tris-HCl (pH 7.4), 150 mM NaCl, 2 mM EDTA, 1 mM dithiothreitol, 1% Nonidet P-40 (NP-40), 20 µM phenylmethylsulfonyl fluoride) and sonicated. The lysates were cleared and soluble lysates were subjected to protein quantitation by BCA assay, and the indicated quantity of protein was subjected to SDS-PAGE and western blot analysis, as described above. Alternatively, protein was isolated from the organic fraction remaining after isolation of RNA using the miRNeasy kit to isolate RNA from biopsy specimens. Briefly, DNA was precipitated by the addition of 0.3 volumes of 100% ethanol followed by spin at 2,000×g. Protein was then precipitated from the supernatant by the addition of 3 volumes of acetone. Precipitated protein was pelleted by centrifugation at 20,000×g for 10 minutes at 4° C., dried, and solubilized in 2× Laemmli buffer. Solubilized proteins were subjected to SDS-PAGE and western blot analysis, as described above.

Example 5

Analysis of Protein Localization

Lentivirus Production and Transduction of TE-7, NCI-N87, and HEK 293T Cells

Lentivirus production was carried out by the Cincinnati Children's Hospital Viral Vector Core (CCHMC). TE-7, NCI-N87, or HEK 293T cells were transduced by incubating lentivirus with the cells for 24 hours in the presence of 5 µg/ml polybrene. Media were then changed, and media containing 2 µg/ml puromycin was added after 24 hours. After selection for 48 hours in puromycin, cells were dispersed and plated to single cells in 96-well plates to obtain clones derived from single cells. A second round of dispersing, plating to single cells, and picking single colonies was performed. CDH26 expression was verified by western blot analysis and, in some cases, FACS analysis.

FACS Analysis

HEK 293T cells clones transduced with either pMIRNA1-puro-control or pMIRNA1-puro-CDH26 were dispersed by EDTA treatment and then either fixed with 2% formaldehyde in FACS buffer (0.5% BSA, 0.01% NaN$_3$ in 1×HBSS) or subjected to staining using BD cytofix/cytoperm reagents (BD Biosciences) according to the manufacturer's protocol. Cells were stained with antibody specific for CDH26 (0.12 µg antibody/50 µl FACS buffer) (Sigma Prestige) or an equivalent amount of normal rabbit IgG as a control. Cells were then incubated with secondary antibody (anti-rabbit Alexa 647) (Invitrogen). Flow cytometry analysis was performed using the FACSCalibur (BD), and analysis was performed using FlowJo software (TreeStar, Ashland, Oreg.).

Biotinylation of Cell Surface Proteins

Adherent cells were washed with ice-cold biotinylation buffer (100 mM HEPES, 50 mM NaCl, pH 8.0) twice before addition of cold biotinylation buffer plus sulfo-NHS-LC-biotin (concentration 9.259 mg/ml) (Thermo Scientific). Cells were incubated on ice for 30 minutes. The buffer was removed, and the cells were washed 3 times with ice cold PBS+100 mM glycine. Protein was then extracted as described above using IP buffer plus protease inhibitors (Klingelhofer, J. et al. *Mol. Cell Biol.* 22:7449-58 (2002)). Cell lysates were incubated with streptavidin-agarose beads (Sigma-Aldrich) for 2 hours at 4° C. Beads and precipitates were washed 5 times with cold IP buffer containing 20 mM PMSF. The beads were then boiled for 5 minutes (100° C.) in 2× Laemmli buffer, and the solubilized proteins were subjected to SDS PAGE and western blot analyses as described above.

Eosinophil Isolation

One part 4.5% Dextran in PBS was added to 5 parts peripheral blood collected from normal donors. Leukocyte-rich plasma was applied to a Percoll gradient (1.5 ml 10×HBSS, 9.5 ml Percoll, 4.5 ml H$_2$O) and spun at 1300 rpm (500×g) for 30 minutes. Granulocytes were collected and red blood cells were lysed by hypotonic lysis. Granulocytes were incubated with anti-CD16 MACS microbeads (Miltenyi Biotec) (1 µl per 1×10$^6$ cells) for 30 minutes at 4° C. Cells were then applied to a MACS column, and eosinophils were eluted. Eosinophil purity was confirmed by cytospin and DiffQuick staining and was routinely >95%, and viability was >98%, as assessed by trypan blue exclusion. Eosinophils were resuspended at a density of 1×10$^6$ cells/ml in RPMI+10% FBS+1% penicillin/streptomycin and cultured at 37° C. until they were used in transmigration assays or for protein isolation.

Eosinophil Transmigration Assay

HEK293T cells transduced with either pMIRNA1-puro-control or pMIRNA1-puro-CDH26 as described above were plated on transwell inserts (polycarbonate, 6.5 mm diameter, 0.3 µm pore size) (Costar, Tewksbury, Mass.). Eosinophils (1.3×10$^5$ at a density of 1×10$^6$ cells/ml suspended in 1×HBSS plus 1 mM CaCl$_2$ plus 2% FBS) were applied to the top of the transwell, while the bottom chamber of the transwell contained 1×HBSS plus 1 mM CaCl2 plus 2% FBS and the indicated concentration of chemoattractant (human eotaxin-1, Peprotech). Reactions were incubated at 37° C. for 1.5 hours. The transwells were then subjected to Wright-Giemsa staining per the manufacturer's protocol (Harleco, EMD Millipore, Billerica, Mass.) to confirm the confluence of the cells. The number of eosinophils present in the lower chambers was then assessed by counting the cells using a Hemacytometer (Sigma-Aldrich).

Statistical Analyses

Intergroup comparisons of the numbers of eosinophils and immunoreactive cells in gastric biopsies were made using Student's t test, and significance was set at P <0.05. For microarray analyses, gene transcript levels were determined, and statistical analyses were performed using algorithms in GeneSpring GX v7.3 software (Agilent). For RT-PCR comparisons, the Mann-Whitney test was used.

Example 6

Characterization of EG Patients and Disease Manifestations

History of Atopic Disease in EG Patients

Information corresponding to each patient involved in the gastric tissue microarray study is listed in Table 4. Indication for the index endoscopy is listed, as well as the macroscopic findings observed during the index endoscopy. Diagnosis derived from the index endoscopy is shown, and any EGID diagnosis that was assigned prior to the index endoscopy is also listed. Duration of EG indicates the amount of time elapsed between the initial diagnosis of EG and the index endoscopy. Medications at index endoscopy indicate the medications that the patient was prescribed during the time period immediately prior to the index endoscopy. Diet at index endoscopy lists the diet that the patient was prescribed during the time period immediately prior to the index endoscopy.

There were 4 females and 1 male in the EG and control groups (Table 4). The mean age of EG patients was 12.6±6.2 (range 3-20) years; the mean age of controls was 9±7.3 (range 1-15) years, not significantly different from EG patients.

Table 5 includes patient atopic history, including whether a patient has a history of the indicated condition, if known. This information was self-reported by the patient or his/her parent. Patient numbers correspond to those listed in Table 4.

Four patients in each group reported histories of allergy (Table 5). One EG patient reported anaphylaxis to food (#2); none of the EG or control patients reported anaphylaxis to non-food. One patient in each group reported a history of asthma, and 1 of these patients (#2) was treated with inhaled flovent. Four EG patients were evaluated with skin prick tests that were positive in 2 patients. One EG patient (#1) had skin prick tests that were reportedly positive performed prior to referral to the CCED. Two EG patients (#1, #2) had multiple positive radioallergosorbent (RAST) tests. One control patient (#6) was a sibling of a patient with EoE.

Elevated Levels of Blood Eosinophils in EG

Results of laboratory tests performed on peripheral blood obtained the day of the endoscopy or the most proximal blood sample to the day of the biopsy are listed in Table 6. Complete blood counts were obtained from all 10 patients, and the absolute eosinophil count was increased in all EG patients but not in any of the control patients (Table 6). Additional tests included lack of ova and parasites in stool samples from 3 EG (#1, #3, #5) and from 1 control patient (#8). Plasma eosinophil cationic protein was measured in one EG patient (#1), and it was found to be elevated (314 ng/ml; normal <31.2 ng/ml).

Correlation of Gross Mucosal Appearances with Histological Diagnoses

Gastric mucosal nodularity was reported in 4 of 5 EG patients (Table 4). A small hyperplastic polyp was found at the incisura in one EG patient (#4). White plaques or patches and thickened mucosa were found in the esophagi of 3 EG patients who also had EE. *Nodular mucosa* in the jejunum was described in the EG patient who had active EJ. The *mucosa* appeared normal in all control patients. Indications for the incident endoscopy are listed in Table 4.

Chronic Nature of EG and Frequent Association with other EGIDs

At the incident endoscopy, all 5 EG patients had active EG. EG patients had between 1 and 7 prior endoscopies, and 4 of 5 EG patients had prior gastric biopsies that showed active EG (Table 4).

Four EG patients had eosinophilic inflammation in other sites in the GI tract in addition to the stomach at incident endoscopy and prior endoscopies (Table 4). Three of the EG patients had EE in addition to EG at index endoscopy.

None of the control patients had eosinophilic inflammation in their GI biopsies, and all their biopsies were considered non-diagnostic. Control patients did not have any GI endoscopies other than the incident procedure. The incident endoscopic procedure included colonoscopy in two EG (#1, #3) and 2 control (#8, #9) patients that yielded normal biopsies in all 4 patients.

Treatment at Index Endoscopy

Medications for all patients that were listed in the clinical record at the time of the index endoscopy are shown in Table 4. Fluticasone propionate, both inhaled and swallowed, was prescribed for 1 EG patient who had asthma and EoE diagnosed prior to the index endoscopy. Two EG patients followed an elimination diet at the time of incident endoscopy, and 3 patients had no dietary restrictions.

TABLE 4

Index endoseopy information.

| Patient | Age (yrs)/Sex | Indication | Endoscopic findings | Dx | Prior EGID Dx | Duration of EG | Med at IE | Diet at IE |
|---|---|---|---|---|---|---|---|---|
| 1 EG | 3/F | Duodenal mass | Antrum and jejunum: nodules | EG, EJ | EG, ED | 2.5 mos | Ferrous sulfate | Ad lib |
| 2 EG | 20/F | Abdominal pain | Esophagus: thickened mucosa. Antrum: erythema. | EG, EoE | EoE | None | Flovent, Protonix | Elim |
| 3 EG | 15/F | Diarrhea | Esophagus: white plaques; Antrum: nodules | EG, EoE | EG | 8.5 mos | Iron, vitamins, probiotics | Elim |
| 4 EG | 13/M | Med change | Fundus and body: nodules Antrum: normal | EG | EG | 1.4 years | MTX, folic acid, prevacid | Ad lib |
| 5 EG | 12/F | Med change | Esophagus: white patches; Stomach: peristomal nodules | EG, EoE | EG, EoE, EJ | 5 years | Beclo, 6 MP, growth hormone, lamisil | Ad lib |

TABLE 4-continued

Index endoscopy information.

| Patient | Age (yrs)/Sex | Indication | Endoscopic findings | Dx | Prior EGID Dx | Duration of EG | Med at IE | Diet at IE |
|---|---|---|---|---|---|---|---|---|
| 6 Con | 1/F | Vomiting, siblings with EoE | Normal | NDA | None | None | Prevacid | Unk |
| 7 Con | 14/F | Abdominal pain, ITP | Normal | NDA | None | None | Prilosec | Ad lib |
| 8 Con | 14/F | Chronic abdominal pain | Normal | NDA | None | None | Bactroban | Ad lib |
| 9 Con | 15/M | Rectal bleeding | Normal | NDA | None | None | Miralax | Ad lib |
| 10 Con | 1/F | Daily spit ups | Normal | NDA | None | None | Prevacid, hydrocortisone cream | Ad lib |

Yrs, years;
Dx, diagnosis;
EGID, eosinophilic gastrointestinal disease;
EG, eosinophilic gastritis;
Med, medication;
IE, incident endoscopy;
F, female;
M, male;
EJ, eosinophilic jejunitis;
ED, eosinophilic duodenitis;
EoE, eosinophilic esophagitis;
Elim, elimination diet;
mos, months;
MTX, methotrexate;
Beclo, beclomethasone;
6-MP, 6 mercaptopurine;
NDA, no diagnostic abnormality;
Unk, unknown;
ITP, idiopathic thrombocytopenic purpura.

TABLE 5

Atopic history.

| Patient | Asthma | AC | AR | HF | U/A | Eczema | Drug allergy | Food allergy | E allergy | Skin prick tests |
|---|---|---|---|---|---|---|---|---|---|---|
| 1 EG | Unk | Unk | Unk | Unk | Unk | Unk | Unk | Yes | Unk | |
| 2 EG | Yes | Yes | Yes | Yes | Yes | Yes | Yes | Yes | Yes | F, E |
| 3 EG | No | Yes | Yes | No | No | No | Yes | Yes | Yes | F, E |
| 4 EG | No | No | No | No | No | No | No | No | No | Neg |
| 5 EG | Unk | No | No | No | No | Unk | Unk | Yes | Yes | Neg |
| 6 Con | No | No | No | No | No | No | No | Yes | Yes | |
| 7 Con | Yes | No | No | No | No | No | No | Yes | Yes | |
| 8 Con | No | No | Yes | Yes | No | No | No | Yes | Yes | |
| 9 Con | No | No | No | No | No | No | No | No | No | |
| 10 Con | No | No | No | No | Yes | No | No | Unk | Unk | |

AC, allergic conjunctivitis;
AR, allergic rhinitis;
HF, hay fever;
U/A, urticaria/angioedema;
E, environmental;
EG, eosinophilic gastritis;
Unk, unknown;
F, food;
Con, control.

TABLE 6

Laboratory findings.

| Patient | Peripheral eosinophil count (K/μL) (%) | Plasma IL-2 (pg/ml) (normal) | Plasma IL-5 (pg/ml) (normal) | Plasma γ-Interferon (pg/ml) (normal) | IgE (mg/dl) (normal) | CRP | Clo |
|---|---|---|---|---|---|---|---|
| 1 EG | 3.07 (21%) | 24 (<18) | 9 (<24) | | | Nl | Neg |
| 2 EG | 1.22 (19%) | | | | 62 (<114) | Nl | Neg |
| 3 EG | 2.42 (35%) | | | | 100 (<114) | Nl | Neg |
| 4 EG | 0.65 (9%) | <6 (<18) | 27 (<24) | 82 (<68) | | Nl | |

TABLE 6-continued

Laboratory findings.

| Patient | Peripheral eosinophil count (K/μL) (%) | Plasma IL-2 (pg/ml) (normal) | Plasma IL-5 (pg/ml) (normal) | Plasma γ-Interferon (pg/ml) (normal) | IgE (mg/dl) (normal) | CRP | Clo |
|---|---|---|---|---|---|---|---|
| 5 EG | *0.31 (8%)* | | | | | Nl | Neg |
| 6 Con | 0 (0%) | | | | | | Neg |
| 7 Con | 0.09 (1%) | <6 (<18) | 3 (<39) | <5 (<154) | | | Neg |
| 8 Con | 0.07 (1%) | | | | | Nl | Neg |
| 9 Con | 0.12 (1%) | | | | | Nl | Neg |
| 10 Con | 0.17 (2%) | | | | 2 (<53) | | |

CRP, C-reactive protein;
Clo, campylobacter-like organism test/rapid urease test;
Nl, normal;
Neg, negative.
Abnormal values are italicized;
CRP and Clo tests were normal for all patients.

Example 7

Gastric Biopsy Histopathology

Marked Eosinophilic Inflammation

Table 7 shows the quantitative evaluation of inflammatory and epithelial cells. Data numbers represent peak counts/hpf for eosinophils, and cells were stained with the antibodies indicated at the head of each column. Mean eosinophil number is defined as the mean of peak eosinophil count/hpf in samples from body/antrum or antrum that were used for the immunohistochemical stains in the table.

Table 8 shows characteristics for the biopsy specimens of five patients with active EG. Patient numbers correspond to those in Table 4. The number of biopsy specimen pieces that were diagnostic of EG is compared to the total number of pieces obtained per patient per anatomical site in the third column. The fourth and fifth columns denote the number of eosinophils present per hpf in the field that exhibited the highest eosinophil count for the antral and fundic mucosa specimens, respectively. Peak eosinophil counts for antral vs. fundic mucosa were subjected to T-test, and the p-value was >0.05. The mean +/−SD for the highest peak eosinophil count (antral or fundic mucosa) was also calculated.

Gastric biopsies from all EG patients showed active eosinophilic disease, with markedly increased numbers of eosinophils (Table 7, FIG. 1A). The mean and standard deviation values for the highest peak eosinophil counts in EG biopsies, including biopsies submitted in addition to those from antrum or antrum/body (Table 8), was 355±214 eosinophils/hpf (range 122-603 eosinophils/hpf), compared to 10.6±7.1 eosinophils/hpf (range 3-21 eosinophils/hpf) in controls (P <0.05). The mean of the peak eosinophil counts in antral-type mucosa was similar to that in fundic-type mucosa.

Although the number of eosinophils did not differ according to the type of gastric mucosa, in all cases, eosinophilic inflammation was non-uniform, varying among and even within pieces. The percent of pieces that were diagnostic for EG ranged from 20-100% in a submitted sample (Table 8).

In addition to showing variations in quantity of eosinophils, in EG biopsies, the distribution of eosinophils within pieces was different compared to controls. Eosinophils in EG biopsies spanned the depth of the mucosa and often appeared concentrated in superficial lamina propria. In contrast, eosinophils in control biopsies were confined to the deep lamina propria. Numerous intraepithelial eosinophils were observed in glands in EG biopsies but not in controls. Submucosa was present in 3 EG biopsies, and submucosal eosinophils were observed but were fewer than in the lamina propria. Submucosa was present in one control biopsy, but submucosal eosinophils were not seen.

Correlation of Peak Eosinophil Counts with Peripheral Blood Eosinophil Counts

Figure 1B:
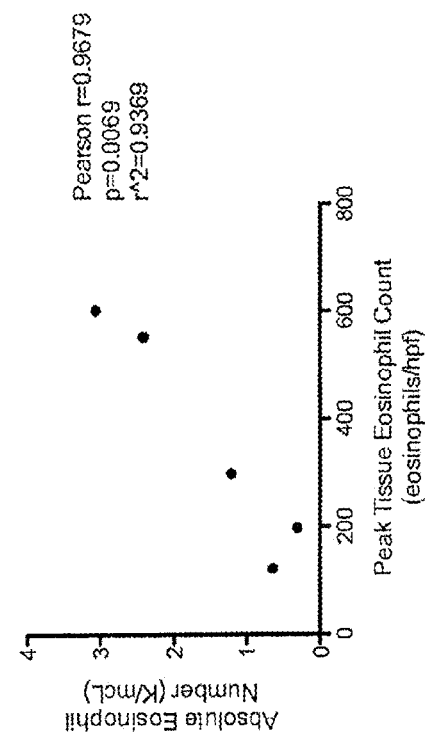
Figure 1C:
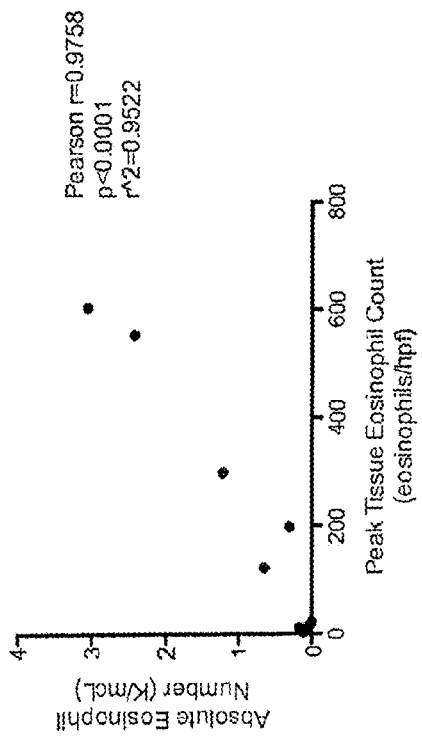

The highest peak eosinophil counts in EG biopsies correlated significantly with absolute eosinophil counts in peripheral blood (FIGS. 1B-1C). The significant correlation remained after cases in which the blood sample had not been obtained at the time of index endoscopy were removed from the analysis. Tissue eosinophil counts did not correlate with blood eosinophil counts in control patients.

EG Pathology in Addition to Eosinophilic Inflammation

Architectural changes in EG biopsies included elongated and excessively branched or coiled glands. In contrast to controls, lamina propria fibrosis was seen in 3 EG cases. In areas in which eosinophils were not numerous in EG biopsies, chronic inflammation was sometimes seen, including numerous plasma cells. In one EG case, few acute inflammatory cells were seen in the epithelium of few glands. *Helicobacter pylori* organisms were not seen in biopsies from either group in H&E stains or in sections stained with antibody to the organisms. Intestinal metaplasia was not seen in any of the EG biopsies, as corroborated with Alcian blue/PAS stain. Intestinal metaplasia was seen in one control biopsy (#8).

Increased Cell Proliferation

The mucosa in EG biopsies was not atrophic and indeed often appeared thickened with elongated glands. Therefore, a study was designed to identify whether increased cell proliferation is present in EG.

Epithelial cells and lamina propria cells in both EG and control biopsies were stained with MIB1 antibody, which is a marker of cell proliferation that decorates nuclei in all phases of the cell cycle except G0. Lamina propria cells that stained included cells in lymphoid aggregates; lamina propria cells near lymphoid aggregates were not included in quantitative evaluations since lymphoid aggregates were not present in all cases.

Figure 2:
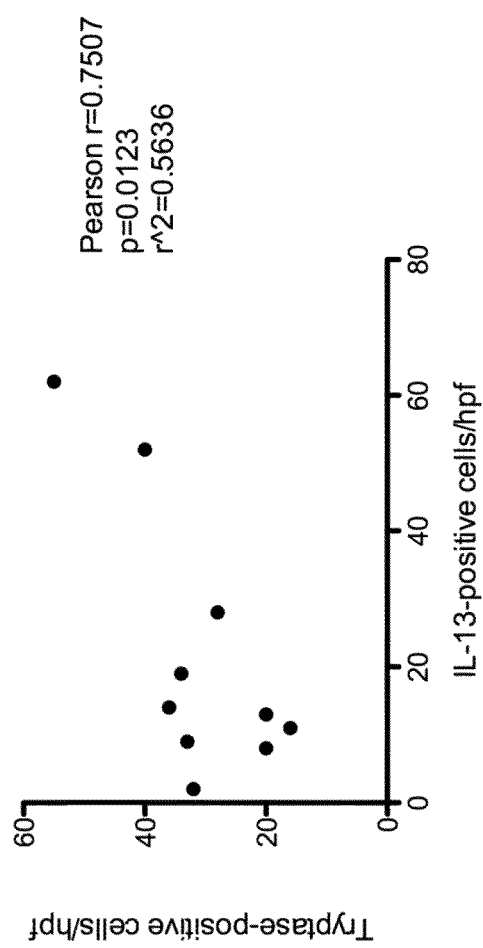
FIG. 2 depicts the quantification and correlation of tryptase- and IL-13-expressing cells in inflamed gastric tissue.

The number of epithelial and lamina propria cells that stained with MIB1 antibody was greater in EG compared to control biopsies (Table 7). The pattern of epithelial cell staining was remarkably altered in the EG biopsies. In several EG cases, there was expansion of the proliferative zone to include continuous staining of surface epithelial cells, a pattern not seen in control cases (FIG. 2). A subsequent study was designed to further characterize the inflammatory infiltrate in EG biopsies using immunohistochemistry.

Involvement of other Inflammatory Cells

Mast cells—The presence of mast cells was assessed in gastric biopsies by using CD117 antibody, which stains the tyrosine kinase receptor c-kit that is normally expressed on the membrane of mast cells, and tryptase antibody, which stains a protease normally found in mast cell granules. In all gastric biopsies, there were significantly more cells that stained with anti-CD117 compared to cells that stained with anti-tryptase: 51±3.8 vs 31.8±7.3, P <0.05 for controls and 93.8±33.1 vs 31±15.5, P <0.05 for EG biopsies (Table 7).

In control biopsies, CD117$^+$ cells and tryptase$^+$ cells were most numerous in lamina propria but were also seen in muscularis mucosa and submucosa. Gastric antrum sections from a biopsy obtained during the index endoscopy were stained to observe CD117 localization. The cells were seen throughout the lamina propria but were usually more numerous in the deep lamina propria. In EG biopsies, cells stained with CD117 or tryptase were seen in the same distribution as in control biopsies but appeared more numerous in the superficial lamina propria compared to controls. In EG biopsies, cells that stained with CD117, but not tryptase, were significantly increased compared to control biopsies (Table 7).

IL-13—In control biopsies, IL-13$^+$ cells appeared most numerous in the deep lamina propria, but they were present throughout the depth of the mucosa in EG biopsies, including the superficial lamina propria. The number of IL-13$^+$ cells in each group was highly variable and there was not a significant difference in the numbers of IL-13$^+$ cells in EG cases compared to controls (Table 7).

and immediately adjacent to lymphoid aggregates. Lymphoid aggregates were seen in 2 EG cases; FOXP3$^+$ cells numbered 36 FOXP3$^+$ cells/hpf and 46 FOXP3$^+$ cells/hpf in and near the aggregates. In the 3 control cases, lymphoid aggregates exhibited 57 FOXP3$^+$ cells/hpf, 0 FOXP3$^+$ cells/hpf, and 6 FOXP3$^+$ cells/hpf. Since lymphoid aggregates were not found in all biopsies, only cells in the lamina propria not associated with lymphoid aggregates were counted. The number of FOXP3$^+$ cells was significantly increased in EG biopsies compared to controls (Table 7).

FIG. 1A. Hematoxylin and eosin-stained gastric antrum biopsy specimens were obtained from the index endoscopy of each patient included in this study (magnification=200× or 400×). Patient numbers correspond to those in the tables and the text.

FIG. 1B. The peak eosinophil count was obtained for the gastric tissue obtained at the index endoscopy for all patients and was correlated with the absolute eosinophil number (K/μL) counted from a blood sample obtained either the same day as the endoscopy or the most proximal time period possible.

FIG. 1C. The peak eosinophil count was obtained for the gastric tissue obtained at the index endoscopy for patients with active EG and was correlated with the absolute eosinophil number (K/μL) counted from a blood sample obtained either the same day as the endoscopy or the most proximal time period possible.

FIG. 2. Quantification and correlation of tryptase- and IL-13-positive cells in gastric antrum tissue are depicted. Gastric antrum sections obtained during the index endoscopy were stained with anti-tryptase or anti-IL-13 antibodies. The numbers of tryptase-positive cells and IL-13-positive cells per high power field were quantified.

TABLE 7

Quantitative evaluation of inflammatory and epithelial cells.

| Patient | Eosinophils | MIB1 epithelium | MIB1 lp | CD117 | Tryptase | IL-13 | FOXP3 | CDH26 |
|---|---|---|---|---|---|---|---|---|
| 1 EG | 567 | 528 | 27 | 82 | 55 | 62 | 11 | 135 |
| 2 EG | 298 | 425 | 103 | 61 | 20 | 8 | 32 | 54 |
| 3 EG | 553 | 558 | 49 | 114 | 28 | 28 | 28 | 241 |
| 4 EG | 79 | 470 | 28 | 71 | 16 | 11 | 7 | 91 |
| 5 EG | 197 | 775 | 121 | 141 | 36 | 14 | 14 | 0 |
| Mean ± SD | 338 ± 216 | 551 ± 135 | 65.6 ± 43.7 | 93.8 ± 33.1 | 31 ± 15.5 | 24.6 ± 22.3 | 18.4 ± 11 | |
| 6 Con | 21 | 190 | 14 | 48 | 40 | 52 | 5 | 0 |
| 7 Con | 13 | 289 | 17 | 53 | 20 | 13 | 1 | 0 |
| 8 Con | 5 | 591 | 10 | 46 | 33 | 9 | 3 | 0 |
| 9 Con | 3 | 135 | 15 | 55 | 34 | 19 | 8 | 0 |
| 10 Con | 11 | 237 | 17 | 53 | 32 | 2 | 4 | 0 |
| Mean ± SD | 10.6 ± 7.1 | 288 ± 178 | 14.6 ± 2.9 | 51 ± 3.8 | 31.8 ± 7.3 | 19 ± 19.5 | 4.2 ± 2.6 | |
| P value | <0.05 | <0.05 | <0.05 | <0.05 | >0.05 | >0.05 | <0.05 | |

Data numbers are peak eosinophil counts/hpf for eosinophils; cells stained with the antibodies are indicated at the head of each column.
Mean eosinophil #, mean of peak eosinophil count/hpf in samples from body/antrum or antrum that were used for the immunohistochemical stains in the table.

The number of IL-13$^+$ cells was found to correlate significantly with the number of tryptase$^+$ mast cells. Gastric antrum sections from a biopsy obtained during the index endoscopy for each patient included in the study were stained to identify cells that expressed tryptase; separate biopsy specimens were stained for IL-13. The number of tryptase-positive cells was then correlated with the number of IL-13-positive cells.

FOXP3—In contrast to eosinophils, mast cells, and IL-13$^+$ cells, FOXP3$^+$ lymphocytes were most numerous in

TABLE 8

Biopsy characteristics.

| Patient | Sample source | Diagnostic #/total # pieces | Antral mucosa Peak eosinophil # | Fondic mucosa Peak eosinophil # |
|---|---|---|---|---|
| 1 EG | Body/antrum* | 2/5 (40%) | 139/hpf | 567/hpf |
| | Antral nodules | 3/4 (75%) | 603/hpf | None |

TABLE 8-continued

Biopsy characteristics.

| Patient | Sample source | Diagnostic #/total # pieces | Antral mucosa Peak eosinophil # | Fondic mucosa Peak eosinophil # |
|---|---|---|---|---|
| 2 EG | Body/antrum* | 2/4 (50%) | 298/hpf | 35/hpf |
| 3 EG | Body/antrum* | 5/5 (100%) | 553/hpf | None |
| 4 EG | Antrum* | 1/2 (50%) | 79/hpf | None |
|  | Body | 2/5 (40%) | 87/hpf | 122/hpf |
| 5 EG | Body/antrum* | 1/5 (20%) | 97/hpf | 197/hpf |
| Mean ± SD Antral vs fundic |  |  | 328 ± 244/hpf | 230 ± 234/hpf |
| P value |  |  | >0.05 | |
| Mean ± SD Highest |  |  | 355 ± 214/hpf | |

, number;
*biopsy used for immunohistochemistry that corresponded to tissue samples used for genetic and molecular analyses;
P value, mean of antral values compared to fundic values.

Example 8

Unique Transcriptome of EG Biopsies

A subsequent study was designed to determine the molecular mechanisms controlling the pathogenesis of EG. Accordingly, RNA isolated from gastric antrum biopsy specimens from EG and control patients was subjected to global transcript analysis.

Figure 3A:
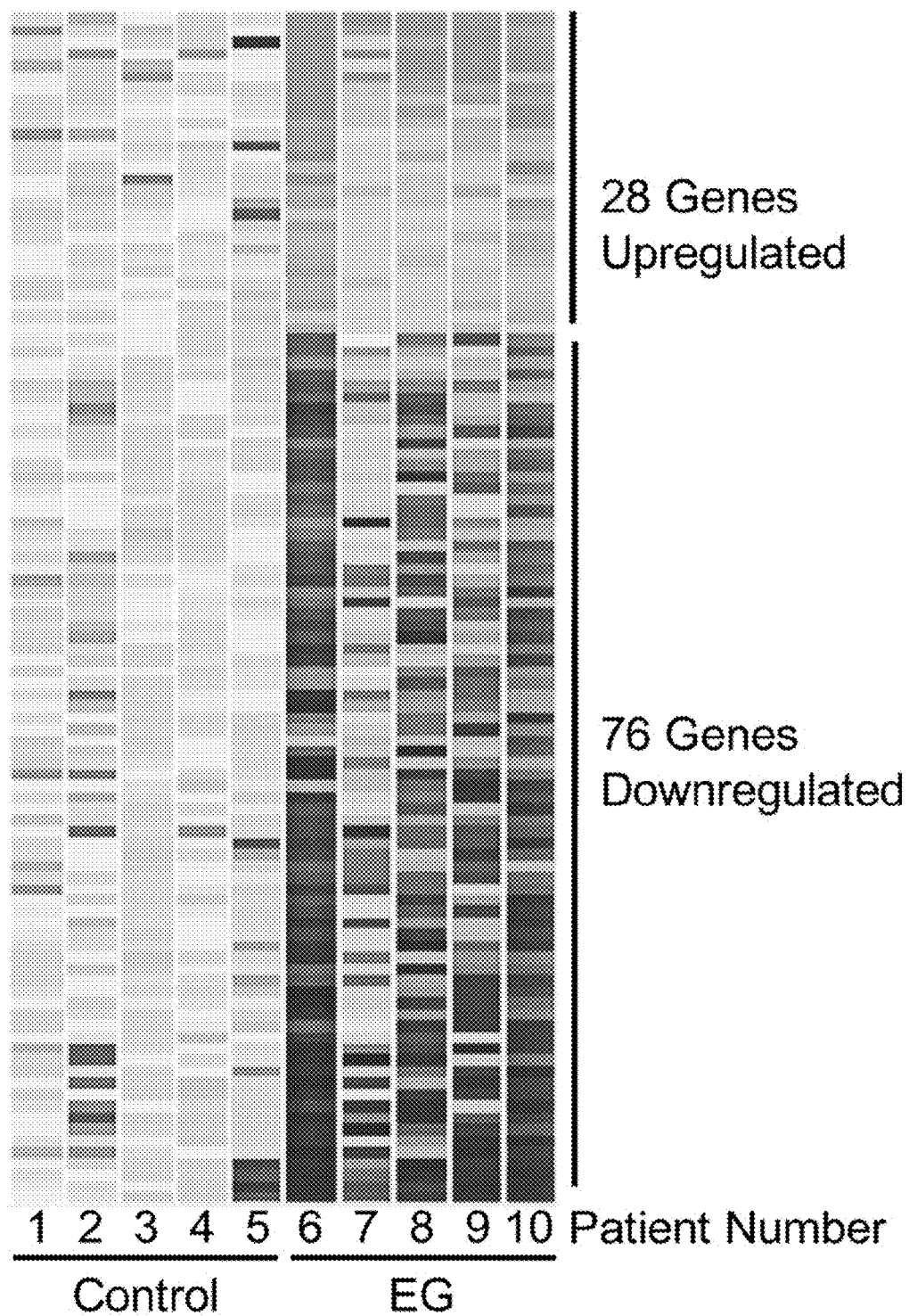
FIGS. 3A-B depict identification of transcripts differentially regulated in the gastric tissue of patients with EG.

Of the transcripts studied, 104 were identified that exhibited differential regulation between the gastric tissue of these patients, including 28 that were up-regulated in EG patients and 76 that were down-regulated in EG patients compared to controls (Tables 9 and 10, respectively; FIG. 3A). Transcript levels of eotaxin-3 were monitored using cDNA derived from the gastric antrum tissue of patients used in the original microarray cohort and normalized to GAPDH levels for each sample. In both cohorts, relative eotaxin-3 transcript levels were significantly increased in the gastric tissue of patients with EG compared to that of control patients (FIG. 3B).

The transcripts identified in the EG transcriptome (this study) and the EoE transcriptome (Blanchard, C. et al. *J. Clin. Invest.* 116:536-47 (2006)) were compared, and transcripts present in both lists are shown along with the fold change in gene expression observed comparing the gene expression values derived from tissue of patients with active disease to tissue of control patients. Of the transcripts dysregulated in EG, 10 were also identified as being differentially regulated in the esophageal tissue of patients with active EoE, with six of these being regulated in a similar manner in both EoE and EG (Table 11, Blanchard, C. et al. *J. Clin. Invest.* 116:536-47 (2006)).

FIG. 3A. RNA isolated from the gastric antrum tissue of control patients or patients with active EG was subjected to microarray analysis. Transcripts with $p < 0.01$ (ANOVA) and additionally passing 2-fold filter analysis were defined as being differentially regulated between control and EG patients. Relative gene expression values are indicated per gene and per patient.

Figure 3B:
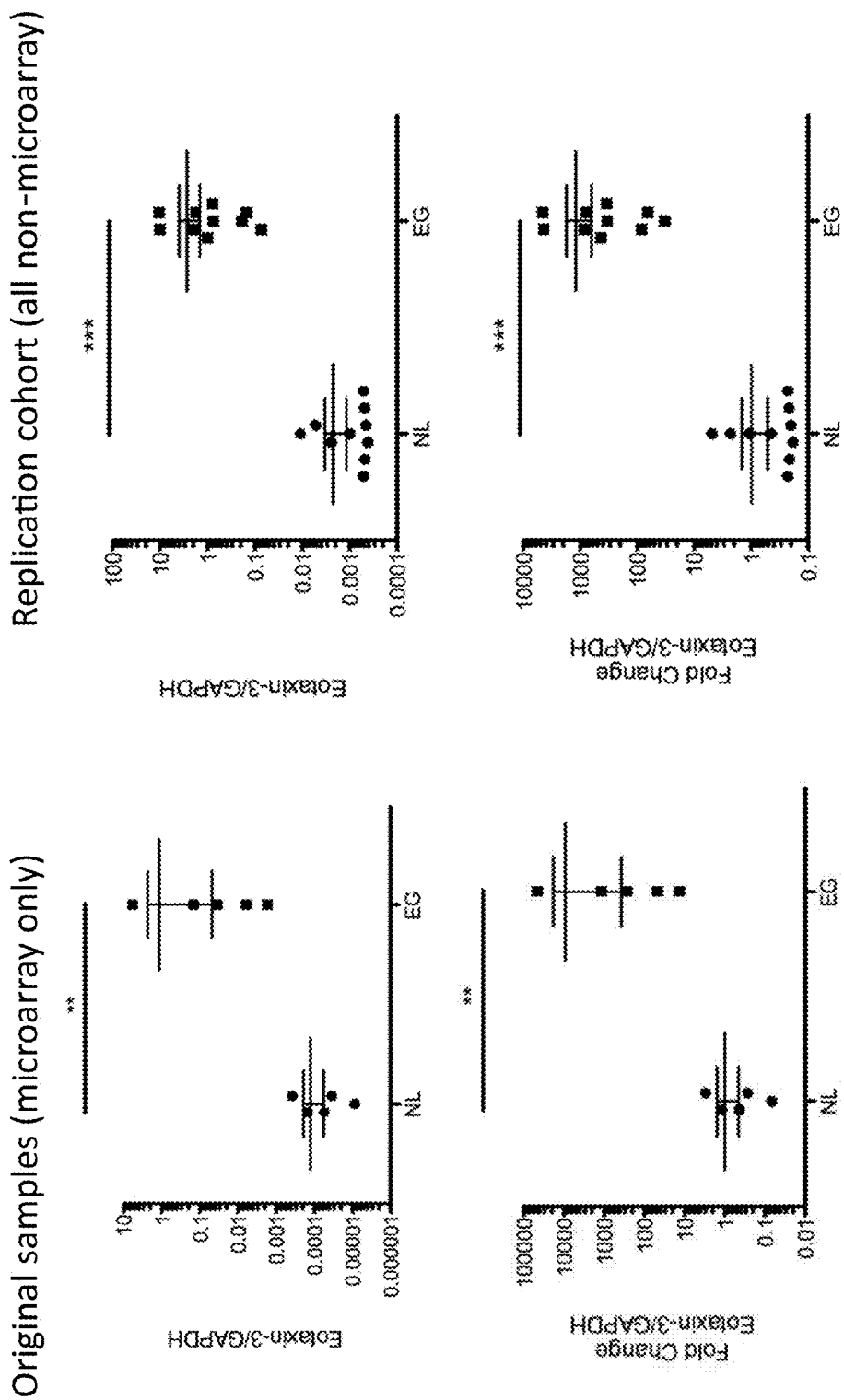

FIG. 3B. Transcript levels of eotaxin-3 were monitored using cDNA derived from the gastric antrum tissue of patients used in the original microarray cohort and normalized to GAPDH levels for each sample

TABLE 9

Genes up-regulated in EG patients compared to controls.

| Affy ID | Fold Change | Gene | Gene description | SEQ ID NO |
|---|---|---|---|---|
| 232306_at | 12.25 | CDH26 | Cadherin-like 26 | 1 |
| 206207_at | 9.634 | CLC | Charcot-Leyden crystal protein | 2 |
| 205534_at | 6.583 | PCDH7 | BH-protocadherin (brain-heart) | 3 |
| 206726_at | 5.552 | PGDS | Prostaglandin D2 synthase, hematopoietic | 4 |
| 219727_at | 4.991 | DUOX2 | Dual oxidase 2 | 5 |
| 217110_s_at | 3.825 | MUC4 | Mucin 4, cell surface associated | 6 |
| 218532_s_at | 3.813 | FAM134B | family with sequence similarity 134, member B | 7 |
| 218510_x_at | 3.63 | FAM134B | family with sequence similarity 134, member B | 8 |
| 204393_s_at | 3.256 | ACPP | Acid phosphatase, prostate | 9 |
| 229332_at | 3.197 | HPDL | 4-hydroxyphenylpyruvate dioxygenase-like | 10 |
| 224480_s_at | 2.973 | AGPAT9 | 1-acylglycerol-3-phosphate O-acyltransferase 9 | 11 |
| 213355_at | 2.89 | ST3GAL6 | ST3 beta-galactoside alpha-2,3-sialyltransferase 6 | 12 |
| 202587_s_at | 2.842 | AK1 | Adenylate kinase 1 | 13 |
| 219763_at | 2.693 | DENND1A | DENN/MADD domain containing 1A | 14 |
| 213924_at | 2.674 | MPPE1 | Metallophosphoesterase 1 | 15 |
| 204895_x_at | 2.434 | MUC4 | Mucin 4, tracheobronchial, cell surface associated | 16 |
| 233085_s_at | 2.415 | OBFC2A | oligonucleotide/oligosaccharide-binding fold containing 2A | 17 |
| 31874_at | 2.306 | GAS2L1 | Growth arrest-specific 2 like 1 | 18 |
| 1556588_at | 2.291 | C15orf37 | Hypothetical protein LOC283687 | 19 |
| 224461_s_at | 2.266 | AMID | Apoptosis-inducing factor (AIF)-like mitochondrion-associated inducer of death | 20 |
| 222872_x_at | 2.23 | OBFC2A | oligonucleotide/oligosaccharide-binding fold containing 2A | 21 |
| 201037_at | 2.167 | PFKP | Phosphofructokinase, platelet | 22 |
| 238846_at | 2.165 | TNFRSF11A | Tumor necrosis factor receptor superfamily, member 11a, NFKB activator | 23 |
| 207820_at | 2.109 | ADH1A | Alcohol dehydrogenase 1A (class I), alpha polypeptide | 24 |
| 219403_s_at | 2.1 | HPSE | Heparanase | 25 |
| 204140_at | 2.06 | TPST1 | Tyrosylprotein sulfotransferase 1 | 26 |
| 209729_at | 2.042 | GAS2L1 | Growth arrest-specific 2 like 1 | 27 |
| 210254_at | 2.006 | MS4A3 | membrane-spanning 4-domains, subfamily A, member 3 (hematopoietic cell-specific) | 28 |

TABLE 10

| | | | Genes down-regulated in EG patients compared to controls. | |
|---|---|---|---|---|
| Affy ID | Fold Change | Gene | Gene description | SEQ ID NO |
| 1568777_at | 0.497 | EML5 | Echinoderm microtubule associated protein like 5 | 29 |
| 233932_at | 0.497 | AL109791 | EST from clone 1206988, full insert | 30 |
| 1565830_at | 0.497 | KIAA1731 | KIAA1731 protein | 31 |
| 1555858_at | 0.493 | LOC440944 | UI-H-FL1-bfw-c-18-0-UI.s1 NCI_CGAP_FL1 *Homo sapiens* cDNA clone UI-H-FL1-bfw-c-18-0-UI 3', mRNA sequence. | 32 |
| 229141_at | 0.49 | WDR33 | WD repeat domain 33 | 33 |
| 241996_at | 0.49 | RUFY2 | RUN and FYVE domain containing 2 | 34 |
| 227663_at | 0.489 | AK098220 | CDNA FLJ40901 fis, clone UTERU2003704 | 35 |
| 234193_at | 0.488 | KIAA1579 | Hypothetical protein FLJ10770 | 36 |
| 235716_at | 0.487 | TRA2A | Transformer-2 alpha | 37 |
| 232489_at | 0.486 | FLJ10287 | Hypothetical protein FLJ10287 | 38 |
| 1555860_x_at | 0.485 | LOC440944 | UI-H-FL1-bfw-c-18-0-UI.s1 NCI_CGAP_FL1 *Homo sapiens* cDNA clone UI-H-FL1-bfw-c-18-0-UI 3', mRNA sequence. | 39 |
| 219317_at | 0.483 | POLI | Polymerase (DNA directed) iota | 40 |
| 232431_at | 0.483 | NR3C1 | Nuclear receptor subfamily 3, group C, member 1 (glucocorticoid receptor) | 41 |
| 230578_at | 0.481 | ZNF471 | Zinc finger protein 471 | 42 |
| 244008_at | 0.478 | PARP8 | poly (ADP-ribose) polymerase family, member 8 | 43 |
| 232395_x_at | 0.477 | LOC340351 | ATP/GTP binding protein-like 3 | 44 |
| 221211_s_at | 0.476 | C21orf7 | Chromosome 21 open reading frame 7 | 45 |
| 235803_at | 0.476 | CRLF3 | Cytokine receptor-like factor 3 | 46 |
| 238484_s_at | 0.475 | RPS8 | Ribosomal protein S8 | 47 |
| 239735_at | 0.474 | AC146944.2 | RST5450 Athersys RAGE Library *Homo sapiens* cDNA, mRNA sequence. (LincRNA) | 48 |
| 228497_at | 0.473 | SLC22A15 | Solute carrier family 22 (organic cation transporter), member 15 | 49 |
| 232773_at | 0.473 | MGC13057 | Hypothetical protein MGC13057 | 50 |
| 226181_at | 0.47 | TUBE1 | Tubulin, epsilon 1 | 51 |
| 239556_at | 0.47 | PDE5A | Phosphodiesterase 5A, cGMP-specific | 52 |
| 226587_at | 0.468 | SNRPN | *Homo sapiens* cDNA clone IMAGE: 5288750. small nuclear ribonucleoprotein polypeptide N. | 53 |
| 235611_at | 0.467 | SREK1 | 602574315F1 NIH_MGC_77 *Homo sapiens* cDNA clone IMAGE: 4702635 5', mRNA sequence, splicing regulatory glutamine/lysine-rich protein 1. | 54 |
| 1570507_at | 0.465 | SFRS2IP | Splicing factor, arginine/serine-rich 2, interacting protein | 55 |
| 242708_at | 0.463 | PEX1 | Peroxisome biogenesis factor 1 | 56 |
| 213267_at | 0.463 | KIAA1117 | KIAA1117 | 57 |
| 1552519_at | 0.462 | ACVR1C | Activin A receptor, type IC | 58 |
| 211923_s_at | 0.462 | ZNF471 | Zinc finger protein 471 | 59 |
| 233037_at | 0.461 | AF138859 | Clone FLB2932 mRNA sequence | 60 |
| 233019_at | 0.46 | CNOT7 | CCR4-NOT transcription complex, subunit 7 | 61 |
| 213142_x_at | 0.455 | PION | pigeon homolog (*Drosophila*) | 62 |
| 242598_at | 0.455 | AW294566.1 | Transcribed locus, strongly similar to NP_000700.1 branched chain keto acid dehydrogenase E1, alpha polypeptide [*Homo sapiens*] | 63 |
| 229546_at | 0.454 | NSE1 | NSE1 | 64 |
| 232633_at | 0.453 | XRCC5 | X-ray repair complementing defective repair in Chinese hamster cells 5 (double-strand-break rejoining; Ku autoantigen, 80 kDa) | 65 |
| 238454_at | 0.452 | ZNF540 | Zinc finger protein 540 | 66 |
| 235786_at | 0.436 | NUP88 | Nucleoporin 88 kDa | 67 |
| 1557050_at | 0.432 | HOTAIRM1 | *Homo sapiens*, clone IMAGE: 5019307, mRNA; HOTAIRM1 HOXA transcript antisense RNA, myeloid-specific 1 (non-protein coding) | 68 |
| 1556444_a_at | 0.429 | AK091686 | CDNA FLJ34367 fis, clone FEBRA2016621 | 69 |
| 243150_at | 0.428 | AK093442 | Transcribed locus | 70 |
| 223185_s_at | 0.427 | BHLHB3 | Basic helix-loop-helix domain containing, class B, 3 | 71 |
| 1552852_a_at | 0.425 | ZSCAN4 | Zinc finger and SCAN domain containing 4 | 72 |
| 236705_at | 0.425 | TMEM196 | transmembrane protein 196 | 73 |
| 225540_at | 0.424 | MAP2 | Microtubule-associated protein 2 | 74 |
| 221833_at | 0.419 | SIAH1 | Seven in absentia homolog 1 (*Drosophila*) | 75 |
| 243172_at | 0.415 | AK093713 | *Homo sapiens* cDNA FLJ36394 fis, clone THYMU2009104. | 76 |
| 1556666_a_at | 0.409 | TTC6 | Tetratricopeptide repeat domain 6 | 77 |
| 238796_at | 0.406 | YT521 | Splicing factor YT521-B | 78 |
| 238625_at | 0.395 | C1orf168 | Chromosome 1 open reading frame 168 | 79 |
| 231358_at | 0.394 | MRO | maestro | 80 |
| 239243_at | 0.393 | ZNF638 | Zinc finger protein 638 | 81 |
| 207050_at | 0.384 | CACNA2D1 | Calcium channel, voltage-dependent, alpha 2/delta subunit 1 | 82 |
| 208498_s_at | 0.381 | AMY1A | Amylase, alpha 1A; salivary | 83 |
| 1562612_at | 0.378 | ME2 | Malic enzyme 2, NAD(+)-dependent, mitochondrial | 84 |
| 236824_at | 0.373 | KIAA1906 | *Homo sapiens* KIAA1906 protein (KIAA1906), mRNA. | 85 |
| 227623_at | 0.36 | CACNA2D1 | calcium channel, voltage-dependent, alpha 2/delta subunit 1 | 86 |
| 244708_at | 0.355 | FLJ33996 | hypothetical protein FLJ33996 | 87 |
| 206017_at | 0.349 | KJAA0319 | KIAA0319 | 88 |
| 1563182_at | 0.346 | ACVR1C | activin A receptor, type IC | 89 |
| 226591_at | 0.343 | SNRPN | small nuclear ribonucleoprotein polypeptide N | 90 |
| 234314_at | 0.341 | RALGAPA2 | Ral GTPase activating protein, alpha subunit 2 (catalytic) | 91 |
| 1560258_a_at | 0.314 | BC035780 | *Homo sapiens*, clone IMAGE: 5590287, mRNA | 92 |
| 230081_at | 0.307 | PLCXD3 | Phosphatidylinositol-specific phospholipase C, X domain containing 3 | 93 |
| 239671_at | 0.304 | AK055647 | CDNA FLJ31085 fis, clone IMR321000037 | 94 |
| 229160_at | 0.301 | MUM1L1 | Melanoma associated antigen (mutated) 1-like 1 | 95 |

TABLE 10-continued

Genes down-regulated in EG patients compared to controls.

| Affy ID | Fold Change | Gene | Gene description | SEQ ID NO |
|---|---|---|---|---|
| 230333_at | 0.293 | SAT | Spermidine/spermine N1-acetyltransferase | 96 |
| 217617_at | 0.291 | KCTD7 | Potassium channel tetramerisation domain containing 7 | 97 |
| 1552851_at | 0.282 | ZSCAN4 | Zinc finger and SCAN domain containing 4 | 98 |
| 244455_at | 0.268 | KCNT2 | Potassium channel, subfamily T, member 2 | 99 |
| 221530_s_at | 0.26 | BHLHB3 | Basic helix-loop-helix domain containing, class B, 3 | 100 |
| 206678_at | 0.248 | GABRA1 | Gamma-aminobutyric acid (GABA) A receptor, alpha 1 | 101 |
| 223810_at | 0.242 | KLHL1 | Kelch-like 1 (*Drosophila*) | 102 |
| 244118_at | 0.196 | GABRA1 | Gamma-aminobutyric acid (GABA) A receptor, alpha 1 | 103 |
| 1568612_at | 0.189 | GABRG2 | Gamma-aminobutyric acid (GABA) A receptor, gamma 2 | 104 |

TABLE 11

Transcripts common between the EoE and EG transcriptomes.

| EG | EE | Gene | Gene description |
|---|---|---|---|
| 12.3 | 22.1 | CDH26 | cadherin-like 26 |
| 9.6 | 11.8 | CLC | Charcot-Leyden crystal protein |
| 5.6 | 6 | PGDS | prostaglandin D2 synthase, hematopoietic |
| 3.8 | 4.7 | MUC4 | mucin 4, cell surface associated |
| 3.3 | 4.2 | ACPP | acid phosphatase, prostate |
| 3 | 0.5 | AGPAT9 | 1-acylglycerol-3-phosphate O-acyltransferase 9 |
| 2.4 | 0.5 | MUC4 | mucin 4, cell surface associated |
| 2.2 | 0.4 | TNFRSF11A | tumor necrosis factor receptor superfamily, member 11a |
| 2.1 | 0.4 | HPSE | heparanase |
| 0.5 | 0.2 | SLC22A15 | solute carrier family 22 (organic cation transporter), member 15 |

Example 9

Increased CDH26 Gene Expression in EG

Cell adhesion is important in EGIDs. Both homophilic and heterophilic adhesion are important. Cadherin molecules consist of a large family of proteins that mediate calcium-dependent cell adhesion. These interactions can be mediated between cadherins and the same or other cadherin, or between cadherins and other molecules like integrins. Cadherin-like 26 (CDH26), a heretofore uncharacterized member of this family of proteins, appears to be upregulated in various $T_H2$-associated conditions (Woodruff, et al. *Proc. Nat. Acad. Sci.* 104:15858-63 (2007); Li and Gasbarre, *Int. J. Parasitol.* 39:813-24 (2009)).

Of the transcripts differentially regulated between EG biopsies and controls, CDH26 was the most highly up-regulated gene in the gastric tissue of EG patients (20.9 fold, p <0.01). To compare the relative expression of CDH26 to that of other cadherin family members, the mean raw expression value for each cadherin probe present on the microarray was calculated as an estimate of the relative abundance of each transcript.

Figure 4A:
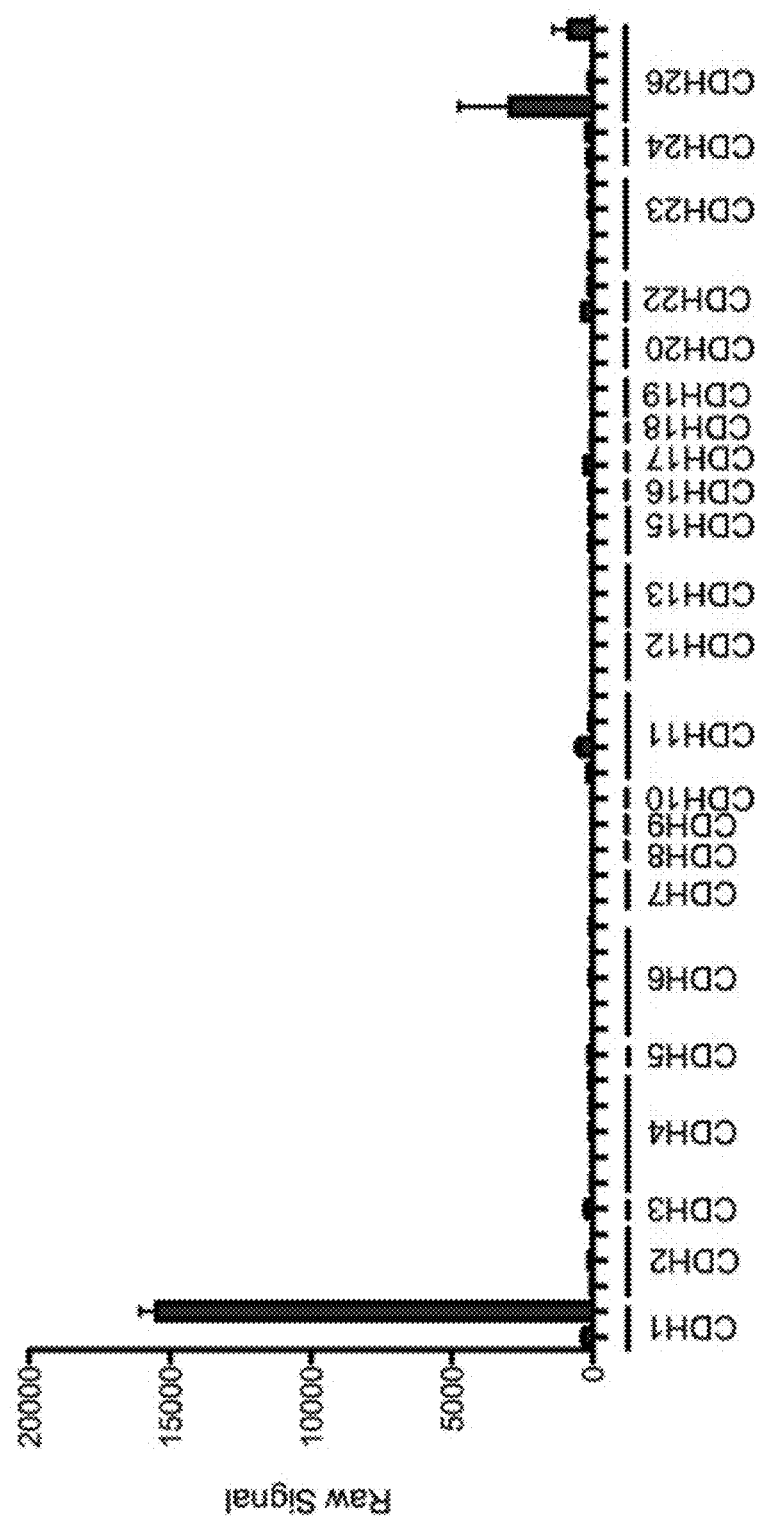
FIGS. 4A-E depict identification of transcripts differentially regulated in the gastric tissue of patients with EG.
Figure 4B:
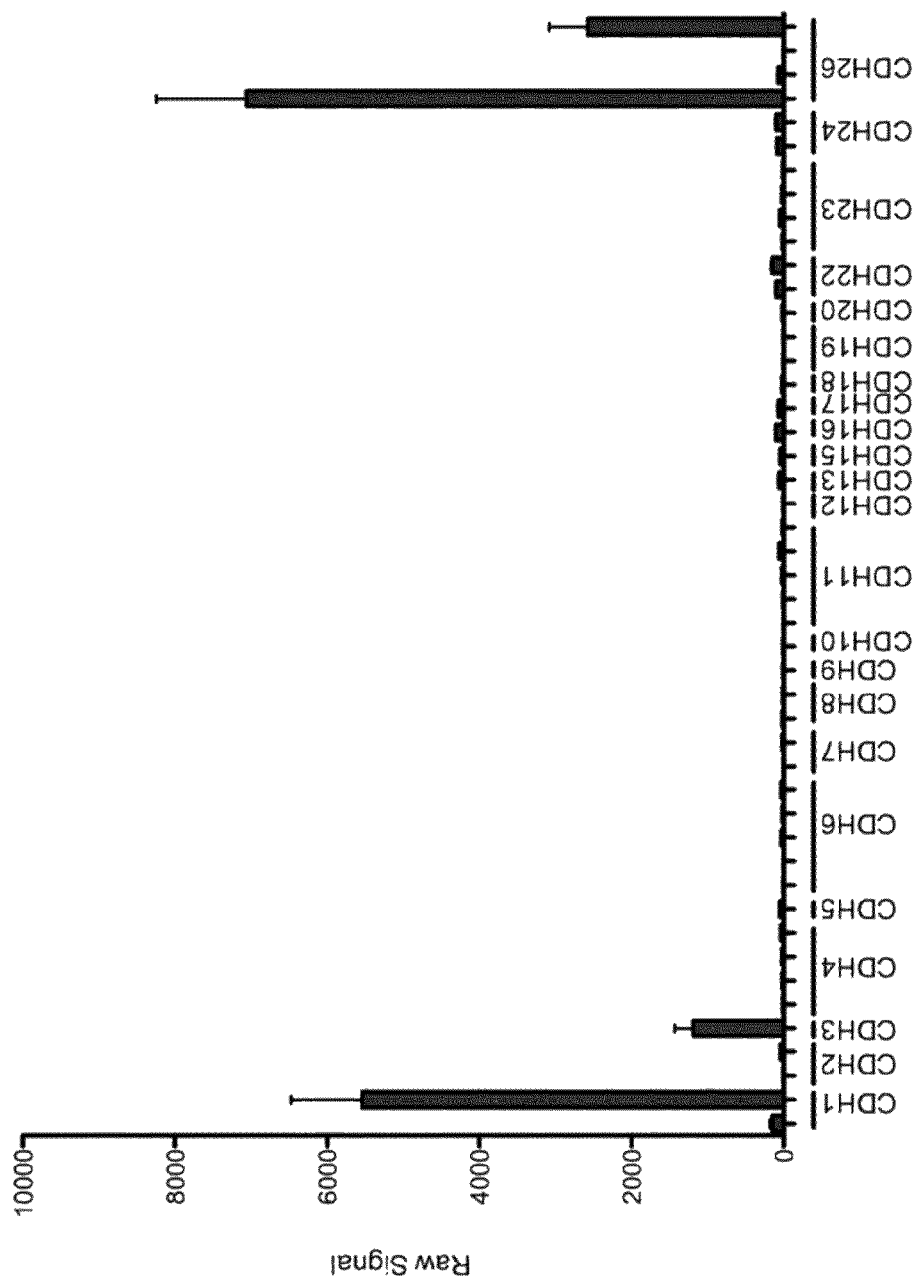

Of all cadherins, only CDH1 (E-cadherin) and CDH26 were found to exhibit raw signal that would indicate that the transcript is expressed (setting the threshold for expression of raw signal >100) (FIG. 4A). Similarly, raw signal for cadherin transcripts in esophageal tissue from patients with active EoE only showed high raw values for CDH1, CDH3 (P-cadherin), and CD1126 (FIG. 4B). CD1126 was further analyzed given its high relative expression.

The results from the gene microarray study (FIG. 4C) were verified by performing RT-PCR analysis using the same samples that had been subjected to microarray analysis. CDH26 mRNA exhibited 15.3-fold up-regulation in EG compared to control tissue (FIG. 4D). The expression pattern of CDH26 was confirmed in an independent, replication cohort of patients. Relative CDH26 levels were again found to be increased in patients with active EG (35.6-fold) in the replication cohort (FIG. 4E).

FIG. 4A. Summary of cadherin family member expression levels in inflamed gastric tissue. The mean raw expression values derived from the microarray data for each cadherin molecule are graphed for the five patients with active EG.

FIG. 4B. Summary of cadherin family member expression levels in inflamed esophageal tissue. The mean raw expression values derived from the microarray data for each cadherin molecule are graphed for the 14 patients with active EoE characterized in a previous study (Blanchard, C. et al. *J. Clin. Invest.* 116:536-47 (2006)).

Figure 4C:
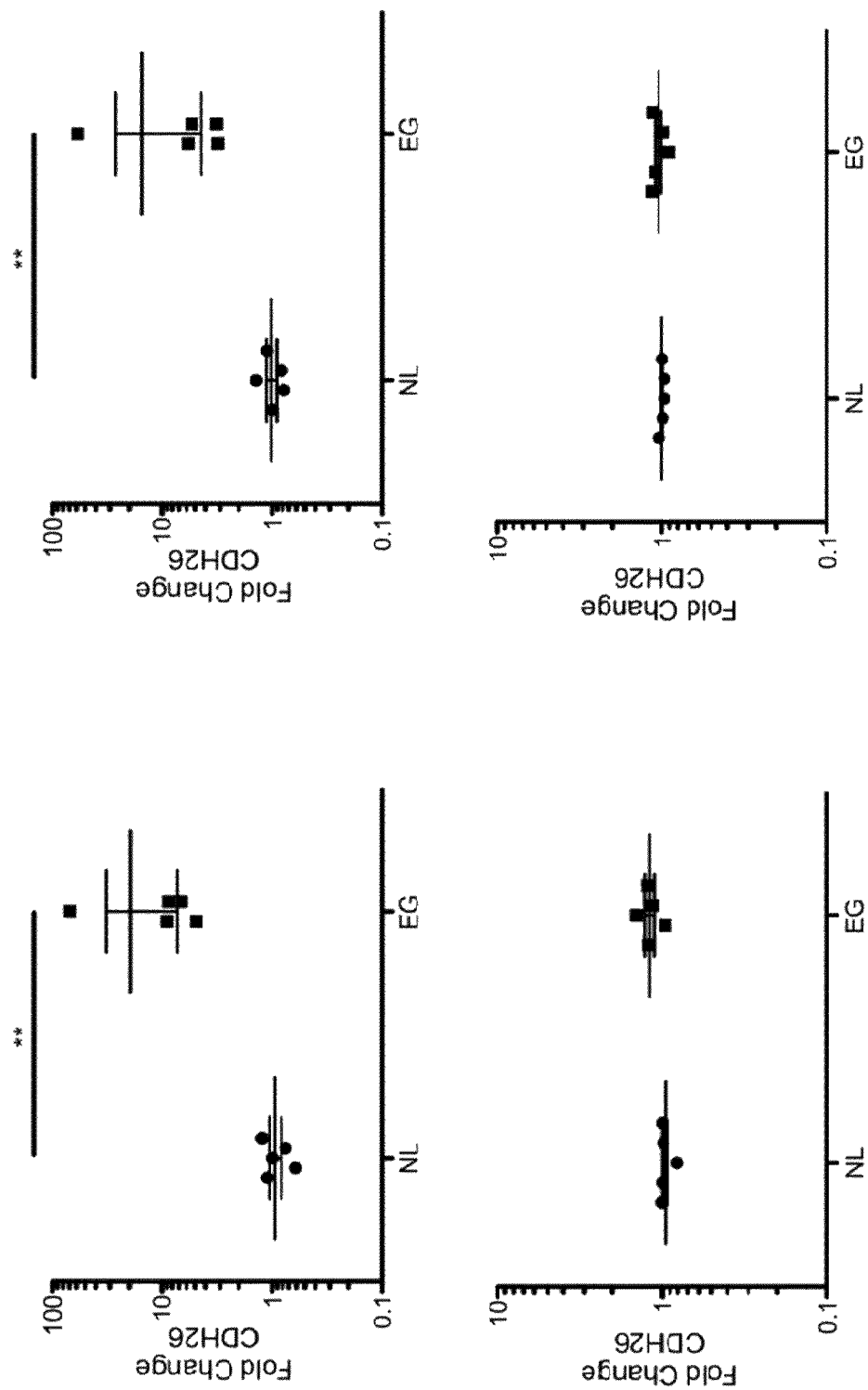
Figure 4E:
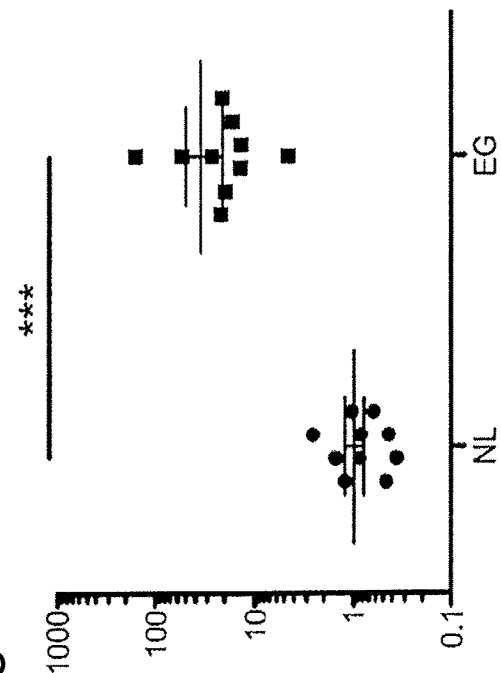
Figure 4D:
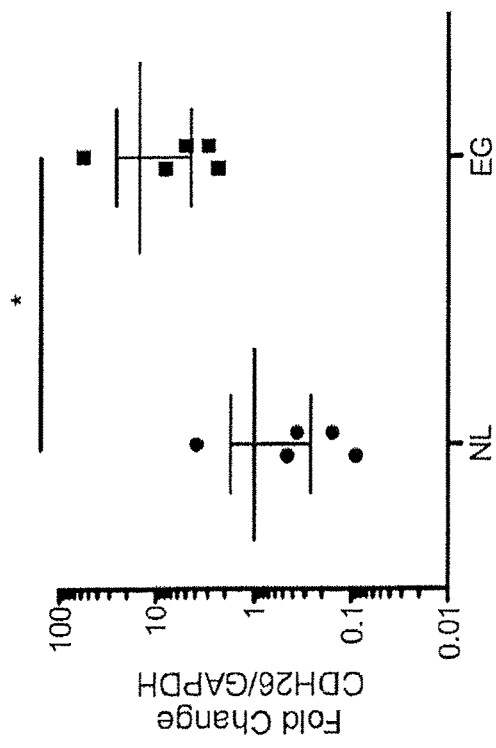

FIG. 4C. Transcript levels were identified by microarray analysis. CDH26 transcript levels were verified using cDNA derived from the gastric antrum tissue of the same population of patients used in the microarray study. The fold-change in normalized expression for four CDH26 probes on the Affymetrix HG U133 Plus 2.0 array is depicted (top left: 232306_at; top right: 233663_s_at; bottom left: 233391_at; bottom right: 233662_at).

FIG. 4D. CDH26 and GAPDH transcript levels from the same patient samples subjected to microarray analysis were quantified by real-time (RT-)PCR. CDH26 levels were normalized to GAPDH levels for each sample and are presented as fold-change relative to normal.

FIG. 4E. Relative CDH26 levels from a replication cohort of patients were determined. Data are presented as fold-change relative to normal.

Example 10

Increased CDH26 Protein Expression in EG

A subsequent study was designed to identify the quantity and localization of CDH26 protein expression in EG and control biopsies. Immunohistochemistry for CDH26 was performed on EG and control biopsies.

Figures 5A, 5B:
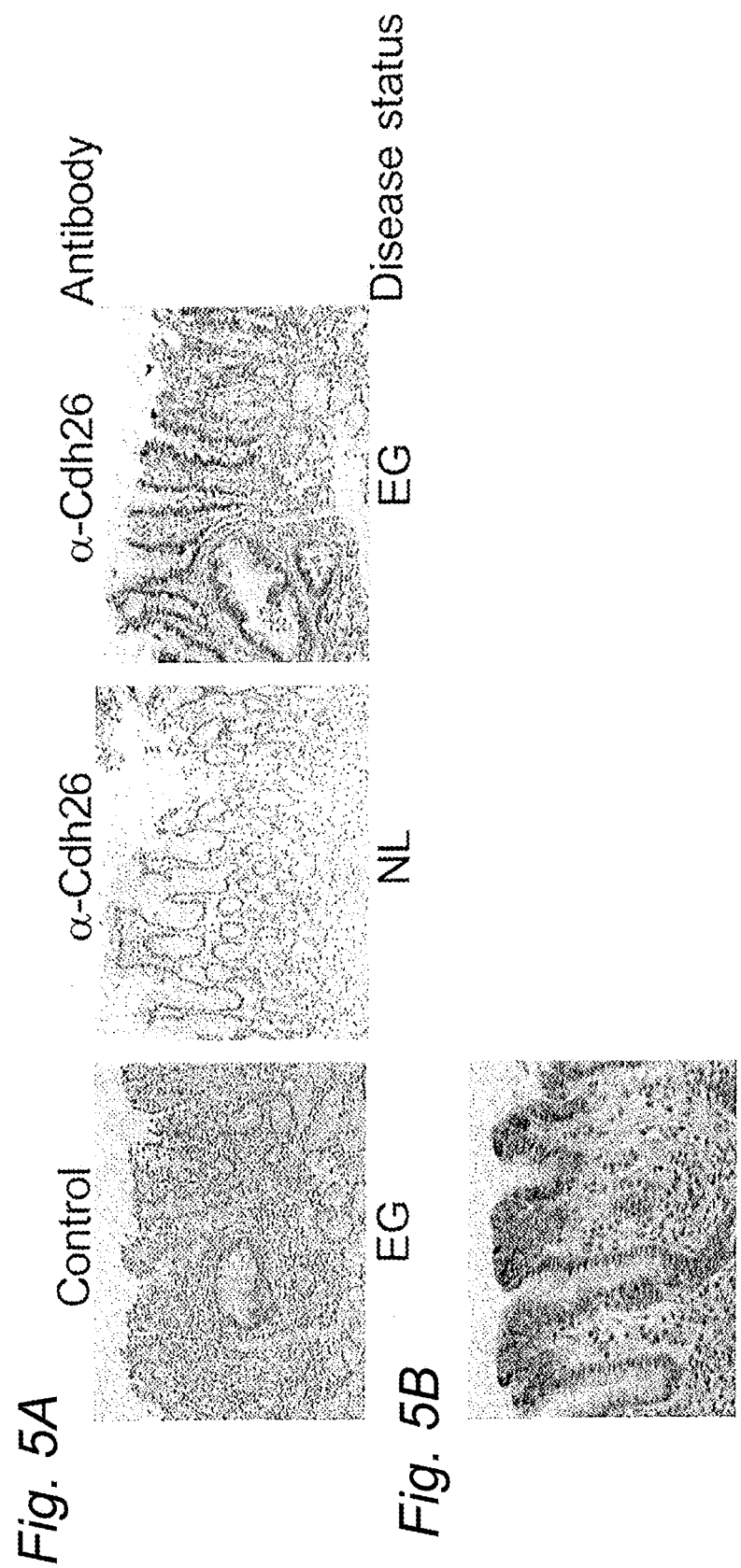
FIGS. 5A-D depict CDH26 localization in inflamed gastric tissue of patients with EG. Gastric antrum biopsy specimens obtained at the index endoscopy each of the original patient cohort were subjected to immunohistochemical staining for CDH26.
Figure 5C:
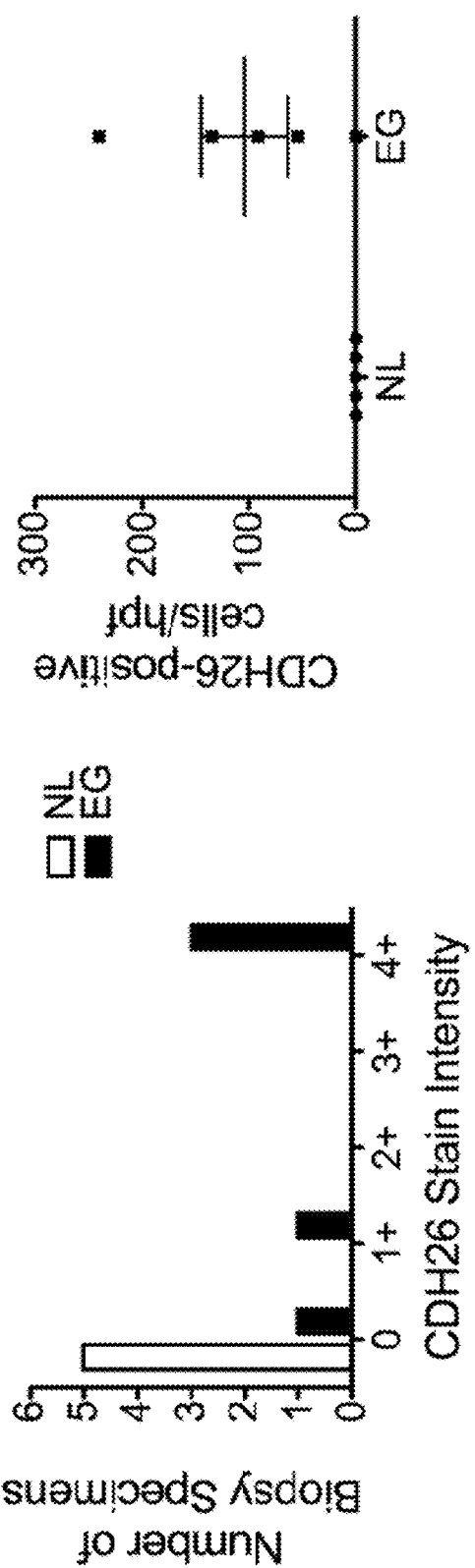

The surface epithelium in 4 of 5 EG biopsies, but none of the controls, was stained with anti-CDH26 (FIG. 5A, Table 7). The staining was cytoplasmic with focal membrane accentuation in the surface epithelial cells in EG biopsies (FIGS. 5A and 5B). Gland epithelial cells in both groups showed faint cytoplasmic staining. The intensity of the CDH26 signal was graded, and the peak number of CDH26- positive cells per high power field was quantified for each biopsy and graphed (FIG. 5C).

Figure 5D:
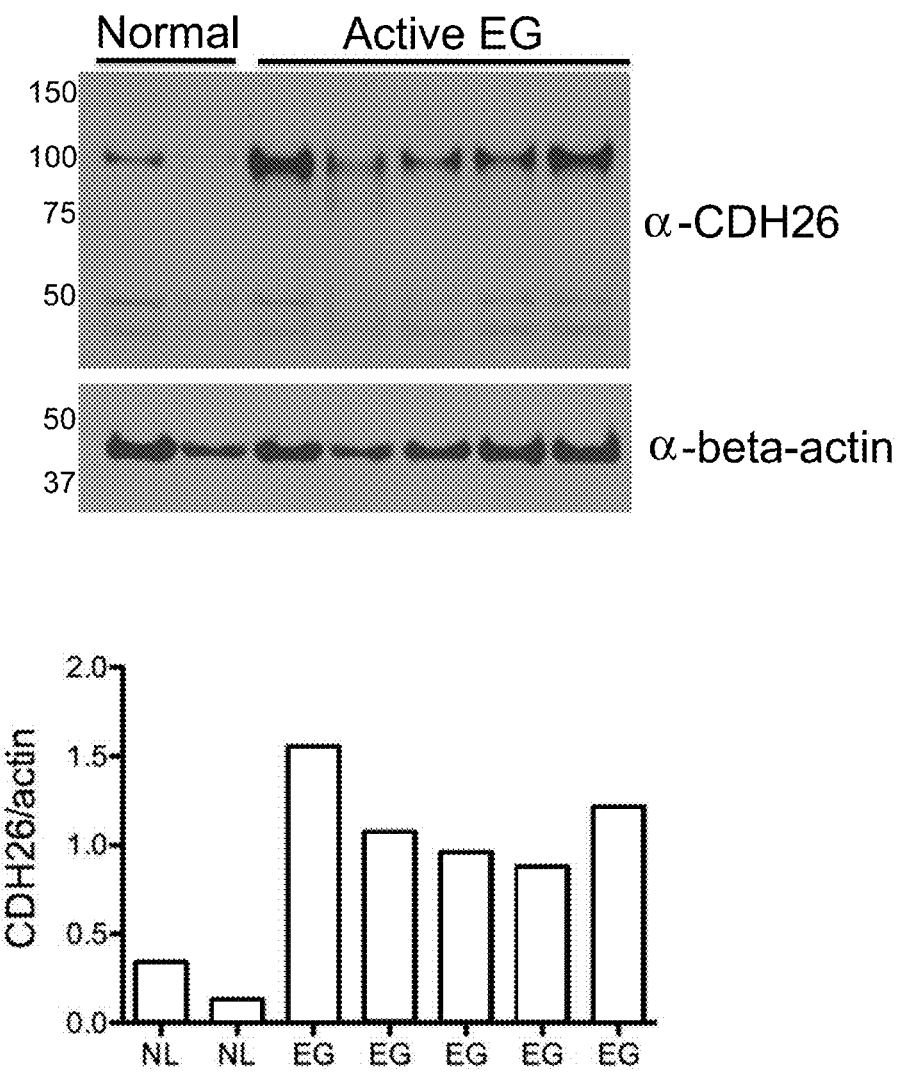

To confirm the increase in CDH26 protein observed and to confirm the molecular weight of the protein, western blot was performed on lysates obtained from the gastric antrum tissue of EG and control biopsies. CDH26 protein was found to be increased on average 2.3-fold in the gastric antrum tissue of EG patients compared to that of control patients (FIG. 5D).

FIG. 5A. Representative normal and EG biopsy specimens are depicted; the left panel shows a serial section of the biopsy stained with control antibody.

FIG. 5B. High magnification of gastric antrum tissue derived from a patient with active EG stained for CDH26 is depicted.

FIG. 5C. Quantification of the intensity and prevalence of CDH26-positive cells is depicted. The left panel displays the intensity of CDH26 staining, graded on a scale of 1-4, and the number of normal and EG biopsies assigned each score. The right panel displays results from quantification of the peak number of CDH26-positive cells per high power field per biopsy.

FIG. 5D. CDH26 protein levels in gastric antrum tissue are depicted.

Protein was isolated from the organic phase obtained following RNA isolation from the same gastric tissue. Protein lysates were subjected to SDS-PAGE and western blot analysis for CDH26 and beta-actin (top). The signal for CDH26 and beta-actin was quantified, and the ratio was graphed (bottom).

Example 11

Increased Expression of TH2 Cytokine IL-13 in EG

Cytokine transcripts have previously been shown to be increased and are critical components in the pathogenesis of EE. Therefore, to identify factors that promote EG pathogenesis, cytokine transcript levels in the gastric tissue of EG and control patients were determined.

Figure 6A:
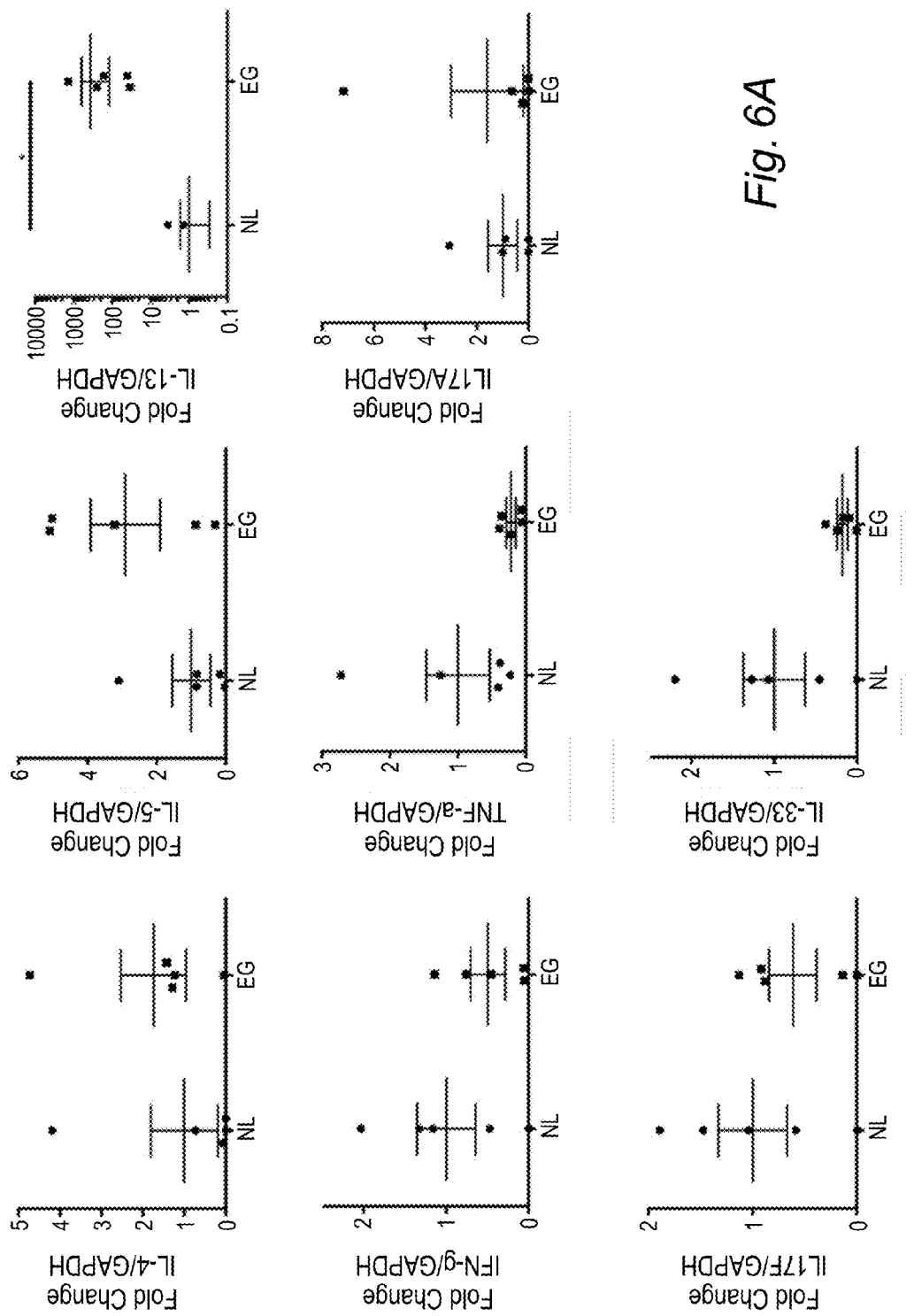
FIGS. 6A-B depict an analysis of cytokine transcript levels in gastric tissue.
Figure 6B:
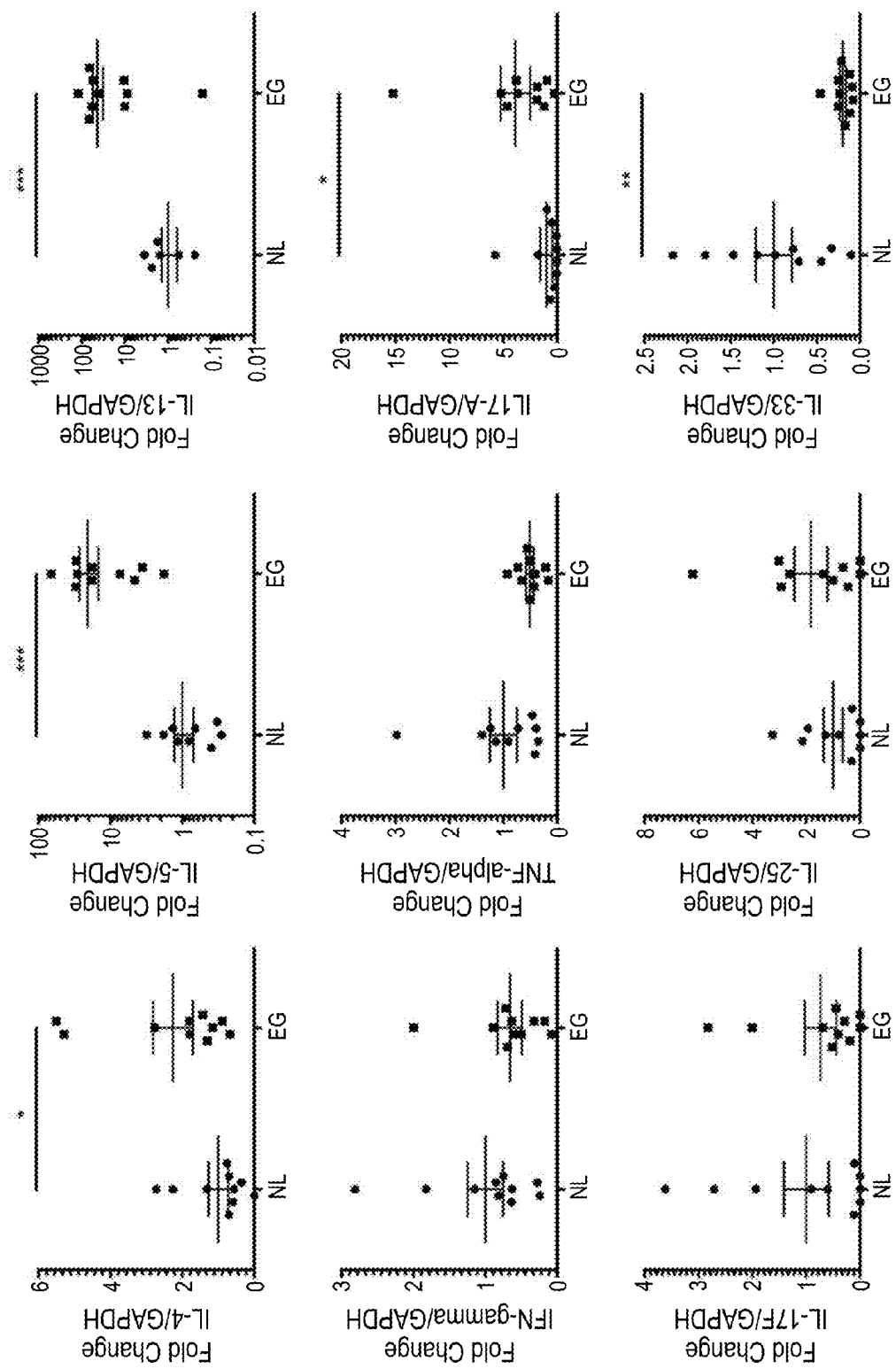

The $T_H2$ cytokine IL-13 showed significant (on average, 375-fold) up-regulation in EG compared to control biopsies, and a trend toward increased IL-4 and IL-5 was observed (FIG. 6A). A trend toward decreased TNF-alpha was seen in EG tissue. None of the other cytokines examined, namely interferon-gamma, IL-17A, IL-17F, or IL-33, exhibited a significant difference in transcript levels between control and EG patient tissue (FIG. 6A). Similar patterns of cytokine gene expression were observed when the relative levels were examined in the replication cohort (FIG. 6B). Significant decreases in IL-4, IL-5, IL-13, and IL-17A were observed in EG tissue compared to control tissue in the replication cohort. Although not tested in the original cohort, IL-25 transcript levels were monitored in the replication cohort, with no significant difference between control and EG tissue noted. In addition, IL-33 was shown to be significantly decreased in EG tissue compared to control tissue; therefore, IL33 is a dysregulated cytokine in EG.

FIG. 6A. Transcript levels of cytokines were monitored using cDNA derived from the gastric antrum tissue of the same population of patients used in the microarray study. Transcript levels for individual cytokines determined by RT-PCR were normalized to GAPDH levels for each sample.

FIG. 6B. Transcript levels of cytokines were monitored using cDNA derived from the gastric antrum tissue of the population of patients used in the replication cohort. Transcript levels for individual cytokines were normalized to GAPDH levels for each sample.

Example 12

Replication Cohort

Following the initial genetic, molecular, and histopathologic analyses, biopsies from additional patients who met the entry criteria were analyzed. This analysis focused on the most dysregulated genes identified in the initial cohort. The methods used for the additional analyses were identical to those used for the analysis in the initial cohort.

After completion of analyses on the discovery cohort, ten additional EG patients and five additional control patients were identified in the CCED database who met entry criteria. All patients included in the EG cohort exhibited increased eosinophil numbers and the other alterations described in the biopsies of the discovery cohort.

Data for the replication cohort are shown in Examples 8, 9, and 11 and in FIGS. 3B and 4E.

Example 13

Up-Regulation of CDH26 in EoE

CDH26 transcripts have been shown previously to be markedly increased in the esophageal biopsies of patients with EoE (Blanchard, C. et al. J. Clin. Invest. 116:536-47 (2006); Blanchard, C. et al. J. Allergy Clin. Immunol. 120:1292-300 (2007)). Since several of the patients in this study who had active EG also had active EoE at incident endoscopy, a study was designed to confirm and expand the prior studies concerning CDH26 and EoE.

CDH26 transcript levels in esophageal tissue from normal patients and patients with active EoE were measured. CDH26 expression was found to be significantly increased (median=114.9-fold) in the esophageal tissue of patients with active EoE (FIG. 7A).

Within the initial cohort of patients used in this study, several had esophageal biopsy specimens collected for research purposes. The CDH26 transcript levels in these biopsy specimens were analyzed, and patients with EG who also had EoE at the time were found to exhibit increased esophageal CDH26 transcript levels compared to the normal patients who did not have concomitant EoE or any other EGID (FIG. 7B). Similarly, patients with active EG but normal esophageal pathology showed low levels of CDH26 protein expression, in contrast to EG patients that also had esophageal eosinophilia, whose esophageal tissue exhibited high levels of CDH26 protein expression (FIG. 7C). In a separate cohort of patients, esophageal tissue of patients with active EoE showed on average 3.4-fold increased CDH26 protein levels compared to that observed in control tissue, as determined by western blot (FIG. 7D).

Immunohistochemical staining for CDH26 protein in esophageal biopsies corresponded with this observation. Esophageal biopsies from EG patients who had active EoE showed increased staining for CDH26 compared to esophageal biopsies from EG patients who did not have active EoE (FIG. 7C). In biopsies without active EoE, the staining was confined to epithelial cells near the surface, but the staining in active EoE was both more intense and prevalent and included cells in the expanded basal layer. Peripapillary epithelial cells did not stain in either group (FIG. 7C). In addition, biopsies from patients other than those who were the focus of this study who had active EoE but not EG showed increased staining compared to control patients, particularly in the suprabasal region of the esophageal epithelium (FIG. 7D).

Figure 7A:
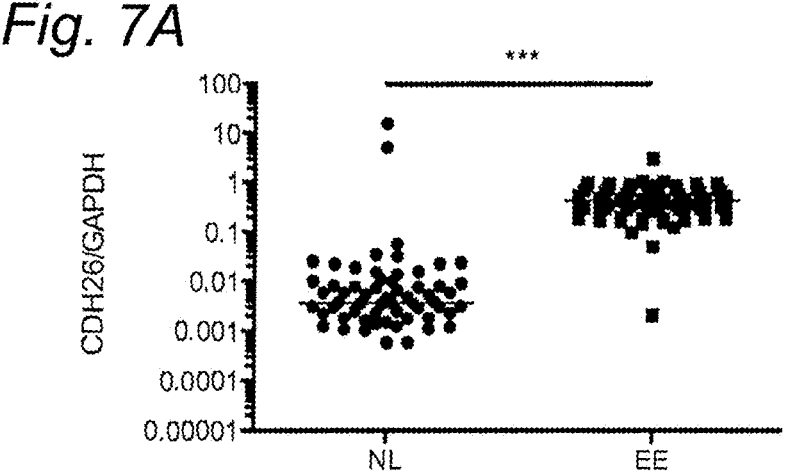
FIGS. 7A-D depict the increased CDH26 transcript and protein levels in the esophageal tissue of patients with EoE.
Figure 7B:
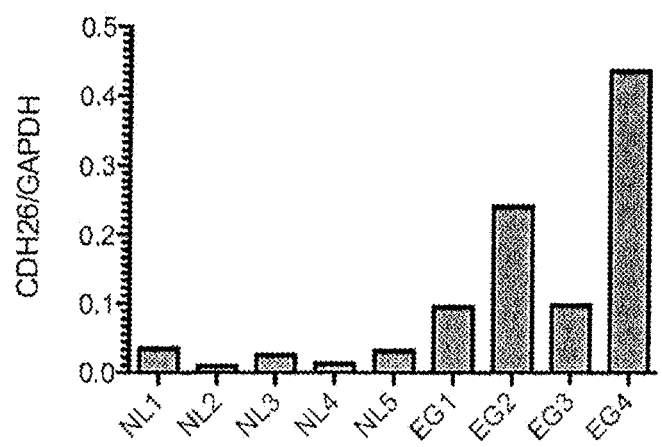
Figure 7C:
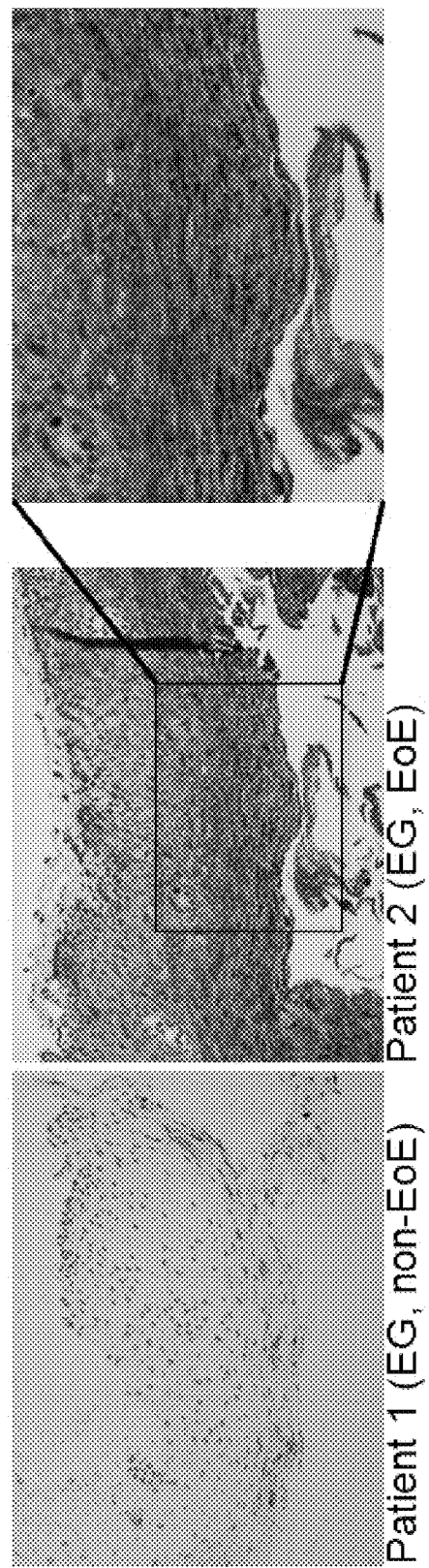
Figure 7D:
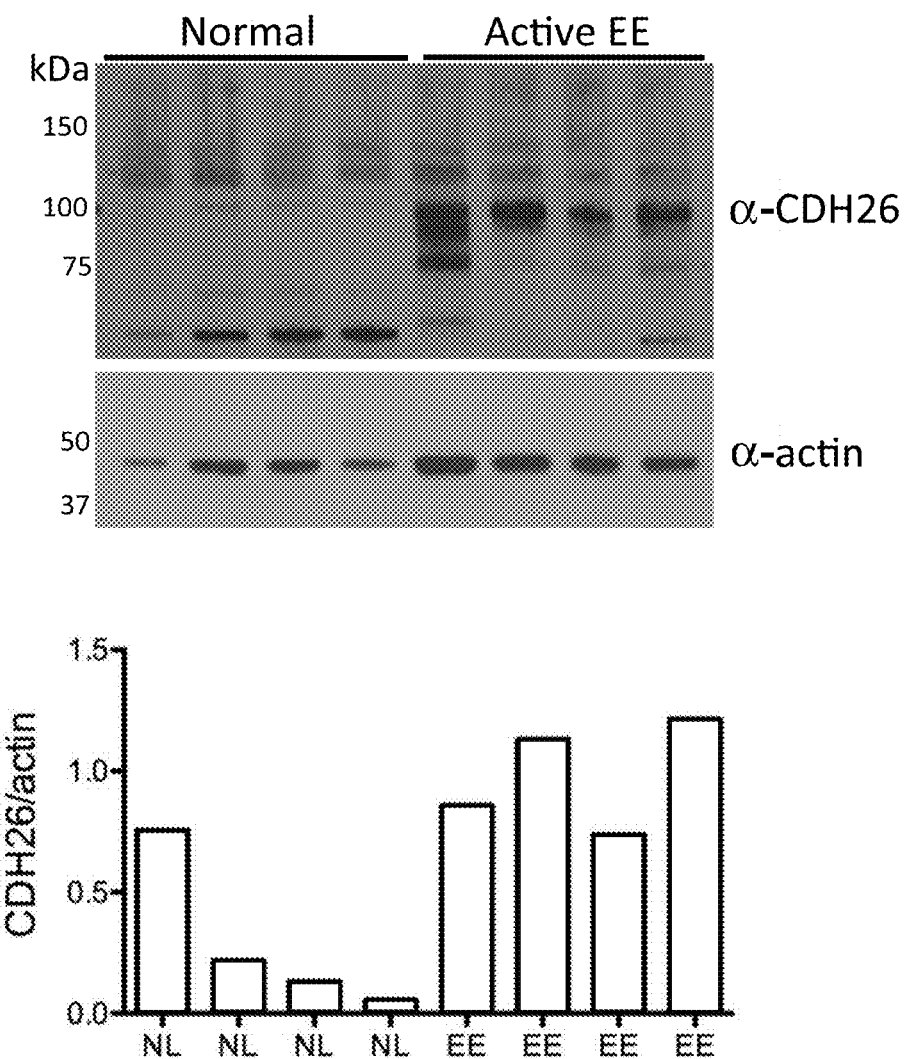

FIG. 7A. CDH26 transcript levels were determined using cDNA derived from the esophageal tissue of either normal patients or patients with EoE and normalized to GAPDH levels.

FIG. 7B. CDH26 transcript levels were measured using cDNA derived from the esophageal tissue of patients obtained during the index endoscopy from which the gastric specimens were obtained. CDH26 levels were normalized to GAPDH levels for the same sample.

FIG. 7C. CDH26 protein expression and localization in esophageal tissue are depicted. Immunohistochemical staining for CDH26 was performed on esophageal biopsy specimens obtained during the index endoscopy from which the gastric specimens were obtained. Patient numbers correspond to those in Table 4.

FIG. 7D. Total protein lysates were prepared from esophageal biopsy specimens from an independent cohort of patients who either had active EoE or no history of EGID. SDS-PAGE and western blot analysis were carried out to detect CDH26 and beta-actin (top). The signals for CDH26 and beta actin were quantified, and the ratio was graphed (bottom).

Example 14

Figure 8A:
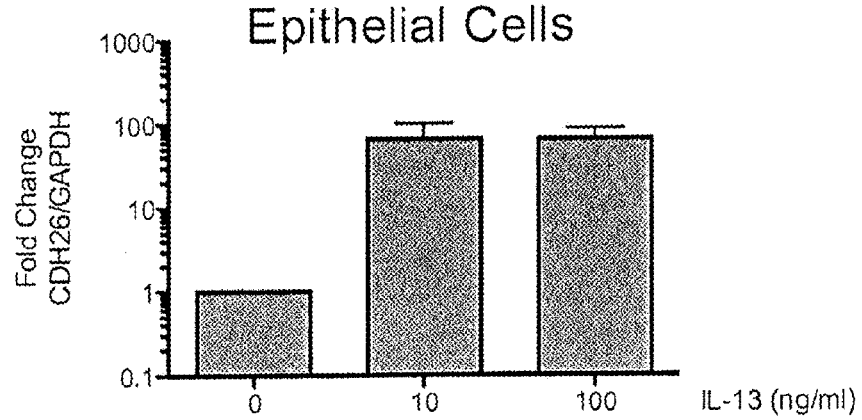
FIGS. 8A-F depict the increased CDH26 mRNA levels in esophageal and gastric epithelial cells stimulated with IL-13 and the localization of CDH26 expression in esophageal and gastric epithelial cells.
Figure 8B:
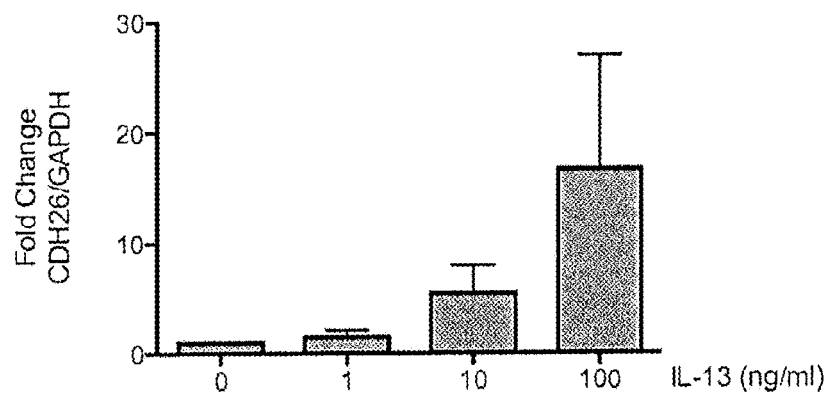

Induced CDH26 Expression Via IL-13 in Cultured Cells and CDH26 Subcellular Localization, Glycosylation, and Interactions Previous studies have demonstrated that IL-13 is sufficient to induce CDH26 transcripts in esophageal epithelial cells (Blanchard, C. et al. *J. Allergy Clin. Immunol.* 120: 1292-300 (2007)). CDH26 transcript levels increased in a dose-dependent manner in primary esophageal epithelial cells treated with IL-13 (FIG. 8A). Similarly, upon IL-13 stimulation, CDH26 mRNA increased in a dose-dependent manner in the esophageal cell line TE-7 (FIG. 8B).

Figure 8C:
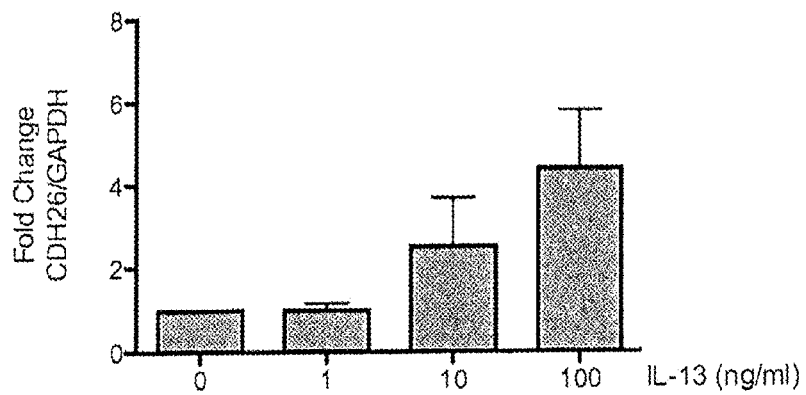

A follow-up study was designed to determine whether IL-13, which exhibits increased transcript levels in gastric biopsy specimens, induced CDH26 expression in the gastric cell line NCI-N87. Indeed, IL-13 stimulation resulted in a dose-dependent increase in CDH26 transcripts in these cells (FIG. 8C).

Immunohistochemical staining of esophageal biopsies for CDH26 showed cytoplasmic cellular staining with a suggestion of membrane accentuation focally. A study was therefore desinged to determine the subcellular localization of CDH26 protein using cultured esophageal epithelial cells.

Figure 8D:
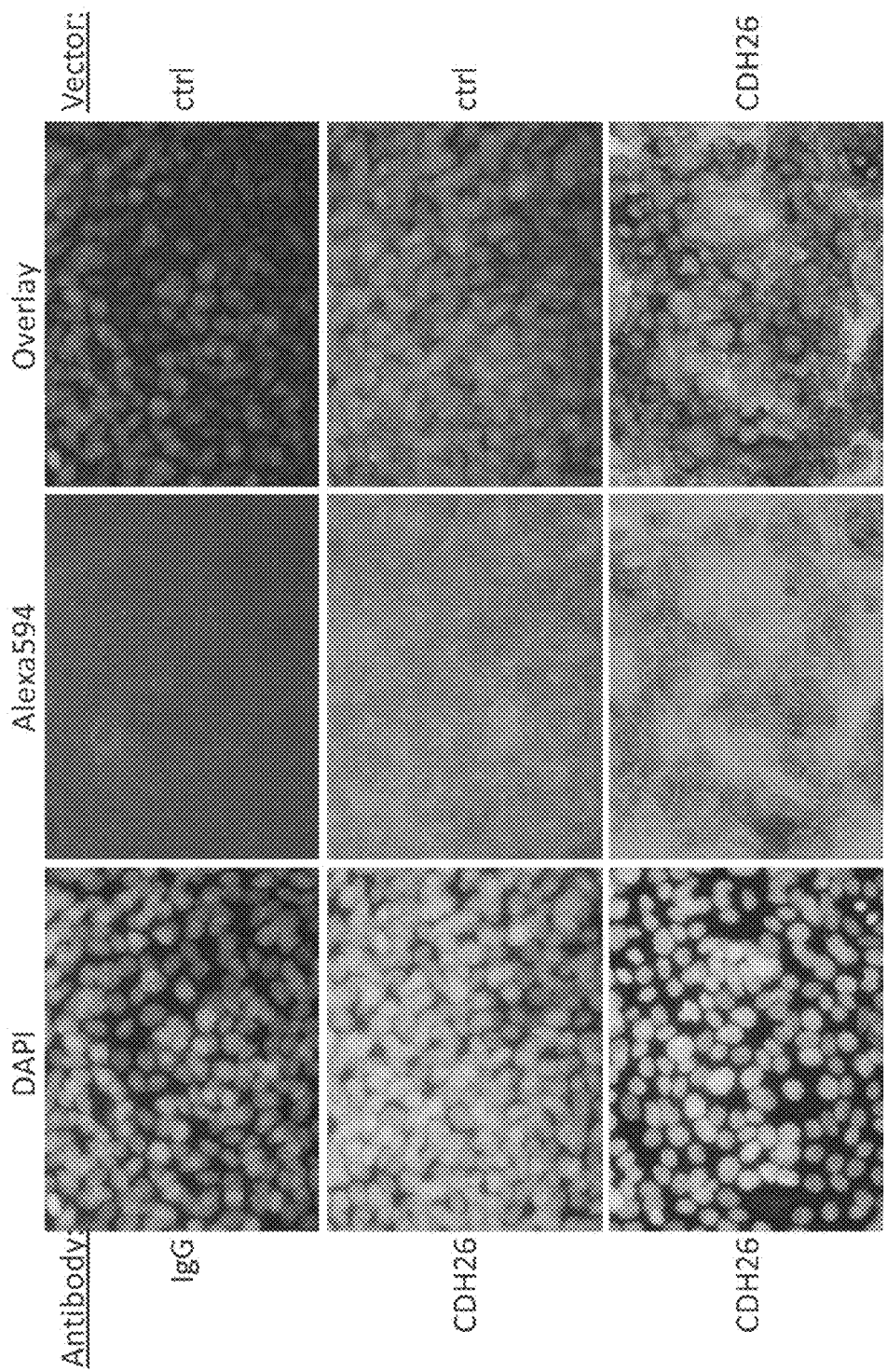

Because CDH26 exhibits sequence homology to the cadherin family of proteins, with 5 cadherin repeats in the putative extracellular portion of the protein, a predicted transmembrane domain, and a C-terminal cytoplasmic region, CDH26 protein can be localized to the plasma membrane in cells. TE-7 cells transduced with a CDH26 expression construct were fixed and stained with antibodies for CDH26. Signal was observed in the cytoplasm and membranes of the cells (FIG. 8D).

Figure 8E:
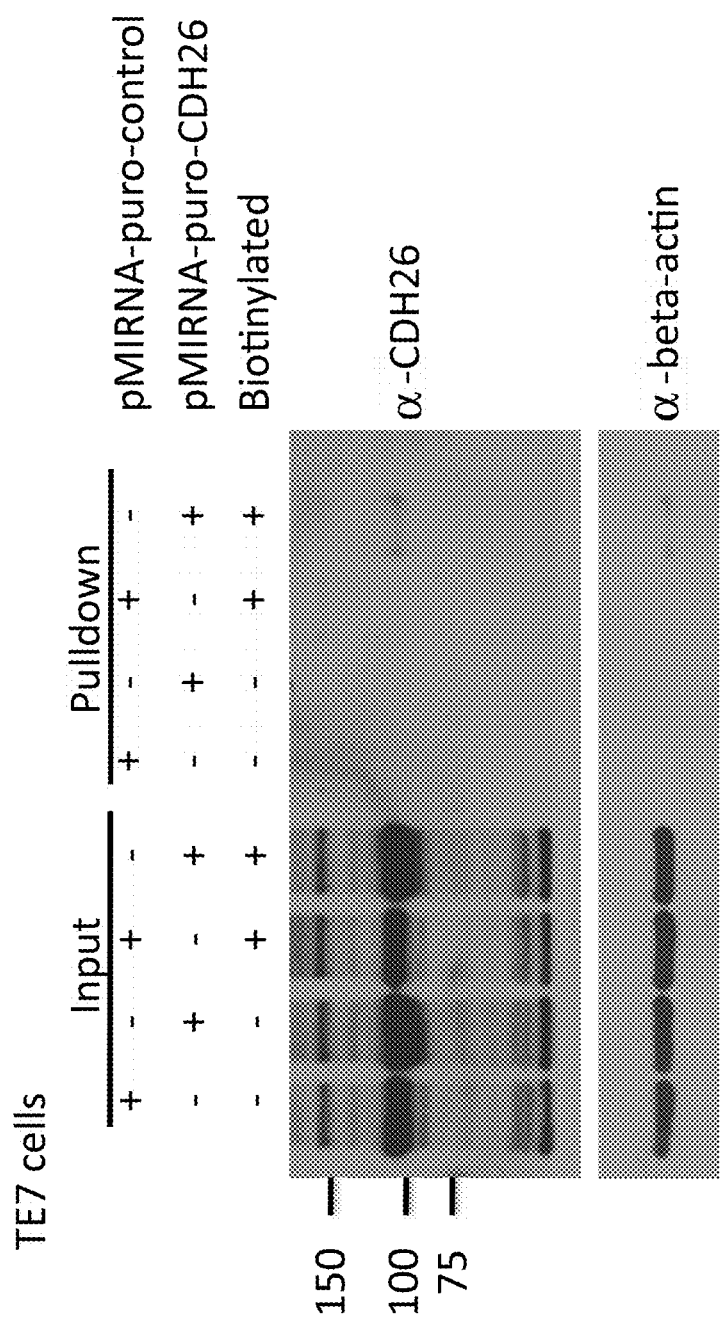
Figure 8F:
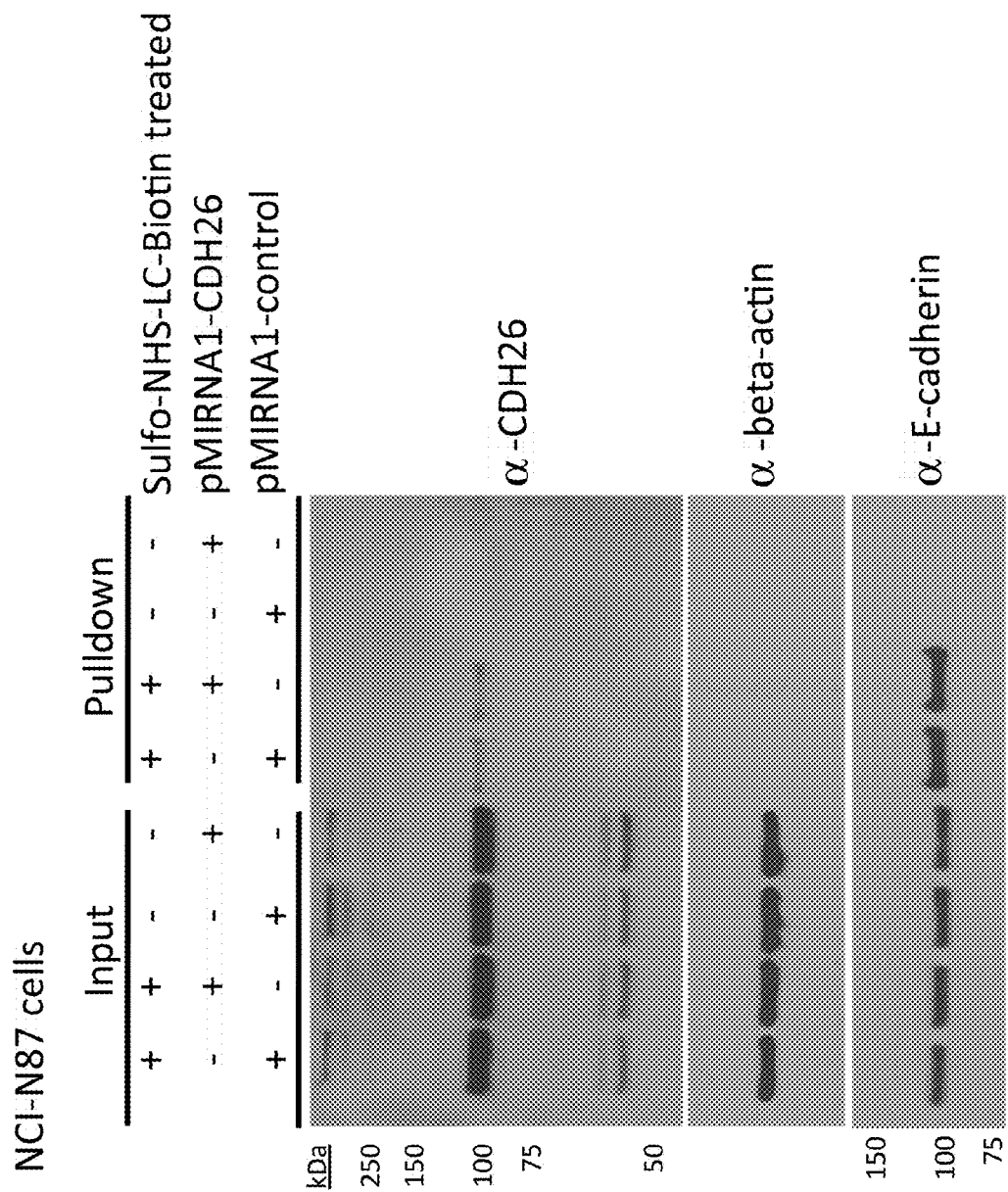

To further substantiate the indicated localization of CDH26, surface biotinylation of proteins was performed, followed by affinity isolation of biotinylated proteins and western blot analysis for CDH26. This indicated that CDH26 was present at the cell surface in TE-7 and NCI-N87 cells (FIGS. 8E-8F).

FIG. 8A. Primary esophageal epithelial cells were cultured from distal esophageal biopsy specimens. For each patient, cells were treated in triplicate with the indicated dose of IL-13 for 48 hours. Total RNA was isolated, cDNA synthesis was performed, and RT-PCR analysis was done to monitor CDH26 and GAPDH levels. The graph represents the average fold-change compared to untreated cells for five patients.

FIG. 8B. TE-7 cells were treated with the indicated dose of IL-13 for 48 hours, followed by RNA isolation, cDNA synthesis, and RT-PCR for CDH26 and GAPDH. The graphs represent the average of three experiments.

FIG. 8C. NCI-N87 cells were treated with the indicated dose of IL-13 for 48 hours. RNA was then isolated, cDNA synthesis was performed, and RT-PCR for CDH26 and GAPDH was done. The graphs represent the average of three experiments.

FIG. 8D. TE-7 cells that were transduced with either pMIRNA1-puro-control or -CDH26 were fixed and stained either with antibody specific for CDH26 or an equivalent amount of control IgG antibody. Nuclei were stained with DAPI.

FIG. 8E. Surface biotinylation of TE-7 cells is depicted. TE7 cells transduced with either pMIRNA1-puro-control or -CDH26 were incubated with a membrane-impermeable reagent that reacts with and binds covalently to cell surface proteins. Proteins were then solubilized in immunoprecipitation buffer. Protein lysates were subjected to pulldown using streptavidin beads. Total cell lysates (input) and proteins bound to the streptavidin beads were subjected to SDS-PAGE and western blot analysis for the indicated proteins.

FIG. 8F. Surface biotinylation of NCI-N87 cells is depicted. NCI-N87 cells transduced with either pMIRNA1-puro-control or -CDH26 were treated as described for TE-7 cells in FIG. 8E.

Example 15

Similarities Between CDH26 and Classical Cadherin Molecules

Classical cadherin molecules are known to mediate cell-cell adhesion through homotypic interactions. Therefore, a study was designed to determine whether CDH26 molecules interact in a homotypic manner using transient transfection and immunoprecipitation experiments.

Figure 9A:
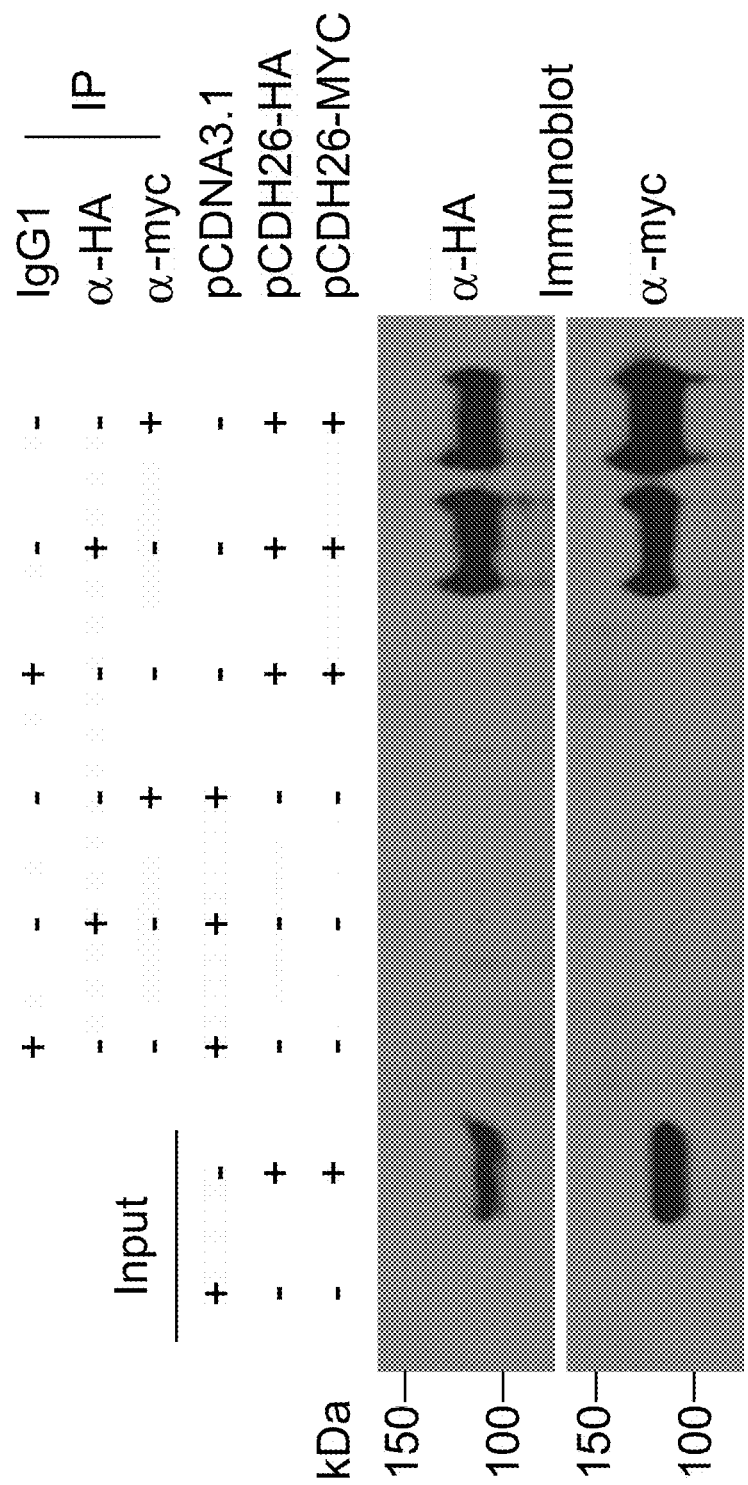

HEK 293T cells were co-transfected with two separate expression constructs containing either CDH26-myc or CDH26-HA. Myc-tagged CDH26 was observed to co-immunoprecipitate with HA-tagged CDH26. The reciprocal immunoprecipitation confirmed that HA-tagged CDH26 co-immunoprecipitated with myc-tagged CDH26 (FIG. 9A).

Classical cadherin molecules have additionally been shown to be modified by glycosylation, which alters the adhesive function of these molecules. Therefore, a follow-up study was designed to determine whether CDH26 was glycosylated by performing experiments in which HEK 293T cells were transfected with an expression construct containing HA-tagged CDH26.

CDH26 was immunoprecipitated and then treated with peptide:N-glycosidase F (PNgase F) to remove N-linked glycosylation. Immunoprecipitated CDH26 treated with PNgase F, but not heat-inactivated PNgase F, exhibited an increased mobility compared to CDH26 from total cell lysates (FIG. 9B), indicating that the protein is modified by N-glycosylation under baseline conditions in these cells.

Classical cadherin molecules, including E-cadherin and N-cadherin, have been shown to interact with catenin proteins, which bind the C-terminal cytoplasmic portion of the cadherin protein to link it to the actin cytoskeleton. A study was therefore designed to determine whether CDH26 interacts with beta-catenin, an essential component of the Wnt signaling pathway that is important in gastrointestinal homeostasis.

Figure 9C:
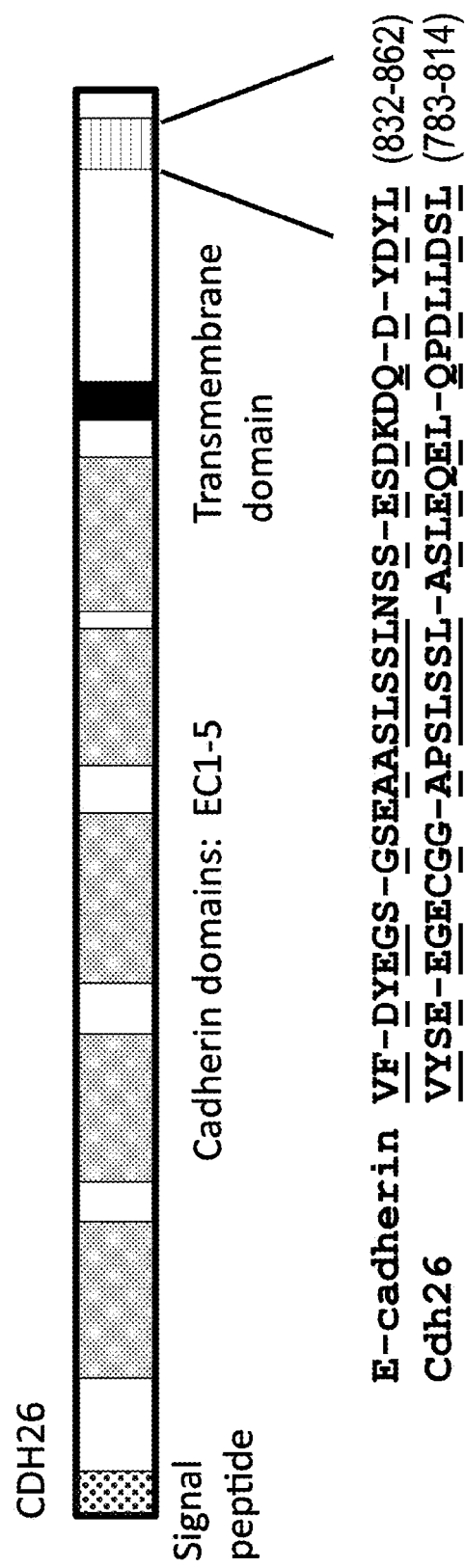

The region of other cadherin molecules known to interact with beta-catenin exhibited similarity to the same region of CDH26 (FIG. 9C; Stappert and Kemler, *Cell Adhes. Commun.* 2:319-27 (1994)). HEK 293T cells were co-transfected with expression constructs containing CDH26 or HA-tagged beta-catenin (CTNNB1). When immunoprecipitation for HA-tagged beta-catenin was performed, CDH26 was also detected in the precipitates (FIG. 9D), indicating that ectopically expressed beta-catenin and CDH26 exist in the same complex in these cells.

Since CDH26 localizes with beta-catenin in cultured cells, EG and control gastric biopsies were stained with antibody to beta-catenin. Surface epithelial cells in control biopsies showed distinct staining of the basolateral cell membrane. HEK 293T cells were transiently transfected with the indicated constructs. Total cell lysates were then prepared and equal amounts of protein were subjected to immunoprecipitation using the indicated antibodies. Inputs (1/10 of the amount used for IP) and immunoprecipitates were subjected to SDS-PAGE and western blot analysis with the indicated antibodies.

Beta-catenin interacts with alpha-catenin to indirectly link cadherin molecules to the actin cytoskeleton and thus support cell adhesion. Therefore, a follow-up study was designed to determine whether alpha-catenin can exist in the same complex as CDH26 by performing transient transfection and immunoprecipitation experiments.

HEK 293T cells were transfected with pCDH26 and a construct expressing HA-tagged CTNNA1. CDH26 was observed to co-immunoprecipitate with alpha-catenin (FIG. 9E).

The jutxamembrane domain of the cytoplasmic portion of cadherin molecules is bound by p120-catenin, which has been shown to function in maintenance of cadherin stability and localization to the cell surface. Therefore, a follow-up study was designed to test whether CDH26 and p120 could exist in the same protein complex. p120 and CDH26 co-immunoprecipitated from lysates derived from HEK 293T cells transiently transfected with pCDH26 and a construct that expresses p120 (FIG. 9F).

FIG. 9A. HEK 293T cells were transiently transfected with the indicated construct(s). Total cell lysates were prepared, and immunoprecipitation was performed using the indicated antibodies. Inputs (1/10 of amount used for IP) or immunoprecipitates were subjected to SDS-PAGE and western blot analysis with anti-HA antibodies; the same blot was then stripped and probed with anti-myc antibodies. The blot shown is representative of three independent experiments. Predicted molecular weight of CDH26: 95.3 kDa.

FIG. 9B. Post-translational modification of CDH26 is shown. HEK 293T cells were transiently transfected with the indicated construct(s). Total cell lysates were prepared, and immunoprecipitation was performed using the indicated antibodies. Immunoprecipitates were treated with either PNGase F (+) or heat-inactivated PNGase F (−). Inputs (1/10 of amount used for IP) or treated immunoprecipitates were subjected to SDS-PAGE and western blot analysis using anti-HA antibodies. The blot shown is representative of three independent experiments.

FIG. 9C. CDH26 domain structure prediction was performed by subjecting its primary amino acid sequence to SMART analysis. The positions of the signal peptide, cadherin domains, and transmembrane domain identified by this analysis are indicated (top). To identify the putative beta-catenin binding domain within CDH26, CDH1 and CDH26 primary amino acid sequences were aligned. The specific residues corresponding to the beta-catenin binding domain of CDH1 were identified, and the corresponding amino acids within CDH26 are shown. Underlining indicates identical or similar amino acids (bottom).

Figure 9D:
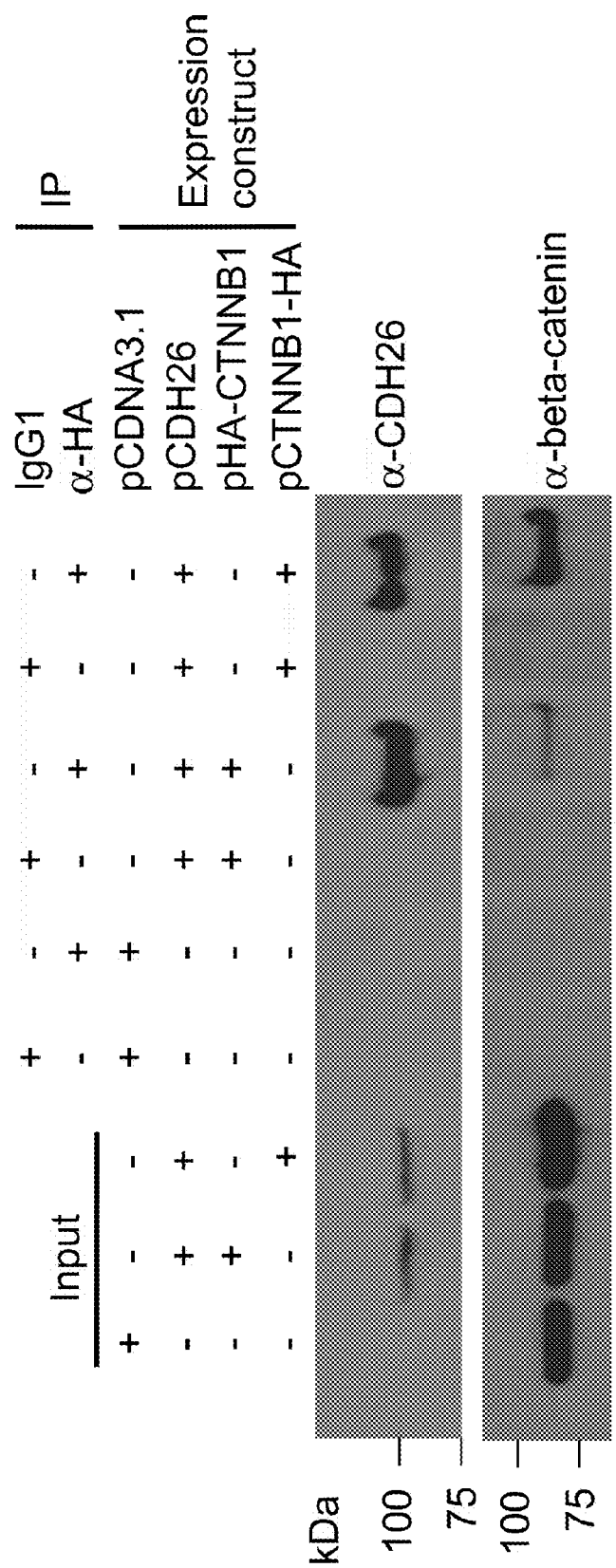
Figure 9E:
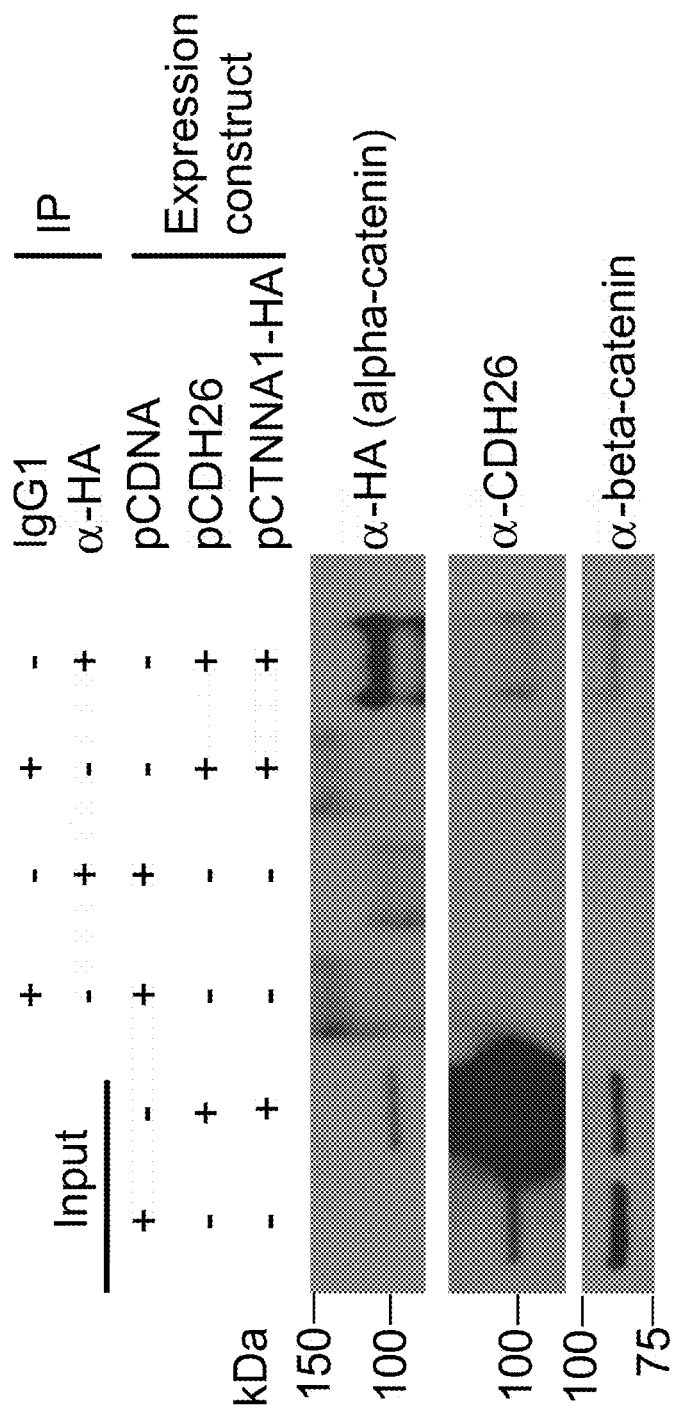
Figure 9F:
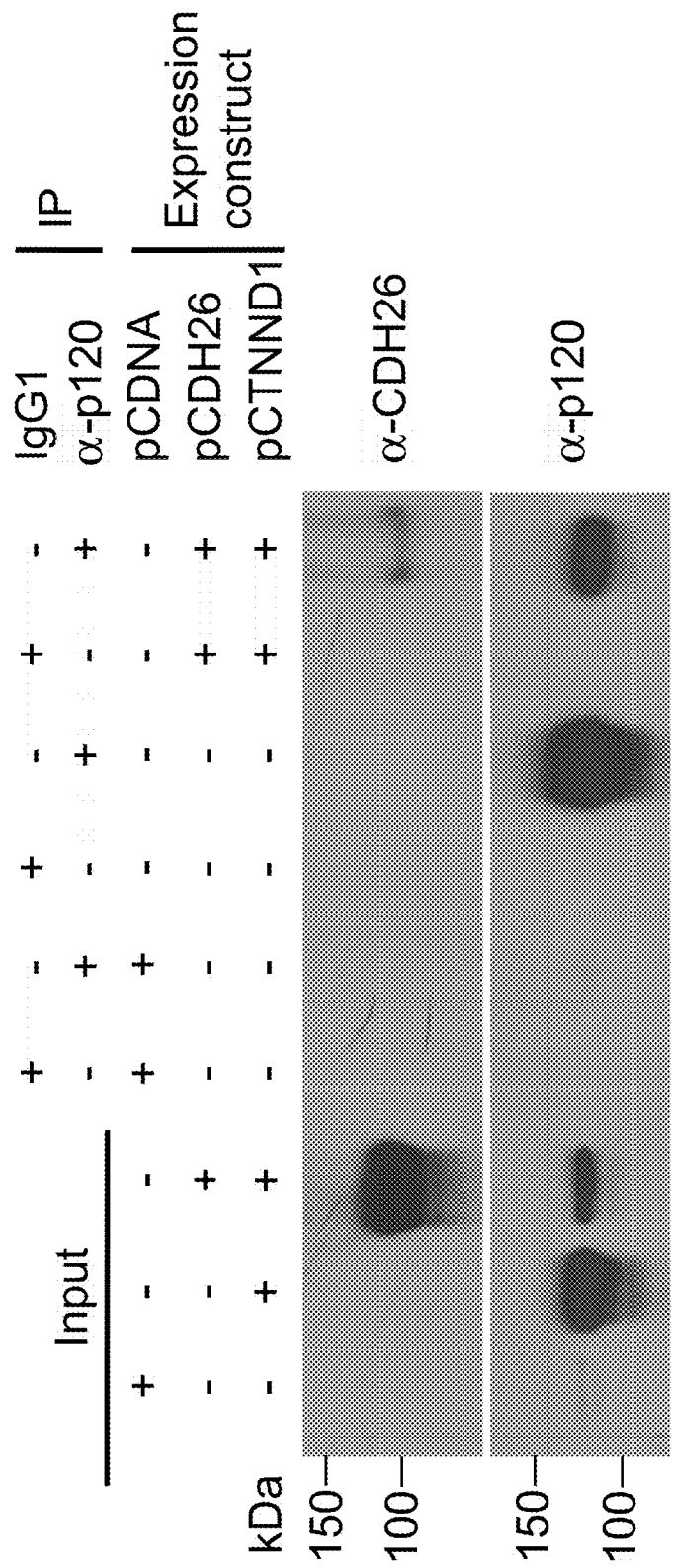

FIG. 9D. HEK 293T cells were transiently transfected with the indicated constructs. Total cell lysates were then prepared and equal amounts of protein were subjected to immunoprecipitation using the indicated antibodies. Inputs (1/10 of the amount used for IP) and immunoprecipitates were subjected to SDS-PAGE and western blot analysis with the indicated antibodies.

FIG. 9E. HEK 293T cells were transiently transfected with the indicated constructs. Total cell lysates were then prepared, and equal amounts of protein were subjected to immunoprecipitation using the indicated antibodies. Inputs (1/10 of the amount used for IP) and immunoprecipitates were subjected to SDS-PAGE and western blot analysis with the indicated antibodies.

FIG. 9F. HEK 293T cells were transiently transfected with the indicated constructs. Total cell lysates were then prepared and equal amounts of protein were subjected to immunoprecipitation using the indicated antibodies. Inputs (1/10 of the amount used for IP) and immunoprecipitates were subjected to SDS-PAGE and western blot analysis with the indicated antibodies.

Example 16

Effect of CDH26 on Eosinophil Transmigration

A study was designed to determine whether an increased amount of CDH26 expressed on the surface of cells could impact the transmigration of eosinophils through such cells. Peripheral blood eosinophils isolated from normal donors were placed in the upper chamber of transwells that were coated with either HEK 293T cells transduced with a control vector (pMIRNA1-puro-control) or with a CDH26 expression vector (pMIRNA1-puro-CDH26).

Figure 10A:
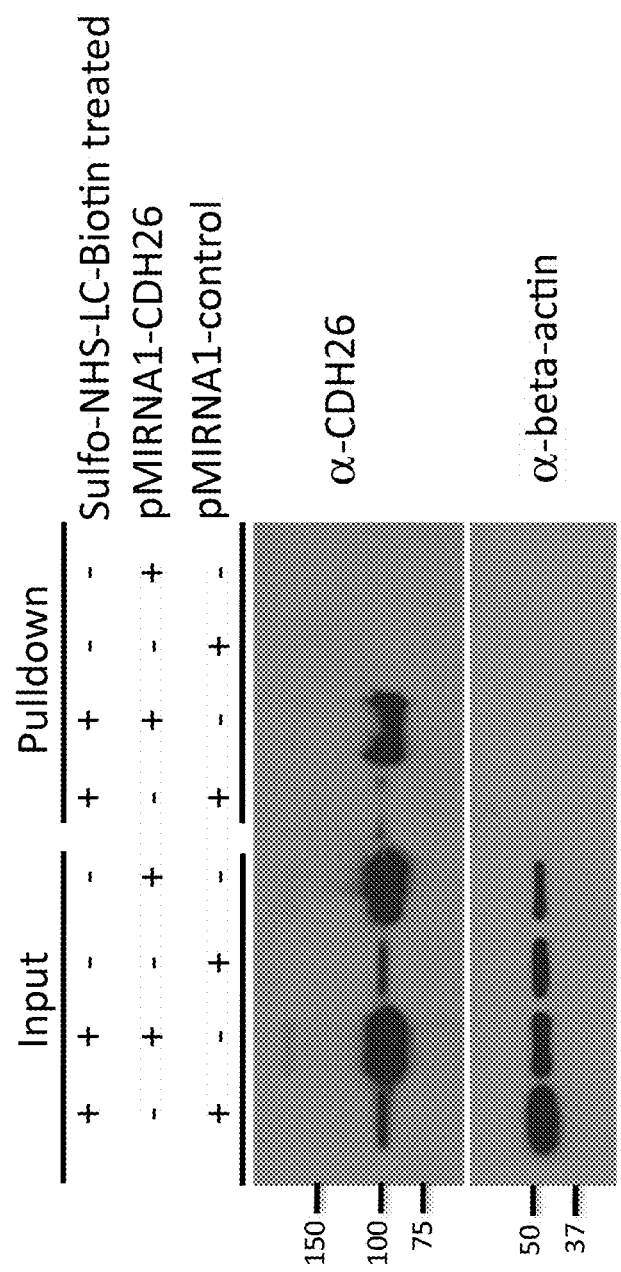
FIGS. 10A-C depict characterization of CDH26 localization in HEK 293T cells transduced with either pMIRNA1-puro-control or pMIRNA1-puro-CDH26.
Figure 10B:
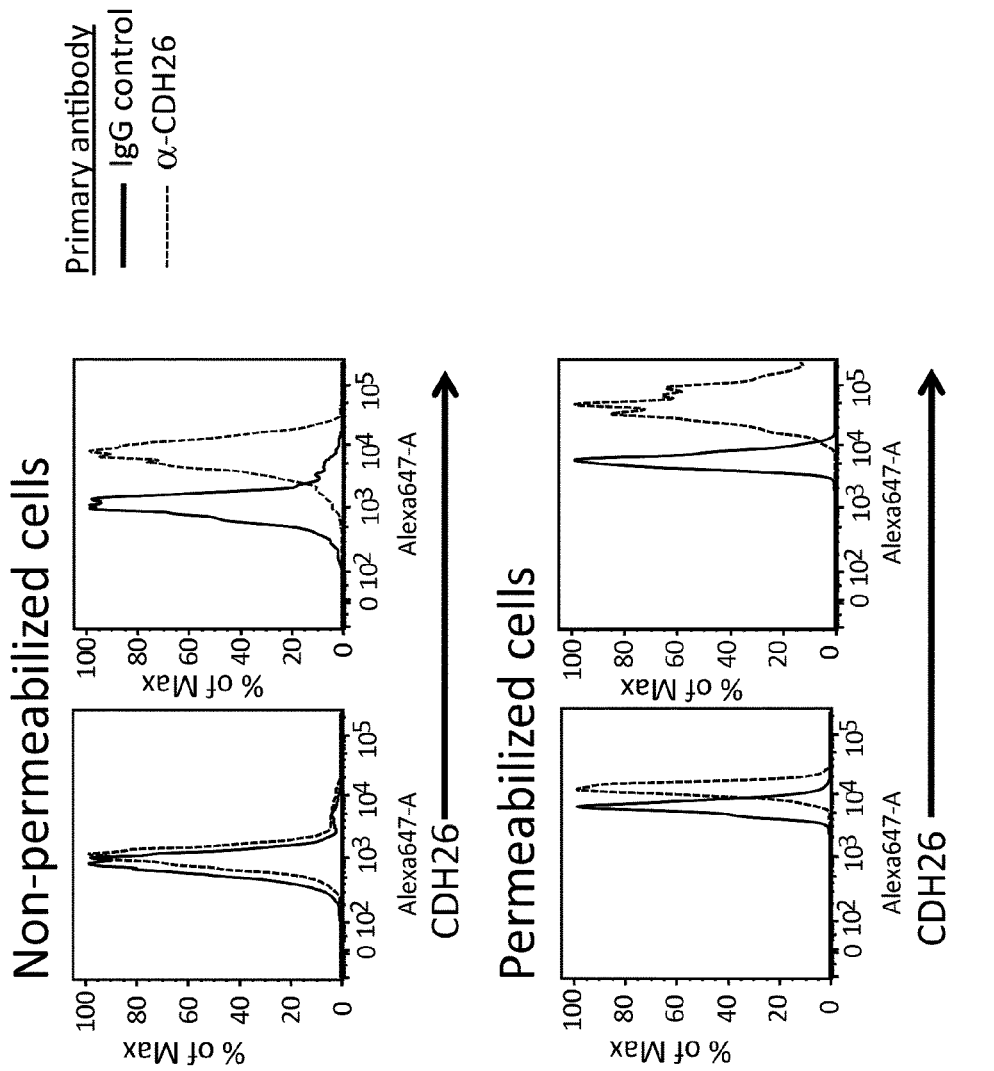
Figure 10C:
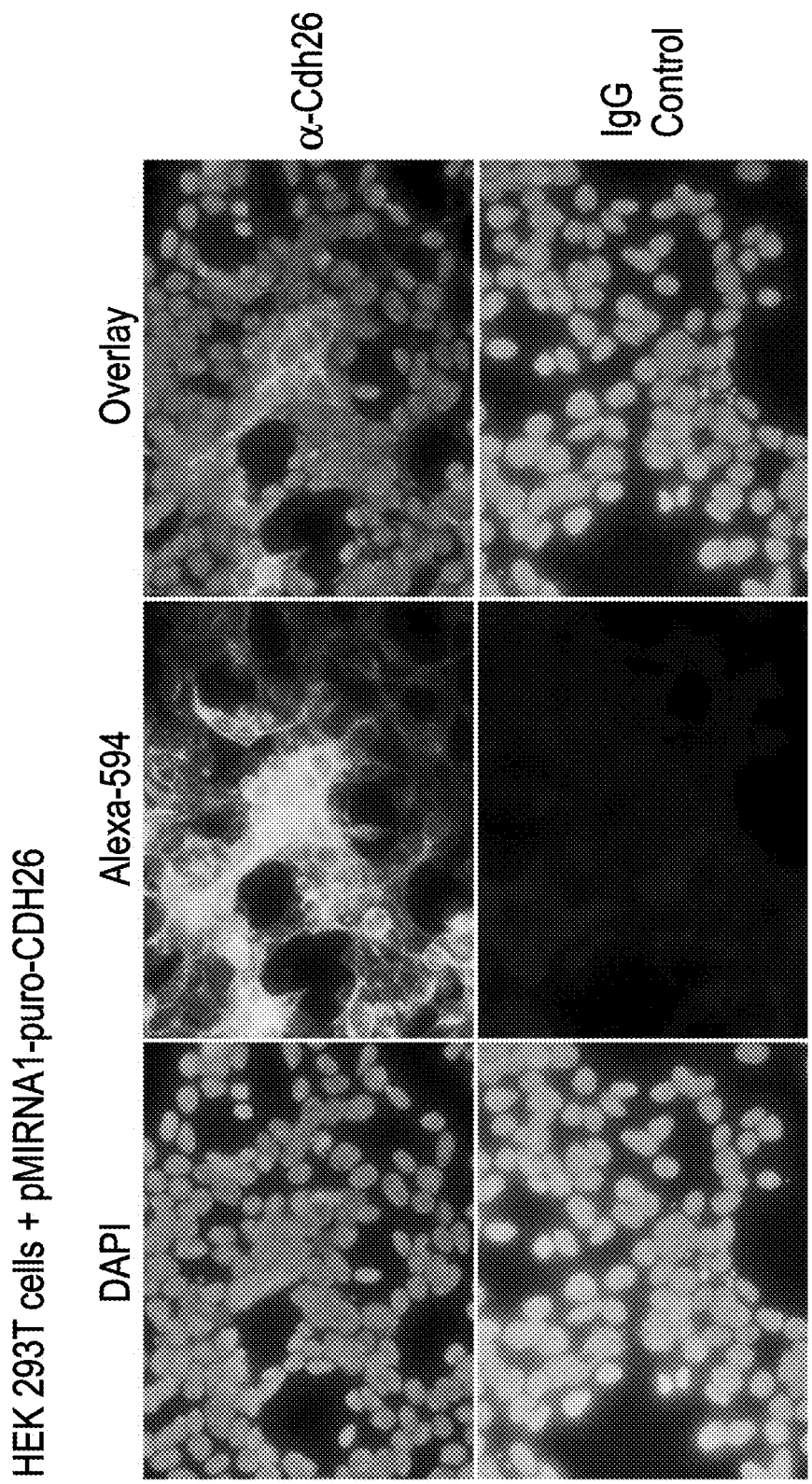
Figure 11:
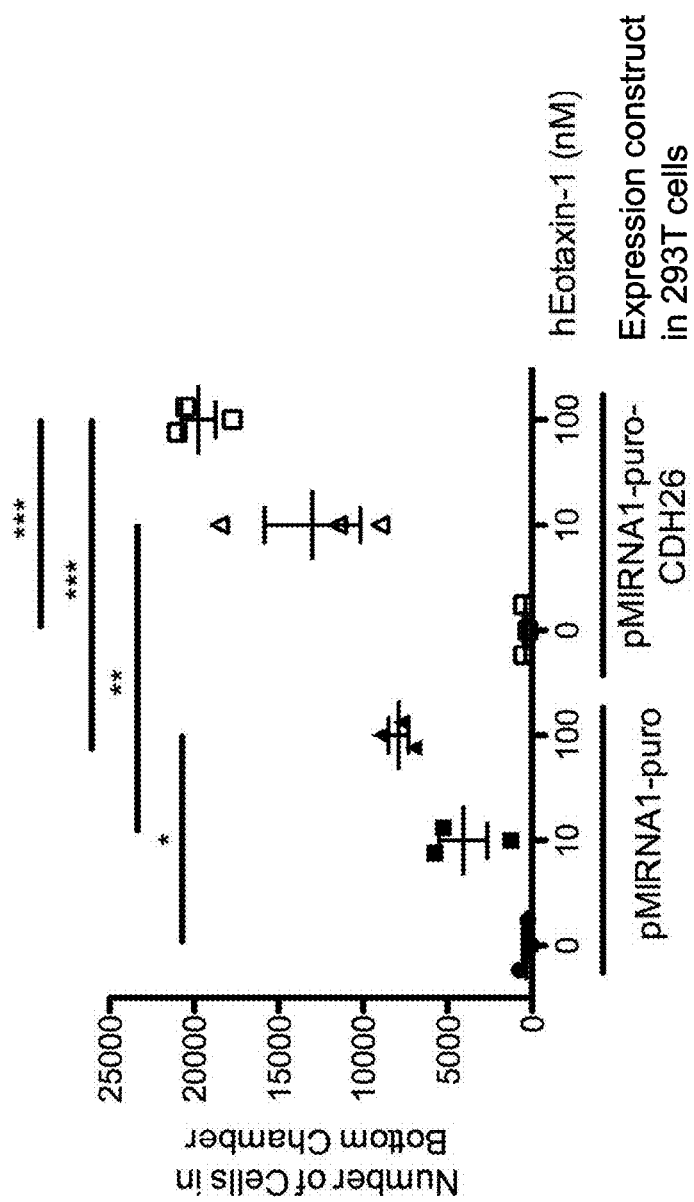
FIG. 11 depicts the impact of CDH26 on eotaxin-1-mediated eosinophil transmigration through a cell monolayer.

HEK 293T cells transduced with the CDH26 expression construct showed a high degree of CDH26 protein expression, a portion of which was localized to the surface of the cells (FIGS. 10A-C). Transmigration of the eosinophils toward the indicated amount of eotaxin-1 was monitored. In control cells, eosinophils migrated toward eotaxin-1 in a dose-dependent manner. This migration was enhanced for the same dose of eotaxin-1 through cells that were overexpressing CDH26 compared to control cells (FIG. 11).

Figure 12:
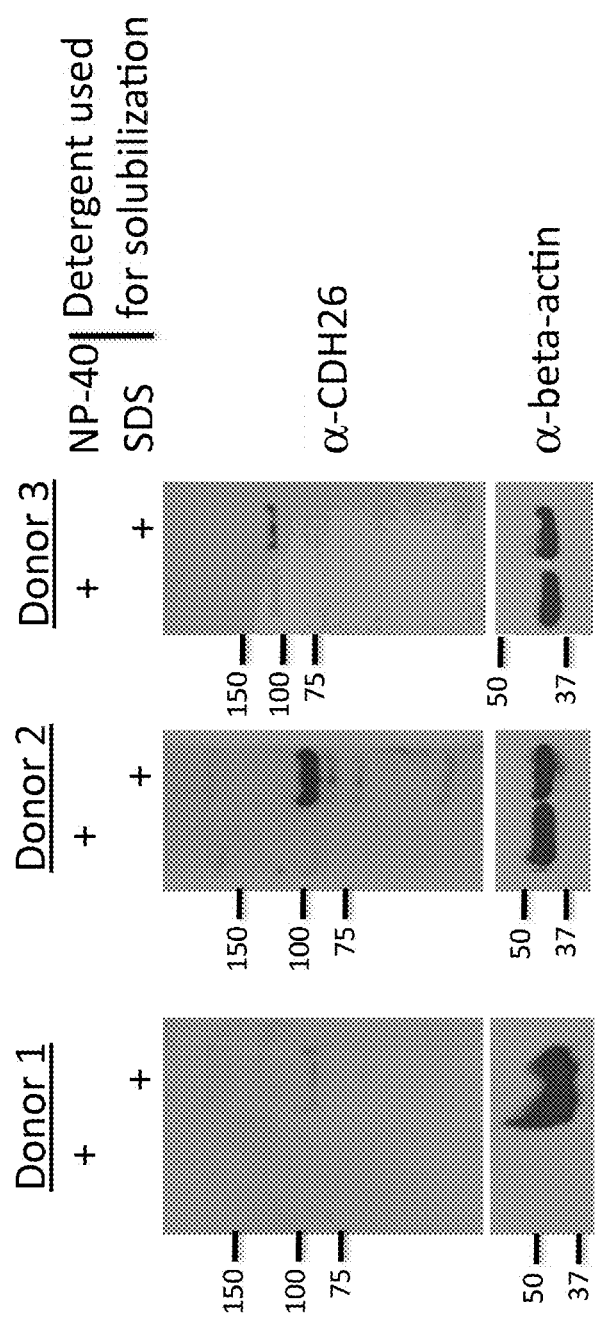
FIG. 12 depicts CDH26 protein expression by eosinophils.

Since leukocytes have been described to express cadherin proteins, a follow-up study was designed to determine whether eosinophils expressed CDH26. Western blot was performed, and revealed that peripheral blood eosinophils showed expression of CDH26 in an SDS-soluble fraction (FIG. 12).

FIG. 10A. Cells were treated with sulfo-NHS-LC-biotin to biotinylate surface proteins. Biotinylated proteins were pulled down with streptavidin-conjugated agarose beads, and total protein (input) and proteins that were pulled down were subjected to SDS-PAGE and western blot analysis for CDH26 and beta-actin.

FIG. 10B. Cells were either fixed or both fixed and permeabilized, followed by staining with either anti-CDH26 or an equivalent amount of IgG control antibody. After incubation with Alexa 647-conjugated secondary antibody, cells were subjected to FACS analysis to detect Alexa 647 signal.

FIG. 10C. Cells were acetone-fixed and then stained with either anti-CDH26 or an equivalent amount of IgG control antibody. Cells were subsequently incubated with Alexa 594-conjugated secondary antibody. The Alexa 594 signal was visualized by immunofluorescence microscopy (magnification=800×).

FIG. 11. The impact of CDH26 on eotaxin-1-mediated eosinophil transmigration through a cell monolayer is shown. HEK 293T cells transduced with either a control or CDH26-overexpression lentiviral construct were seeded on the top of transwells, and eosinophils were added to the top chamber, while media containing the indicated concentration of eotaxin-1 was added to the bottom chamber of the transwells. After 1.5 hours, the number of eosinophils present in the bottom chamber was counted.

FIG. 12. CDH26 protein expression by eosinophils is shown. Peripheral blood eosinophils were isolated from normal donors. Cells were solubilized in IP buffer containing NP-40 detergent. The NP-40 insoluble fraction was then solubilized in SDS-containing Laemmli buffer. The fractions were subjected to SDS-PAGE and western blot analysis for CDH26 and beta-actin. Results from three separate donors are shown.

Example 17

Results of Elevated CDH26 Cell Surface Expression

A study was designed to determine whether an increased amount of CDH26 expressed on the surface of cells could impact the cell adhesion properties of such cells. A related study was designed to determine whether an increased amount of CD1H26 expressed on the surface of cells could impact the IL-13-mediated production of eotaxin-3 by such cells.

Aggregation Assay

HEK 293T cells that were transduced with either pMIRNA1-puro-control or -CDH26 were used in an aggregation assay. Cells were grown to confluency and then dispersed with 0.1% trypsin in the presence of 5 mM $Ca^{2+}$, which renders the extracellular domain of cadherins resistant to trypsin-mediated proteolysis. Single cells ($2\times10^6$) were then resuspended in buffer (0.01 M HEPES in saline) either containing or lacking 1 mM $CaCl_2$ and incubated rotating at 37° C. for 30 minutes. The number of cell particles was then quantified for each sample. The results were expressed as aggregation index, defined as (initial particle number−final particle number)/initial particle number.

Eotaxin-3 ELISA

Quantification of eotaxin-3 (CCL26) protein in cell supernatants was carried out using a sandwich ELISA method according to the manufacturer's protocol (R&D Systems, Minneapolis, Minn.). Wells of half-area polystyrene plates (Costar) were coated overnight at room temperature with capture antibody suspended in PBS (1.0 µg/ml). Plates were then washed 3 times with wash buffer (PBS plus 0.05% Tween-20) and incubated with blocking buffer (1% BSA, 0.5% sucrose, 0.05% $NaN_3$) for 1 hour at room temperature. Plates were then washed 3 times with wash buffer followed by addition of standards and supernatant samples for 2 hours at room temperature. Plates were then washed 3 times with wash buffer, and detection antibody suspended in reagent diluent (1% BSA in PBS) at a concentration of 250 ng/ml was added for 2 hours at room temperature. Plates were washed 3 times with wash buffer followed by addition of streptavidin-HRP (1:200 dilution in reagent diluent). Plates were washed, a 1:1 mixture of $H_2O_2$ and tetramethylbenzidine (TMB) substrate was added, and the reaction was stopped with 2N $H_2SO_4$. Absorbance was measured at 450 nm and 900 nm.

Protein Domain Prediction and Amino Acid Sequence Alignment

Figure 13A:
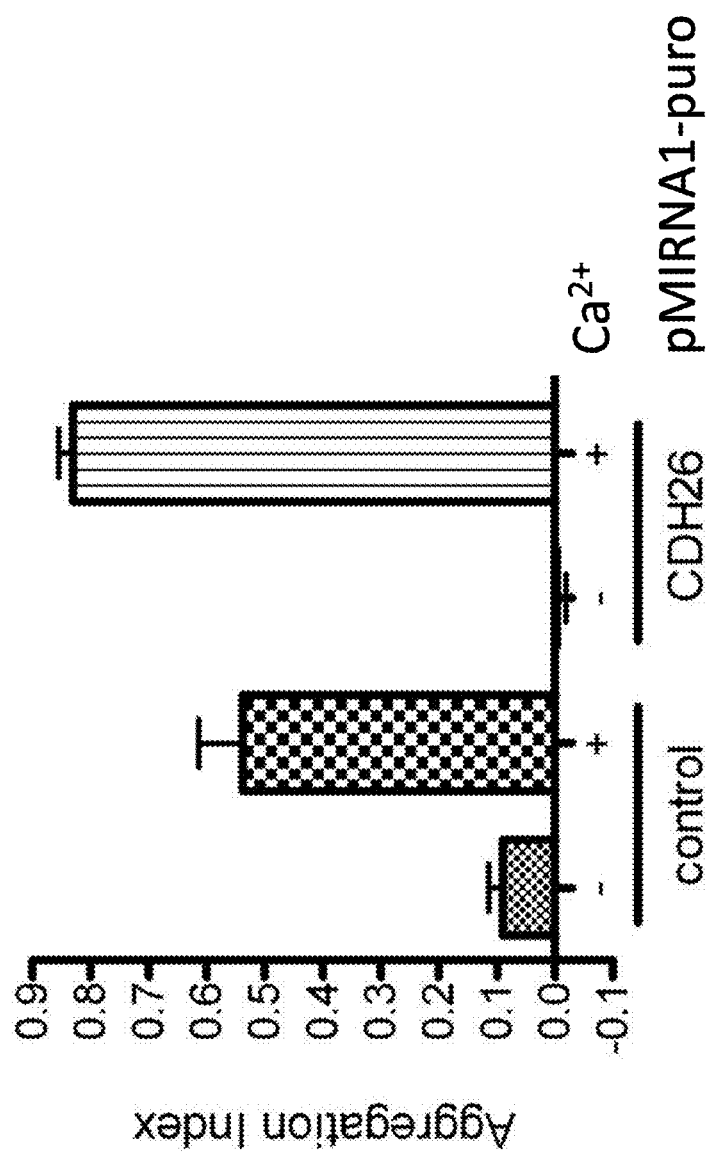
FIGS. 13A-B depict results of CDH26 cell surface overexpression.
Figure 13B:
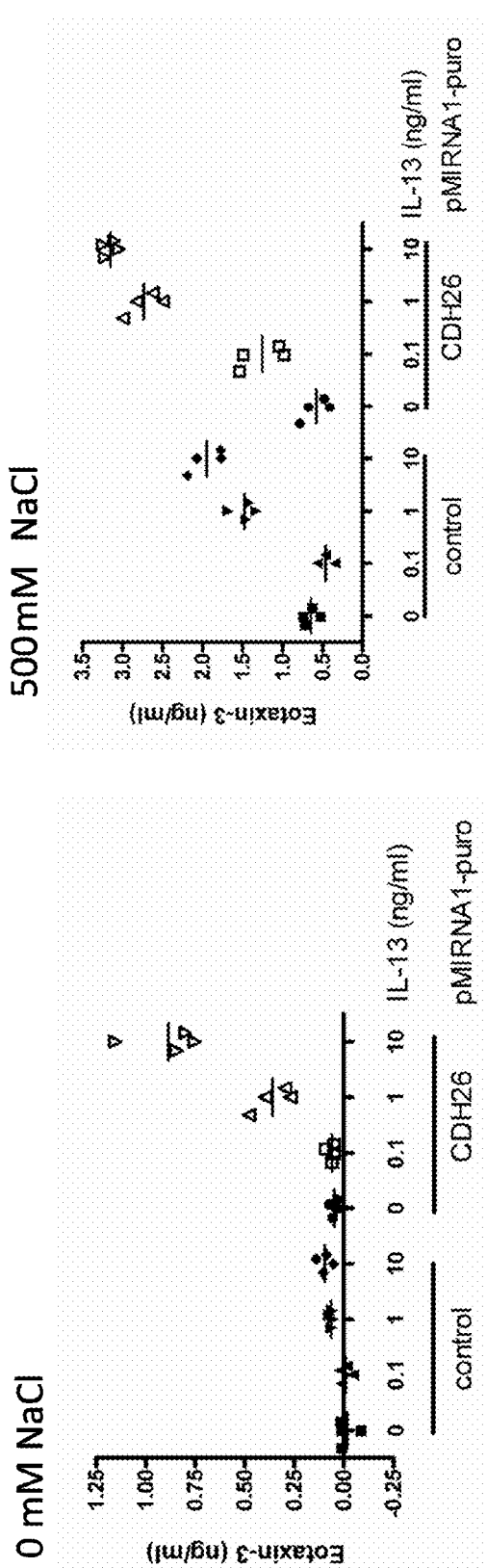

CDH26 primary amino acid sequence was subjected to SMART analysis to identify its putative domain structure (Schultz, et al. Proc. Natl. Acad. Sci. 95:5857-64 (1998); PNAS; Letunic, et al. *NAR* 40:D302-5, (published online 2012)). CDH1 (E-cadherin) and CDH26 primary amino acid sequence were aligned using the Pairwise Align Protein function followed by the Color Align Conservation function of the Sequence Manipulation Suite (Stothard, *Biotechniques* 28:1102-4 (2000)). The specific residues corresponding to the beta-catenin binding domain of CDH1 were identified (Stappert and Kemler, *Cell Adhes. Commun.* 2:31-27 (1994)) and the corresponding amino acids within CDH26 are shown Results The aggregation index of cells expressing a high amount of CDH26 was found to be significantly increased compared to that of control cells (FIG. 13A). TE-7 cells that were transduced with either pMIRNA1-puro-control or -CDH26 were grown to confluency and then treated with increasing doses of IL-13 for 72 hours. After this time, half of the supernatant was collected, and sodium chloride was added to the remaining supernatant to a concentration of 500 mM in order to disrupt non-covalent interactions between eotaxin-3 and molecules on the cell surface. The eotaxin-3 concentration in both sets of supernatants was determined by ELISA. TE-7 cells that were expressing high levels of CDH26 showed increased eotaxin-3 levels in the supernatant either with or without the addition of sodium chloride compared to control-transduced cells treated with the equivalent dose of IL-13 (FIG. 13B).

FIG. 13A. HEK 293T cells were transduced with either pMIRNA1-puro-control or -CDH26. Cells were grown to confluency and then dispersed with 0.1% trypsin in the presence of 5 mM $CaCl_2$. Single cells ($2\times10^6$) were resuspended in buffer either containing or lacking 1 mM $CaCl_2$ and then rotated for 30 minutes at 37° C. The number of cell aggregates was then quantified, and the aggregation index was calculated FIG. 13B. TE-7 cells were transduced with either pMIRNA1-puro-control or -CDH26. Cells ($7.5\times10^5$ per well) were plated in 24-well plates for 3 days. Cells were then treated with the indicated dose of IL-13 for 72 hours. Half of the supernatant per well was then collected. Sodium chloride was then added to a final concentration of 500 mM per well, and the remaining supernatant was immediately removed. Eotaxin-3 levels in supernatants without (top) or with (bottom) sodium chloride addition were then quantified by ELISA.

Example 18

Role of CDH26 3' Untranslated Region in Regulation of CDH126 Protein Levels

In primary esophageal epithelial cells, TE-7 cells, and NCI-N87 cells, CDH26 transcript levels are increased following IL-13 stimulation, but a corresponding increase in protein production is not observed. To determine whether the 3' untranslated region (UTR) of the CDH26 transcript regulates protein levels, the CDH26 3' UTR was analyzed to identify consensus sequences that had previously been shown to influence mRNA stability or protein translation.

Cell Transfection

TE-7 cells were plated at a density of 75,000 cells per well in 24-well plates. The next day, cells were transfected with 500 ng of a pGL3P-based expression construct encoding Firefly luciferase and 62.5 ng of pHRL-TK, encoding *Renilla* Luciferase Under the control of a constitutive promoter (Promega) using Trans-IT reagent (Mirus Bio, Madison, Wis.), according to the manufacturer's instructions. After 48 hours, cells were harvested with 1× passive lysis buffer (Promega), and the Firefly and *Renilla* luciferase activities were measured using Dual Luciferase Reporter Assay reagents (Promega) and a GloMax luminometer (Promega).

Plasmid Construction

For luciferase assays, pGL3P was obtained from Promega. The DNA fragment located between the XbaI and BamHI sites was removed by restriction digest, and the remaining plasmid backbone was then treated with Klenow polymerase and ligated to form pGL3P-Xba/Bam. pGL3P-CDH26 was constructed by inserting a PCR product that included the CDH26 3' UTR sequence into the SalI site of pGL3P-Xba/Bam. pGL3P-GAIT1del, pGL3P-GAIT2del, and pGL3P-GAIT3del were each constructed by deleting the specific nucleotides from pGL3P-CDH26 that correspond to the relevant GAIT element as denoted in FIG. 13A using a PCR-mediated method. pGL3P-GAIT123del was constructed by deleting the specific nucleotides from pGL3P-CDH26 that correspond to all three GAIT elements as denoted in FIG. 13A using a PCR-mediated method.

Results

Three gamma-interferon-activated inhibitor of translation (GAIT) consensus sequences were identified (FIG. 14A). Luciferase assays were performed to assess the contribution of these elements to regulation of protein levels by the CDH26 3' UTR. TE-7 cells transfected with pGL3P, which contains Firefly luciferase cDNA downstream of the SV40 promoter and upstream of SV40 late poly(A) signal, showed a high level of luciferase activity compared to the same construct that lacked the SV40 late poly(A) signal (pGL3P-Xba/Bam).

Insertion of the CDH26 3' UTR sequence into pGL3P-Xba/Bam (pGL3P-CDH26) showed decreased luciferase activity compared to the construct lacking any 3' UTR sequence. However, deletion of any single GAIT consensus sequence within pGL3P-CDH26 resulted in increased luciferase activity (FIG. 14B); therefore, these sequences have activity that inhibits protein levels.

FIG. 14A. The CDH26 3' UTR sequence was subjected to analysis using RegRNA (Huang, et al., *NAR* 34:W429-W434 (2006)), and three gamma-interferon-activated inhibitor of translation (GAIT) consensus sequences were identified. These sequences were arbitrarily numbered 1, 2, and 3 and called GAIT1, GAIT2, and GAIT3, respectively, based on their order from 5' to 3' within the 3' UTR. GAIT1 and GAIT2 are shown in bold text, and GAIT3 is underlined.

Figure 14B:
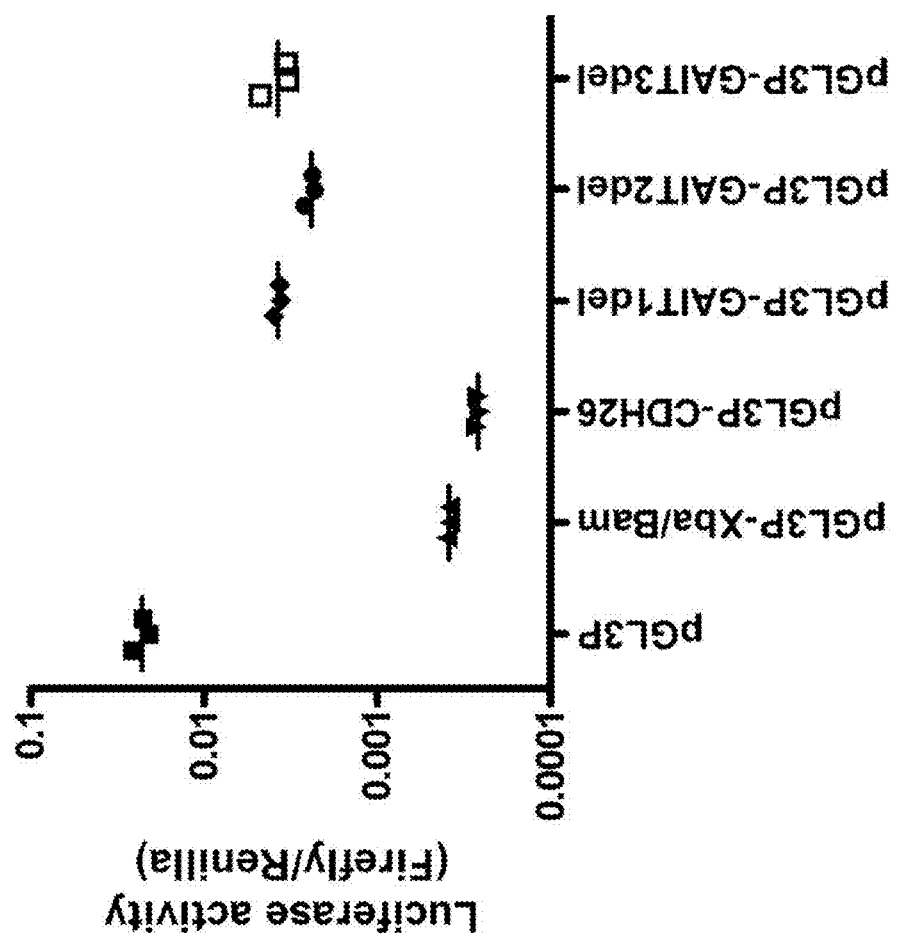

FIG. 14B. TE-7 cells were transiently transfected with the indicated Firefly luciferase expression construct. Cells were co-transfected with equivalent amounts of pHRL-TK plasmid as a control. After 48 hours, cell lysates were harvested, and both Firefly and *Renilla* luciferase activities were monitored. The ratio of Firefly to *Renilla* luciferase for each sample is graphed.

Example 19

Diagnosis of a Patient for Eosinophilic Gastritis

As described herein, gastric tissue of patients with EG was found to exhibit a conserved pattern of gene expression. A conserved set of 28 genes were found to be upregulated, and 76 genes were found to be downregulated in gastric tissue of patients with active EG compared to control patients, representing an EG transcriptome that can be used for providing a diagnosis of EG. Such a diagnosis can be used to distinguish EG from a normal condition in a patient.

The diagnostic method is carried out on a patient to determine if the patient has EG. RNA extraction is performed on a patient gastric biopsy tissue sample. After RNA quantity/quality measurement by nanodrop, 1000 ng of the RNA sample is measured for the reverse transcription (RT) reaction. cDNA corresponding to 500 ng RNA or mRNA directly is analyzed for expression of at least one of the genes, or a subset of the genes or all of the genes, as listed in Tables 9 and 10, as a single or multiplex format using at least one of a variety of gene quantification techniques, such as, for example, Taqman (Life Technologies, Carlsbad, Calif.), Light-Cycler (Roche Applied Science, Penzberg, Germany), ABI fluidic card (Life Technologies), NanoString® (NanoString Technologies, Seattle, Wash.), and the like. The data is analyzed to determine expression levels of the markers as disclosed herein to establish an EG diagnosis, which serves as the basis for the final diagnostic report.

Example 20

Diagnosis of a Patient for EG (as Distinguished from other Eosinophilic or Inflammatory GI Disorders)

In addition to EG and EoE, there are a number of additional eosinophilic gastrointestinal disorders (EGIDs), including eosinophilic duodenitis (ED), eosinophilic jejunitis (EJ), eosinophilic ileitis (EI), and eosinophilic colitis (EC), and the like (Rothenberg, M. *J. Allergy Clin. Immunol.* 113:11-28 (2004); Talley, N. et al. *Gut* 31:54-8 (1990)). There are also several other inflammatory gastrointestinal disorders, such as celiac disease and inflammatory bowel disease, *H. pylori* gastritis, non-steroidal anti-inflammatory drug (NSAID)-induced gastritis, and the like. As described herein, the molecular signature of normal and EG patients was determined, and the resulting eosinophilic gastritis molecular diagnostic panel forms a solid and consistent basis for differential diagnosis.

The diagnostic method is carried out on a patient to determine if the patient has EG instead of other esophageal disorders, such as EoE. RNA extraction is performed on a patient gastric biopsy tissue sample. After RNA quantity/quality measurement by nanodrop, 1000 ng of the RNA sample is measured for the reverse transcription (RT) reaction. cDNA corresponding to 500 ng RNA or mRNA directly is analyzed for expression of at least one of the genes, or a subset of the genes or all of the genes, as listed in Tables 9 and 10, as a single or multiplex format using at least one of a variety of gene quantification techniques, such as, for example, Taqman, Light-Cycler, ABI fluidic card, NanoString, and the like. The data is analyzed to determine expression levels of the markers as disclosed herein to establish an EG diagnosis, which serves as the basis for the final diagnostic report, thereby allowing EG to be differentiated from other EGIDs and inflammatory GI disorders in the patient.

Example 21

Evaluation of an EG Patient to Provide a Prognosis and Guidance on Selection and Modification of EG Medication and Treatment Protocols The EG diagnostic panel as described herein can be used as a personal medicine prediction device. Based on the molecular profile for each EG patient, personalized medicine can be performed to enhance treatment efficiency. The diagnostic panel can be used as an accurate, rapid, informative, and low-cost diagnosis based on the EG transcriptome and can be used alone or in conjunction with a histological diagnosis.

A molecular understanding of the pathogenesis of EG can also improve the mechanistic study of EG that can ultimately be used to provide prognosis and/or personalized treatments based on the unique expression of each patient. Such personalized treatments include guidance for determining appropriate medication dosages or treatment protocols to use in a given patient. Personalized treatment also allows for the modification of medication dosage or treatment protocols as necessary.

The diagnostic method is carried out on a patient to determine if the patient has eosinophilic gastritis (EG). RNA extraction is performed on a patient gastric biopsy tissue sample. After RNA quantity/quality measurement by nanodrop, 1000 ng of the RNA sample is measured for the reverse transcription (RT) reaction. cDNA corresponding to 500 ng RNA or mRNA directly is analyzed for expression of at least one of the genes, or a subset of the genes or all of the genes, as listed in Tables 9 and 10, as a single or multiplex format using at least one of a variety of gene quantification techniques, such as, for example, Taqman, Light-Cycler, ABI fluidic card, NanoString, and the like. The data is analyzed to determine expression levels of the markers as disclosed herein to establish an EG diagnosis, which serves as the basis for the final diagnostic report. Based on the final diagnostic report, prognosis is provided, and/or a specific therapy is developed, and/or an ongoing therapy is modified, based upon the specific EG transcription profile generated for the patient.

Example 22

Evaluation of an Archived Sample from a Patient

As described herein, the eosinophilic gastritis diagnostic panel has the capacity to differentiate the EG and NL transcriptome from formalin-fixed, paraffin-embedded (FFPE) samples. While FFPE samples are normally associated with relatively degraded RNA due to oxidation degradation during archiving (April, et al. *PloS One* 4:e8162 (2009)), the data presented herein indicate that the EG diagnostic panel is practically tolerant to the poor RNA integrity of FFPE samples. With RNA extraction from FFPE samples becoming a more readily available technique, molecular diagnosis from FFPE biopsy samples will allow for the retrospective study of the large amount of archived FFPE samples in various institution. FFPE samples are also normally associated with longer follow-up and more clinical outcomes, rendering them suitable for a long-term clinical study focusing on prognosis.

The FFPE capacity of the eosinophilic gastritis molecular diagnostic panel as disclosed herein can make long term retrospective study possible without recruiting new samples. In addition, since FFPE sections can be sent at ambient temperature and are relatively less sensitive to decay, multi-centered studies can be performed in a more convenient manner in terms of logistics. The usage of already obtained clinical biopsy specimens combined with the merits of molecular diagnosis can reduce the number of biopsies procured during endoscopy.

Example 23

Determination of EDP Genes Targeted by Therapeutics

The eosinophilic gastritis diagnostic panel, as described herein, can be used to determine if a particular drug is engaging a specific target on the eosinophilic gastritis diagnostic panel. For example, the eosinophilic gastritis diagnostic panel can be used to determine if an therapy specific for a molecule involved in EG disease pathogenesis up- or down-regulates the related marker or gene within the EDP.

The diagnostic method is carried out on a patient to determine the genes of the eosinophilic gastritis diagnostic panel with which a particular therapeutic is interacting. RNA extraction is performed on an esophageal biopsy tissue sample from a patient to whom a therapeutic has been administered. After RNA quantity/quality measurement by nanodrop, 1000 ng of the RNA sample is measured for the reverse transcription (RT) reaction. cDNA corresponding to 500 ng RNA or mRNA directly is analyzed for expression of at least one of the genes, or a subset of the genes or all of the genes, as listed in Tables 9 and 10, as a single or multiplex format using at least one of a variety of gene quantification techniques, such as, for example, Taqman, Light-Cycler, ABI fluidic card, NanoString, and the like. The data is analyzed to determine expression levels of the markers as disclosed herein to establish an EG diagnosis, which serves as the basis for the final diagnostic report. The result set is evaluated to identify from the result set the genes that are up- or down-regulated in response to the therapeutic.

Example 24

Determination of a Patient's Allergic Status

As described herein, CDH26 represents a marker or gene that is associated with EG, EoE, and allergic inflammation in general. Accordingly, CDH26 can be used as a marker to determine the allergic status of a patient. In such a determination of a patient's allergic status, CDH26 can be used alone or in combination with other genes found to be associated with EG or EoE.

The diagnostic method is carried out on a patient to determine if the patient has an allergic inflammatory condition. RNA extraction is performed on an esophageal biopsy tissue sample from a patient to whom a therapeutic has been administered. After RNA quantity/quality measurement by nanodrop, 1000 ng of the RNA sample is measured for the reverse transcription (RT) reaction. cDNA corresponding to 500 ng RNA or mRNA directly is analyzed for expression of CDH26 using at least one of a variety of gene quantification techniques, such as, for example, Taqman, Light-Cycler, ABI fluidic card, NanoString, and the like. The data is analyzed to determine the patient's expression level of CDH26 to establish an allergic inflammatory condition diagnosis, which serves as the basis for the final diagnostic report.

Example 25

Treatment of a Patient with an Allergic Inflammatory Condition

As described herein, CDH26 was found to be highly over-expressed in allergic inflammatory conditions. Accordingly, anti-CDH26-based therapeutics that block or inhibit CDH26 activity can be used to treat patients with EG, EoE, or other allergic inflammatory conditions.

A subject is diagnosed as having an allergic inflammatory condition. Such a diagnosis can be made, for example, according to the process described in Example 24. An anti-CDH26-based therapeutic, such as a CDH26-Fc fusion protein, a CDH26 anti-sense polynucleotide, a CDH26-directed miRNA, a CDH26-directed shRNA, a CDH26-directed humanized antibody, a CDH-related peptide, a catenin-based inhibitor, a compound or composition that targets a binding site and/or protein of at least one GAIT consensus sequence within a CDH26 3' UTR, or the like, is administered to the subject. Following administration, CDH26 activity in the subject is suppressed, resulting in reduced allergic inflammation, thereby alleviating symptoms associated with the allergic inflammatory condition.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of determining an eosinophilic gastritis (EG) status in a subject, wherein the status comprises distinguishing EG from a normal condition defined as the absence of eosinophilic gastrointestinal disease or from eosinophilic esophagitis (EoE), the method comprising:
applying a gastric tissue sample from the subject to a diagnostic panel for detecting at least one marker or gene selected from Table 9 and/or Table 10, the at least one marker or gene being Dual oxidase 2 ("DUOX2", SEQ ID NO: 5), to obtain a result;
analyzing the result to determine a level of expression of the at least one marker or gene; and
determining the EG status of the subject based upon the level of expression,
wherein an increased level of DUOX2 expression indicates a status of EG as distinguished from the normal condition or EoE, and wherein an increased expression of any additional markers or genes selected from Table 9, and/or a decreased expression of any additional markers or genes selected from Table 10, indicates a status of EG as distinguished from the normal condition or EoE.

2. The method of claim 1, wherein the diagnostic panel comprises mRNA or protein.

3. The method of claim 1, wherein the at least one marker or gene further comprises CDH26.

4. The method of claim 1, further comprising detecting a level of eotaxin-3 mRNA expression or eotaxin-3 protein expression in the sample from the subject.

5. The method of claim 3, wherein the at least one marker or gene further comprises at least 10 markers or genes from Table 9 and/or Table 10.

6. The method of claim 3, wherein the at least one marker or gene further comprises at least 20 markers or genes from Table 9 and/or Table 10.

7. The method of claim 3, wherein the at least one marker or gene further comprises at least 30 markers or genes from Table 9 and/or Table 10.

8. The method of claim 3, wherein the at least one marker or gene further comprises all of the markers or genes from Table 9 and/or Table 10.

9. The method of claim 1, wherein the expression of DUOX2 is increased at least 2-fold.

10. The method of claim 8, further comprising monitoring exposure to one or more therapeutic compounds in the subject based upon the level of expression.

11. The method of claim 8, further comprising determining the specific genes engaged by a therapeutic, wherein the therapeutic is administered to the subject, and a sample from the subject following therapeutic administration is subjected to the same diagnostic panel in order to obtain a result, wherein differences between the two results determine the specific genes engaged by the administered therapeutic.

12. The method of claim 3, further comprising treating the subject having a status of EG with an anti-CDH26-based therapeutic.

* * * * *

SEQUENCE LISTING

<160> NUMBER OF SEQ ID NOS: 141

<210> SEQ ID NO 1
<211> LENGTH: 430
<212> TYPE: DNA
<213> ORGANISM: Homo sapiens
<220> FEATURE:
<221> NAME/KEY: modified_base
<222> LOCATION: (343)..(345)
<223> OTHER INFORMATION: a, c, t, g, unknown or other
<220> FEATURE:
<221> NAME/KEY: misc_feature
<222> LOCATION: (343)..(345)
<223> OTHER INFORMATION: n is a, c, g, or t
<220> FEATURE:
<221> NAME/KEY: modified_base
<222> LOCATION: (347)..(347)
<223> OTHER INFORMATION: a, c, t, g, unknown or other
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: modified_base
<222> LOCATION: (349)..(352)
<223> OTHER INFORMATION: a, c, t, g, unknown or other
<220> FEATURE:
<221> NAME/KEY: misc_feature
<222> LOCATION: (349)..(352)
<223> OTHER INFORMATION: n is a, c, g, or t

<400> SEQUENCE: 1
gggaatcact attcagggat ttttccccctt tgctcttctt ttccctcctt aaaagaaaaa      60
ttaccttcta gtcctaggat gaggacacac tattagtttg aattaaatgc tttgatattc     120
tcagatcagc catcttgaac caaagcaaaa ccacaagtta cactttctta aaatttgatt     180
tgtcatattt tctagagaaa cttgaattta attgtgttat tcttagcttc cactggcagc     240
ctagctttga gggtaaatga aaatataacc catagattac ccagccactt gggaacagca     300
ggtaatactg aagaaaaata aaaatagatt ttgaaaacgt tannnanann nntatgatta     360
tgattctgtt ccatttaagg gaaaacttag gtaaatagag aaattttttc tataacattg     420
tgtagtcagt                                                            430

<210> SEQ ID NO 2
<211> LENGTH: 493
<212> TYPE: DNA
<213> ORGANISM: Homo sapiens

<400> SEQUENCE: 2
aggagacaac aatgtccctg ctacccgtgc catacacaga ggctgcctct ttgtctactg      60
gttctactgt gacaatcaaa gggcgaccac ttgtctgttt cttgaatgaa ccatatctgc     120
aggtggattt ccacactgag atgaaggagg aatcagacat tgtcttccat ttccaagtgt     180
gctttggtcg tcgtgtggtc atgaacagcc gtgagtatgg ggcctggaag cagcaggtgg     240
aatccaagaa catgcccttt caggatggcc aagaatttga actgagcatc tcagtgctgc     300
cagataagta ccaggtaatg gtcaatggcc aatcctctta cacctttgac catagaatca     360
agcctgaggc tgtgaagatg gtgcaagtgt ggagagatat ctccctgacc aaatttaatg     420
tcagctattt aaagagataa ccagacttca tgttgccaag gaatccctgt ctctacgtga     480
acttgggatt cca                                                        493

<210> SEQ ID NO 3
<211> LENGTH: 428

<212> TYPE: DNA
<213> ORGANISM: Homo sapiens

<400> SEQUENCE: 3

```
gtacagcaaa cagatgcgtc tacatccata cattactgtg tttggctgaa ttccactcta      60
atatgatgct ccattatgca ccatactgtg atgaccttc tactccgaaa cctgctggag      120
cctgcccttg gccgtggggt gtcagccaat cactgcttgt tccacttgtt gtacatttta      180
tttttgagtc tttttctttc tcatatacag aaaaatagta tgaaaataaa ataaatgtat      240
gaaacagtat taatgcagaa atgtgctact aatggatgtc tgagtcacca gaaattccat      300
tcttaaagag gcggttagca cctattagac gtaacagtga tgtcttttaa aaaatccaaa      360
agcatattgc aacaataagt ttgagacttt gtgtgaacaa agggaaattc agcctcttat      420
gtctttgt                                                              428
```

<210> SEQ ID NO 4
<211> LENGTH: 549
<212> TYPE: DNA
<213> ORGANISM: Homo sapiens

<400> SEQUENCE: 4

```
cttactcttc accagagcct agcaatagca agatatttga ccaaaaacac agatttggct      60
ggaaacacag aaatggaaca atgtcatgtt gatgctattg tggacactct ggatgatttc      120
atgtcatgtt ttccttgggc agagaaaaag caagatgtga aagagcagat gttcaatgag      180
ctgctcacgt ataatgcgcc tcatcttatg caagacttgg acacatattt aggggggaga      240
gaatggctta ttggtaactc tgtaacttgg gcagacttct actgggagat ttgcagtacc      300
acacttttgg tctttaagcc tgacctgtta gacaaccatc caaggctggt gactttacgg      360
aagaaagtcc aagccattcc tgccgtcgct aactggataa aacgaaggcc ccaaaccaaa      420
ctctagctga tccatgttgc cttcaagttt gttttctcg ggggcatctc tctcatcaga      480
taagacagct acatcagcct gccagataat ccacatgctc cctccccagc tccactaaga      540
ttttcactt                                                              549
```

<210> SEQ ID NO 5
<211> LENGTH: 409
<212> TYPE: DNA
<213> ORGANISM: Homo sapiens

<400> SEQUENCE: 5

```
ttagcactga aagtctcttg ccccaggaaa ccccatcagt cccaggcaga ttgggacagc      60
tggtcaccctt acgcaagagc caggctgaaa catcccctcc atactcagct ctttaacttt      120
tctttctt tttcatcggg ctcttttccta aaaagctgag ctgtaaaata ttttacatcg      180
aggtataata aataatcatg tacatgtttt accaccaccc aggtcaagac atagaatgtt      240
tcaacatttc catcaccca gaaactcccc ttgtaccccc ttccacttcg tctcccctag      300
ctcctagaag caaccactga tgtgatttct accaaatcca gttttggtcc tactaaatat      360
actctttga gactggcctc ttttactcac cataatgcct ttgtaattc                  409
```

<210> SEQ ID NO 6
<211> LENGTH: 277
<212> TYPE: DNA
<213> ORGANISM: Homo sapiens

<400> SEQUENCE: 6

| | |
|---|---|
| gcacctgagc atgaaactcg acgcgttctt cggcatcttc tttggggccc tgggcggcct | 60 |
| cttgctgctg ggggtcggga cgttcgtggt cctgcgcttc tggggttgct ccggggccag | 120 |
| gttctcctat ttcctgaact cagctgaggc cttgccttga aggggcagct gtggcctagg | 180 |
| ctacctcaag actcacctca tccttaccgc acatttaagg cgccattgct tttgggagac | 240 |
| tggaaaaggg aaggtgactg aaggctgtca ggattct | 277 |

<210> SEQ ID NO 7
<211> LENGTH: 455
<212> TYPE: DNA
<213> ORGANISM: Homo sapiens

<400> SEQUENCE: 7

| | |
|---|---|
| taagtgtcga gggaccatgc cagcaactac caaaaatctc ttaaatcttc aggtacagct | 60 |
| ggcattttgg cagatgcata gagacatctg agaccctcag aaaggaagga taatccaaga | 120 |
| atataggaaa tctgtgttct cttcctttca ttttatccct tatatttcta aagactaatt | 180 |
| ataagtaatc tgacatttta atgtagctac tcttatttat ttttttcttc tgaggtatta | 240 |
| aaatatctgg actgagtttt gccaaatgtt aaagggagaa gagttactga agactttgaa | 300 |
| cacttgcttt ttgtgattgc ttatgtcatt agtgcctcat gactgtgttt gatgtccttt | 360 |
| attgatacaa agtgagcctg tgccttcatt atcttgccca ttttaataca aatggaaacc | 420 |
| tggtgtttga aaatctctga actgtgtggg ttttg | 455 |

<210> SEQ ID NO 8
<211> LENGTH: 510
<212> TYPE: DNA
<213> ORGANISM: Homo sapiens
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: modified_base
<222> LOCATION: (97)..(97)
<223> OTHER INFORMATION: a, c, t, g, unknown or other
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: misc_feature
<222> LOCATION: (109)..(109)
<223> OTHER INFORMATION: n is a, c, g, or t

<400> SEQUENCE: 8

| | |
|---|---|
| aggatacact ccacagacag acacttctga tgatcttgac cgacccagtg aggaagtttt | 60 |
| ctctagagat ctttcagatt ttccatctct agnaaantgg catgggaanc aaatgatgaa | 120 |
| gatgaattaa gccttggttt gcccactgag ctcaagagaa agaaggaaca gttggacagt | 180 |
| ggtcacagac caagcaaaga gacgcaatca gcagctggtc tcacccttcc tctgaacagt | 240 |
| gaccaaacct ttcacctgat gagcaacctg gctggggatg ttatcacagc tgcagtgact | 300 |
| gcagctatca aagaccagtt agagggtgtg cagcaagcac tttctcaggc tgcccccatc | 360 |
| ccagaagagg acacagacac tgaagaaggt gatgactttg aactacttga ccagtcagag | 420 |

```
ctggatcaaa ttgagagtga attgggactt acacaagacc aggaagcaga agcacagcaa       480
aataagaagt cttcaggttt cctttcaaat                                        510

<210> SEQ ID NO 9
<211> LENGTH: 410
<212> TYPE: DNA
<213> ORGANISM: Homo sapiens

<400> SEQUENCE: 9
ttatgttcta agtgcctcca agttcaaaac ttattggaat gttgagagtg tggttacgaa        60
atacgttagg aggacaaaag gaatgtgtaa gtcttttaatg ccgatatctt cagaaaacct      120
aagcaaactt acaggtcctg ctgaaactgc ccactctgca agaagaaatc atgatatagc      180
tttccatgtg gcagatctac atgtctagag aacactgtgc tctattacca ttatggataa      240
agatgagatg gtttctagag atggtttcta ctggctgcca gaatctagag caaagccatc      300 cccctcctg gttggtcaca gaatgactga caaagacatc gattgatatg cttctttgtg       360
ttatttccct cccaagtaaa tgtttgtcct tgggtccatt ttctatgctt                 410

<210> SEQ ID NO 10
<211> LENGTH: 433
<212> TYPE: DNA
<213> ORGANISM: Homo sapiens

<400> SEQUENCE: 10
ctggggcata ctaccagcag ccaggaaagg agaggcagat ccgagctgca gggcacgagc       60
ctcatctgct tgctcgacag gggatcctgc tagatggtga taaaggcaag tttctgcttc      120
aggtcttcac caagtccctt tttactgagg acactttctt cctggagctg attcagaggc      180 aggggggccac tggctttggt cagggcaaca tcagagctct gtggcagtcc gtacaggagc     240
aatctgccag gagccaggaa gcctaaggat gcccagggct gggtgcagcc agctgtcctg      300
cagctctggg gagaccagca cagaactgag gaacatctgc aggaggccca actagtgaaa      360
ggctttgcct ccggggggca ggtgtgactt ccatttcatc agtgcctgcc agaagctgtg      420
tctctcattg ggc                                                         433

<210> SEQ ID NO 11
<211> LENGTH: 529
<212> TYPE: DNA
<213> ORGANISM: Homo sapiens

<400> SEQUENCE: 11
attagtgtca ttagtgtgtt ggaagagaaa tactattcag taagcttcgc caaagaaaag       60
tgagtcaaag ttaatgtgtg tgtgcattta tatgtaggca gctcgtagac cacattttag      120
ccagcaactg gtaacaaaga gcttagtttt ccttgtttga atgctgtaga tctgtaccta      180 gtaccccctcc catctactga tttgtttgtt tttgtaacca aacacatttt cagatagaag    240
gagccttaaa aaaaaaaaaa tcacattgag taacttcagt atgaatgaat gagagtgtgt      300
ggagctaccc ctcacccctcc accccttttgt gcttttttatt cccgaatttt cccagtctct   360
taaacagaaa aatgactgat ataattatct tttggaaact gagccttaat ttttttttaga     420 ggggaaata agttttcccc aactcacaca gcataagcaa tgtttgacag caatataatg      480
ccgttgtaaa ctactgagag tattgtatct gttctggtaa ccatgtaca                  529

<210> SEQ ID NO 12
```

<211> LENGTH: 277
<212> TYPE: DNA
<213> ORGANISM: Homo sapiens

<400> SEQUENCE: 12

```
taagctagtt ttctgaggtg ttttcacacg tcttttata gttacttcat cttagatttt      60
tgaagggata tgacttccta ctaaggattt agtttaccac aacaattctg actacaataa    120
gacattttga ggaggatatt tggctactgt aaacatggct ggtggaaaat cacgattgtg    180
gcttgatgtg gcaagccgaa accacttggc tctggaaatc aagttcata ctggtttaat    240
taagctctct cctgacaacc cccagaatta aatgaac                             277
```

<210> SEQ ID NO 13
<211> LENGTH: 506
<212> TYPE: DNA
<213> ORGANISM: Homo sapiens

<400> SEQUENCE: 13

```
gacagtgttg gacatgctcc gggatgccat ggtggccaaa gtcaatactt ccaaaggctt     60
cctgattgat ggctaccgc gggaggtgca gcaaggagaa gagtttgagc gacggattgg    120
acagcccaca ctgctgctgt atgtggacgc aggccctgag accatgaccc agcggctctt    180
gaaacgtgga gagaccagcg ggcgtgtgga cgacaatgag gagaccatca aaaagcggct    240
ggagacctat tacaaggcca cagaacccgt catcgccttc tatgagaaac gtggcattgt    300
gcgcaaggtc aacgctgagg gctccgtgga cagtgtcttc tcccaggtct gcacccacct    360
ggacgcccta aagtagcaac gctggagccg cttccccagc tcagagcccc gccccacccc    420
gtcctgatta gaggtcctcc tggcctgagc gcagcgcctc caccctgccc tgctgagcac    480
agacggagga agccgcttat cctgtt                                         506
```

<210> SEQ ID NO 14
<211> LENGTH: 205
<212> TYPE: DNA
<213> ORGANISM: Homo sapiens

<400> SEQUENCE: 14

```
tacactccac atcctacaga aaagcattac ccattttgcg gccaagttcc cgacgagagg     60
ctggacctct tcatcacatt gacttacgcc gttgcttttc cagactgggc agaggggctg    120
acttcgcagt gtgtgccaaa gagccggtgt ctgataatcc catttcctg cttatcacct    180
gaactgtgcc agtatcactt ttagt                                         205
```

<210> SEQ ID NO 15
<211> LENGTH: 424
<212> TYPE: DNA
<213> ORGANISM: Homo sapiens
<220> FEATURE:
<221> NAME/KEY: misc_feature
<222> LOCATION: (263)..(263)
<223> OTHER INFORMATION: n is a, c, g, or t

<400> SEQUENCE: 15

```
agaacctgtc gtaccagcat catgagctgg atgcaggagc ccatggctga aaggagttaa     60
aacgcccagt ggtcattaag tgaaacatct tttatcaacc tgcaaaagct gcagcgttct    120
ctgccaggtc aaatgggcat gtttagaaaa taagagaaga tggctgagta tagctaatga    180
ataaatggtt gtttctttag aaaattaaac acacacagag tgtaagagga gaggatacgg    240
ccctccctga aggataaagt ccncctggac ggtgccctgc cctcgcttct cacattaact    300
```

```
gcccaggaat gtcatgctga ttggttcccg aagggtgtt tggcaagggg cagtgtatgg      360
agctacgtgt agaaggagag aaatttgtgt gtggcttttg taaattttga ccgattgcag      420
caat                                                                   424
```

<210> SEQ ID NO 16
<211> LENGTH: 515
<212> TYPE: DNA
<213> ORGANISM: Homo sapiens

<400> SEQUENCE: 16

```
aggagcccag gaacgacgtg gtcttccagc ccatttccgg ggaagacgtg cgcgatgtga       60
cagccctgaa cgtgagcacg ctgaaggctt acttcagatg cgatggctac aagggctacg      120
acctggtcta cagcccccag agcggcttca cctgcgtgtc cccgtgcagt aggggctact      180
gtgaccatgg aggccagtgc cagcacctgc ccagtgggcc ccgctgcagc tgtgtgtcct      240
tctccatcta cacggcctgg ggcgagcact gtgagcacct gagcatgaaa ctcgacgcgt      300
tcttcggcat cttctttggg gccctgggcg gcctcttgct gctggggggtc gggacgttcg      360 tggtcctgcg cttctggggt tgctccgggg ccaggttctc ctatttcctg aactcagctg      420
aggccttgcc ttgaaggggc agctgtggcc taggctacct caagactcac ctcatcctta      480
ccgcacattt aaggcgccat tgcttttggg agact                                 515
```

<210> SEQ ID NO 17
<211> LENGTH: 270
<212> TYPE: DNA
<213> ORGANISM: Homo sapiens
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: modified_base
<222> LOCATION: (197)..(198)
<223> OTHER INFORMATION: a, c, t, g, unknown or other
<220> FEATURE:
<221> NAME/KEY: misc_feature
<222> LOCATION: (197)..(198)
<223> OTHER INFORMATION: n is a, c, g, or t
<220> FEATURE:
<221> NAME/KEY: modified_base
<222> LOCATION: (202)..(203)
<223> OTHER INFORMATION: a, c, t, g, unknown or other
<220> FEATURE:
<221> NAME/KEY: misc_feature
<222> LOCATION: (202)..(203)
<223> OTHER INFORMATION: n is a, c, g, or t
<220> FEATURE:
<221> NAME/KEY: modified_base
<222> LOCATION: (205)..(224)
<223> OTHER INFORMATION: a, c, t, g, unknown or other
<220> FEATURE:
<221> NAME/KEY: misc_feature
<222> LOCATION: (205)..(224)
<223> OTHER INFORMATION: n is a, c, g, or t

<400> SEQUENCE: 17

```
gttacttaat aggtactcag cctggagtga aaatcctggg tactgacttt gagaggagtg       60
agtgtgcatg ttgtcaaagt ttctgaacnc agttcacata gccttattag caaaagtttt      120
aagaaatggc tctatcaaag aagcaattgc agctttattc agaaatataa aagtggaatt      180
```

```
tatgtacatg tcataanngg tnncnnnnnn nnnnnnnnnn nnnngggtgg ataactctta      240
ggatttaact ctttgaatat tatctcttga                                      270
```

<210> SEQ ID NO 18
<211> LENGTH: 245
<212> TYPE: DNA
<213> ORGANISM: Homo sapiens
<220> FEATURE:
<221> NAME/KEY: misc_feature
<222> LOCATION: (34)..(59)
<223> OTHER INFORMATION: n is a, c, g, or t
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: modified_base
<222> LOCATION: (179)..(180)
<223> OTHER INFORMATION: a, c, t, g, unknown or other
<220> FEATURE:
<221> NAME/KEY: misc_feature
<222> LOCATION: (179)..(180)
<223> OTHER INFORMATION: n is a, c, g, or t

<400> SEQUENCE: 18

```
tcctttgtgg ccttaaccct tctgcatcag ggannnnnnn nnnnnnnnnn nnnnnnnnna      60
cctcatggga ccagacccct tgggaccaca tggcacaatg ggacctctgt tgtacattcc     120 ggttgggggga tgagcgttgc tatttaatta ctaatattat tgaatgcctt agaggangnn    180
gggcgagccc ggtgttctga agacctgtgg cccagcagag cctctgacag taaagttttg    240
ctcca                                                                 245
```

<210> SEQ ID NO 19
<211> LENGTH: 501
<212> TYPE: DNA
<213> ORGANISM: Homo sapiens
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: misc_feature
<222> LOCATION: (438)..(438)
<223> OTHER INFORMATION: n is a, c, g, or t

<400> SEQUENCE: 19

```
tggccagata ctatgctaag cccttttttaa ttttattatt attatatttt gtcaccgagg    60
ctggagtgca atggcccgat cttggctctg caacctccgc ctcccggttt aaagcgattc    120
tcctgcctca gcctcccgag taactgggat tacaggcggg cgccaccacg cctcgctgat    180
ttttgtattt tagtagagac ggggtttcgc catttttggcc aggctggtct cgaccctgac    240
ctcagggtga tccgctcacc tcagccactc aaaagtgctg ggattactgg cgtcagccac    300
cgcgcgcccg gtcgtgctaa tcactttgaa aggcattatc tcatcggtta aaacatagtt    360
ttccggactt aaaagtttac agcacactgg cgcagaagat ggaaaaccgc tgcttgcctt    420
tctccgttta ttgactcnca ttctgctctt tggatcattt tcttcggaaa aagttttcca    480
aagtgtgtct tgtgtattaa a                                               501
```

<210> SEQ ID NO 20
<211> LENGTH: 434

<212> TYPE: DNA
<213> ORGANISM: Homo sapiens

<400> SEQUENCE: 20

```
gactagccag cagtggtgct ctgagagtga acgagcacct ccaggtggag ggccacagca      60
acgtctacgc cattggtgac tgtgccgacg tgaggacgcc caagatggcc tatcttgccg     120
gcctccacgc caacatcgcc gtggccaaca tcgtcaactc tgtgaagcag cggcctctcc     180
aggcctacaa gccgggtgca ctgacgttcc tcctgtccat gggagaaat gacggtgtgg      240
gccaaatcag tggcttctat gtgggccggc tcatggttcg gctgaccaag agccgggacc     300
tgttcgtctc tacgagctgg aaaaccatga ggcagtctcc accttgatgg agaggccagg     360
cgggagaact accgcagcag gtgggcgtac ggactgcttg gcgcatggca cccgcctggc     420
aagtgctaga acta                                                       434
```

<210> SEQ ID NO 21
<211> LENGTH: 508
<212> TYPE: DNA
<213> ORGANISM: Homo sapiens

<400> SEQUENCE: 21

```
gtagtgctcc taacatgtat tatcaacttt gtggattaca ttggaggaaa atttaaaact      60
ggggccttga atatttattt tttgaaacta ccatgttaaa tactgaagta taatttgggg     120
gagttataaa gttatgataa acattcatct gattatttta acaatagtt gtggtagata      180
aacatactgg aggtgagtca aattgaattc atatagtaac atgcagtctg aagtcctagt     240
tacttaatag gtactcagcc tggagtgaaa atcctgggta ctgactttga gaggagtgag     300
tgtgcatgtt gtcaaagttt ctgaacacag ttcacatagc cttattagca aaagttttaa     360
gaaatggctc tatcaaagaa gcaattgcag ctttattcag aaatataaaa gtggaattta     420
tgtacatgtc ataagtggta cccacttccc cttttactg tagggtggat aactcttagg      480
atttaactct ttgaatatta tctcttga                                        508
```

<210> SEQ ID NO 22
<211> LENGTH: 544
<212> TYPE: DNA
<213> ORGANISM: Homo sapiens

<400> SEQUENCE: 22

```
aaaggcgtgt ttgactgcag gaagaacgtg ctgggtcaca tgcagcaggg tggggcaccc      60
tctccatttg atagaaactt tggaaccaaa atctctgcca gagctatgga gtggatcact     120
gcaaaactca aggaggcccg ggcagagga aaaaaattta ccaccgatga ttccatttgt      180
gtgctgggaa taagcaaaag aaacgttatt tttcaacctg tggcagagct gaagaagcaa     240
acggattttg agcacaggat tcccaaagaa cagtggtggc tcaagctacg gcccctcatg     300
aaaatcctgg ccaagtacaa ggccagctat gacgtgtcgg actcaggcca gctgaacat      360
gtgcagccct ggagtgtctg acccagtccc gcctgcatgt gcctgcagcc accgtggact     420
gtctgttttt gtaacactta agttatttta tcagcacttt atgcacgtat tattgacatt     480
aatacctaat cggcgagtgc ccatctgccc caccagctcc agtgcgtgct gtctgtggag     540
tgtg                                                                  544
```

<210> SEQ ID NO 23
<211> LENGTH: 461
<212> TYPE: DNA

```
<213> ORGANISM: Homo sapiens
<220> FEATURE:
<221> NAME/KEY: modified_base
<222> LOCATION: (306)..(309)
<223> OTHER INFORMATION: a, c, t, g, unknown or other
<220> FEATURE:
<221> NAME/KEY: misc_feature
<222> LOCATION: (306)..(309)
<223> OTHER INFORMATION: n is a, c, g, or t
<220> FEATURE:
<221> NAME/KEY: modified_base
<222> LOCATION: (311)..(314)
<223> OTHER INFORMATION: a, c, t, g, unknown or other
<220> FEATURE:
<221> NAME/KEY: misc_feature
<222> LOCATION: (311)..(314)
<223> OTHER INFORMATION: n is a, c, g, or t

<400> SEQUENCE: 23
atagtttccc tacccagaga tattagaagt atgctacagt gaatgttaaa gtaccttgag      60
atccttaaat caaaggtgct atatacataa gtaagactct actttcagaa aaaggtaata     120
ttatttcctg cactgatccc tactaattct atattgatcc aaaggcaact caatgctaaa     180
aaatgtatag aaaatataag tctgtgtctg tgtactgtag agatgtatgt gacaagtgta     240
aacaaaatga actgaagcag taatgaacag ttattagggg gaacatgata aagagattat     300
attaannnna nnnntcacca taaaatcctt tttatggctt actaaaaccg agctcactgt     360
aaaatcatga tccaacttat tgctaatctt tatgatatgc ttattcctaa tctttatggt     420
atggtgtcaa ccgttcattt gtatcttatt gctcattccc t                         461

<210> SEQ ID NO 24
<211> LENGTH: 339
<212> TYPE: DNA
<213> ORGANISM: Homo sapiens

<400> SEQUENCE: 24
ttcccaaaac ctctcaatga accctatgct gctactgact ggacgtacct ggaagggagc      60
tattcttggt ggctttaaaa gtaaagaatg tgtcccaaaa cttgtggctg attttatggc     120
taagaagttt tcattggatg cattaataac ccatgtttta ccttttgaaa aaataaatga     180
aggatttgac ctgcttcact ctgggaaaag tatccgtacc attctgatgt tttgagacaa     240
tacagatgtt ttcccttgtg gcagtcttca gcctcctcta ccctacatga tctggagcaa     300
cagctgggaa atatcattaa ttctgctcat cacagattt                            339

<210> SEQ ID NO 25
<211> LENGTH: 529
<212> TYPE: DNA
<213> ORGANISM: Homo sapiens

<400> SEQUENCE: 25
attgggcctg tcagcccgaa tgggaataga agtggtgatg aggcaagtat tctttggagc      60
aggaaactac catttagtgg atgaaaactt cgatccttta cctgattatt ggctatctct     120
tctgttcaag aaattggtgg gcaccaaggt gttaatggca agcgtgcaag gttcaaagag     180
aaggaagctt cgagtatacc ttcattgcac aaacactgac aatccaaggt ataaagaagg     240
agatttaact ctgtatgcca taaacctcca taatgtcacc aagtacttgc ggttacccta     300
tcctttttct aacaagcaag tggataaata ccttctaaga cctttgggac tcatggatt      360 actttccaaa tctgtccaac tcaatggtct aactctaaag atggtggatg atcaaacctt     420
gccaccttta atgaaaaaac ctctccggcc aggaagttca ctgggcttgc cagctttctc     480
```

```
atatagtttt tttgtgataa gaaatgccaa agttgctgct tgcatctga              529
```

<210> SEQ ID NO 26
<211> LENGTH: 441
<212> TYPE: DNA
<213> ORGANISM: Homo sapiens

<400> SEQUENCE: 26

```
gagtagcaga accaggagcc tcttccatac atgaggaaag attgctgcct tttcagcaga   60
agggaaattc ctaggattgg ctgtcccctg ccaagcttgg tggagcgtct gcaccttggc  120
tgcgccgcct gtgcatttgc cagtttcctc ccactgagag gatggaggtg tccgcacagc  180
tttgggcctc gtgagggatc tgcctcctga gcaaagagct cttgatcccg atttcatgca  240
cagccctgca gtaaggagcc agaaggaac atgtgtttcc tgttaaaact cctcttgttc   300
tcttttctta cattatgacg tttgttttca aggagagggt ttaaaaatgg gatcctgtaa  360
gcagacttgg gcagtctcct tttgaaatag gttgtctgta catgttctaa tgttttgtag  420
aacacgtgtg cctgtttaag t                                            441
```

<210> SEQ ID NO 27
<211> LENGTH: 399
<212> TYPE: DNA
<213> ORGANISM: Homo sapiens

<400> SEQUENCE: 27

```
ggtcggatgg acacacagcc agaccgtaaa ccctcacgta tccccacgcc tcggggcccc   60
cgccgcccct ccggacccgc agagctgggg acatggcatg ccctgcactc agtcaccccg  120
agggctgagc cagattcctg gatgtgatgg accagctcag ctgtccccag accccatccc  180
ttctcctttt cctttgtggc cttaaccctt ctgcatcagg gagcccctc tgcctcttga   240
gtaccagacc tcatgggacc agaccccttg ggaccacatg gcacaatggg acctctgttg  300
tacattccgg ttgggggatg agcgttgcta tttaattact aatattattg aatgccttag  360
aggaggccgg gcgagcccgg tgttctgaag acctgtggc                         399
```

<210> SEQ ID NO 28
<211> LENGTH: 538
<212> TYPE: DNA
<213> ORGANISM: Homo sapiens

<400> SEQUENCE: 28

```
tccacctact ccattgcttt atgaggttta aggaaggaag gcggtataat ccctattcaa   60
tatattttt ctaaaatcca acttctgacc gcccagtagg aagaaaaatg agacattttt   120
tccattacag agaaatgctt cttgacttta acatcagcat tataaaagt gtcaaataaa   180
aaattaccat cattatcatt aaaataaatt ttcactgtat ttgagatggg agggttaagg  240
ctcagggatt ttatttcagt gaactgctgg aactcacaca tgccctgata tgtaaatgat  300
gatttatgtt ggcgagtctg agagcaagcc caaatgtgtt cttcaaagga caatgggaaa  360
ctgtaaagta gagaactaaa gaataaggcc tttagaatct gacacatctg ggttcaaatt  420
ctgaaactgt cacttattac ctgtatgaac atgggcaaat tatctaatct ctctgatcta  480
tttttcctca tctgtaaaat aggtgtaata ataacaacta ctttgtcggt tgctctga    538
```

<210> SEQ ID NO 29
<211> LENGTH: 347
<212> TYPE: DNA

<213> ORGANISM: Homo sapiens

<400> SEQUENCE: 29

```
ttattcttgc atttccataa ggaaagggaa agtcatgatc atcctaaagg atcacagttt     60
ttaaaaggca acatttttcc ctaaggaaac agacacaagc tttcctagag aatatgatgt    120
tttttaggca ttaataaggt ccttttttat aaaggacact tttctcctag tagttttgaa    180
ttcaggaaca gatccaaagt tagcagtata tggctgctac atttccattt tcattttcga    240
gccatcagtt tatgttcaga tgccatctct gtaatcgcac atttaaaaca taactgtagc    300
ctcactaatg gaaagtagt atgatgaaca atcattccca atggtgt                   347
```

<210> SEQ ID NO 30
<211> LENGTH: 503
<212> TYPE: DNA
<213> ORGANISM: Homo sapiens
<220> FEATURE:
<221> NAME/KEY: modified_base
<222> LOCATION: (313)..(313)
<223> OTHER INFORMATION: a, c, t, g, unknown or other
<220> FEATURE:
<221> NAME/KEY: misc_feature
<222> LOCATION: (313)..(313)
<223> OTHER INFORMATION: n is a, c, g, or t

<400> SEQUENCE: 30

```
acttttgact tattcgtttt gcctggaagc actaaggctt acagtctgtg gtgactggca     60
gtaagaatca acatggtttt ccttttttctt tttctccagt gaaaactatt tccactttaa   120
gtcttctgca cacggcaatt aatgagagga ataatactc cctgaccaaa tcacaaacat    180
tctgtataat catataagtt acttttccaa gctgcacaaa tgatatgttt cacatgctga    240
gaattgttaa caagtacagt actcaatacg caatgttaga acttactttg tttaaagcaa    300
atagactgag atnaaatatc tatcccctaa ccccaagatg cttacaatct tcctagagtt    360
caaggcttgc ttataaaaac aacaacaaca tcaacaacaa agcaataaga ggcaatgaat    420
ggcaatacag ataataaaca ccagaaagaa gttcgctgta agttggtgta gttatggaaa    480
tgatgatctg tagttcgtct gag                                            503
```

<210> SEQ ID NO 31
<211> LENGTH: 357
<212> TYPE: DNA
<213> ORGANISM: Homo sapiens

<400> SEQUENCE: 31

```
atatttcagt atgttcttca gagggatagt tctgattttt catgccttgg gaagaatctc     60
ttgcttcaat gctaaaaata cttggtagat cagcatgctg gctctcctcc tgtgaagaat    120
attctggctg aagctgttca aaacattgtt cagatcctgc attaagaaat tcaaaaatca    180
gttaatcatc gttacatgtt gtaaaagttg gatactgaca gtctctaata gtttatcatc    240
caattgcaag taacctacaa ttttaggcat aaaagttgat gtgtataaac atgaatacaa    300
agataaggat ggtcacagtg atttctcaaa ctacagctca caccaagtat tttttct       357
```

<210> SEQ ID NO 32
<211> LENGTH: 125
<212> TYPE: DNA
<213> ORGANISM: Homo sapiens

<400> SEQUENCE: 32

```
ttgatacct caccttact acactgtatc ctccatttga atgttgtcaa gagctcttct       60
```
cacaattgta aataataatt gtgtaattt gttttttttt tcctacttta ggttgctcct    120
tgagg                                                              125

<210> SEQ ID NO 33
<211> LENGTH: 373
<212> TYPE: DNA
<213> ORGANISM: Homo sapiens

<400> SEQUENCE: 33
cattgtgaaa acactgccct gcctaggcat accccctttc cagaattaac tttccattta   60
attctatagt ttttcactga tgtaactttc tagactggac aacaaagatg actaatagta  120
atcactccaa gttgatgttg actgttgggt tgtggtgaaa tcattttgca ttaaaggaag  180
gtaaaatact aataaattgc atattccttg accagagcac agattactta tgcttcttaa  240 tttttaaaa tcttaaatcc tctgtccaac tggagtatct ggctatgggc catgggtact   300
catataccct ttgtcttaaa ctgatctgtt acattttatg ttcttgtggc tagaagtagc  360
ctgagtttgc tgt                                                     373

<210> SEQ ID NO 34
<211> LENGTH: 476
<212> TYPE: DNA
<213> ORGANISM: Homo sapiens
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: modified_base
<222> LOCATION: (178)..(182)
<223> OTHER INFORMATION: a, c, t, g, unknown or other
<220> FEATURE:
<221> NAME/KEY: misc_feature
<222> LOCATION: (178)..(182)
<223> OTHER INFORMATION: n is a, c, g, or t
<220> FEATURE:
<221> NAME/KEY: modified_base
<222> LOCATION: (184)..(184)
<223> OTHER INFORMATION: a, c, t, g, unknown or other
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: modified_base
<222> LOCATION: (433)..(433)
<223> OTHER INFORMATION: a, c, t, g, unknown or other
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: modified_base
<222> LOCATION: (443)..(443)
<223> OTHER INFORMATION: a, c, t, g, unknown or other
<220> FEATURE:
<221> NAME/KEY: misc_feature
<222> LOCATION: (443)..(443)

<223> OTHER INFORMATION: n is a, c, g, or t

<400> SEQUENCE: 34
agctatgatt catcttaatg cttgtatcca cttcctttaa tgagcaattt aaatattagg    60
gcatacacca cctgtntttt ttgaaagttg tatgtgtttt attttcccag gattactctc   120
ttaacatctt aaagcagtaa aagtatacag tattaatgaa accaaaattg ccctttnnn    180 nnangctaat tttccaaata tttatttagt tcataaaatt cacattttat tttttaaaca   240
ttataggtta gaagaattac aattgtaatt ccctggcacc atgatagcat tattgtggta   300
gtactgctag gtgagggaat ggtatgttaa gtctgttttt gaaagtaaa atgaatacga    360 gttcacaatc acgaaataca gattgttaaa agtcttgtaa cagaaaaatc caaagttagt   420
atagttttta aanaagccna aantacatgg agcaagttgc tgtcataaaa gctgcc       476

<210> SEQ ID NO 35
<211> LENGTH: 505
<212> TYPE: DNA
<213> ORGANISM: Homo sapiens
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: modified_base
<222> LOCATION: (168)..(168)
<223> OTHER INFORMATION: a, c, t, g, unknown or other
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: modified_base
<222> LOCATION: (182)..(182)
<223> OTHER INFORMATION: a, c, t, g, unknown or other
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: modified_base
<222> LOCATION: (187)..(188)
<223> OTHER INFORMATION: a, c, t, g, unknown or other
<220> FEATURE:
<221> NAME/KEY: misc_feature
<222> LOCATION: (187)..(188)
<223> OTHER INFORMATION: n is a, c, g, or t
<220> FEATURE:
<221> NAME/KEY: modified_base
<222> LOCATION: (194)..(194)
<223> OTHER INFORMATION: a, c, t, g, unknown or other
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: modified_base
<222> LOCATION: (460)..(460)
<223> OTHER INFORMATION: a, c, t, g, unknown or other
<220> FEATURE:
<221> NAME/KEY: misc_feature
<222> LOCATION: (460)..(460)
<223> OTHER INFORMATION: n is a, c, g, or t

<400> SEQUENCE: 35
gttttcttag attattacag cagtgaacta tttccacctg gtaagaaggg tgcacttgag    60
aatggggtnc aagtactcta ggaacataga tgtaagttct ggatgcacag tagttgttgc   120

```
ttagctgtaa gctggaaatt tcaaggcaga aacagcagat accacaanta taactgggtc    180
tncttgnntt ttgntttatg tgtatacgtg agattatggg gaaagacaaa agtaatgcat    240
agagatttat tttttaacat tcaattcata agcagtgttt atacctcttt gtacttactt    300
gaaaagtgta tattatgtaa atttagtata aaaacacttg gactaattca taccatgtgg    360
taaaatttca cattcaaaag aaatacccct ctgttattaa aaataaaaaa aaaaggagcc    420
aggagggtgg ctcatgactg taatcccagt gctctgggan gccaaggtgg agggatcatt    480
tgaggccagg actacttgag aacag                                         505
```

<210> SEQ ID NO 36
<211> LENGTH: 564
<212> TYPE: DNA
<213> ORGANISM: Homo sapiens

<400> SEQUENCE: 36

```
tacttagctt actgttttga ggttcattca cgttgttaca tggcttagta gtattttttt     60 cttttatta ctgagtggta tttcattcta taatttgctt attcattgat tgttgatgg    120 gcatctggat tatttccagt tcgaggtcat tacaaataaa atctctatgg acatttgtgt    180
actagtcttt atgcttttat ttcttatgct tttattctct ttgataatta actatctgtg    240
gaatggctga gtcatatggt agatatatgt ttaagtggta agaaactgcc cagctgggcc    300
aggcgcagtg gctcatgcct gtaatcccag cactttggga ggtcgaggcg agcggatcac    360
gaggtcaaga gattgagacc acggtgaaac cccgtttcta ctaaaaatac aaaaaattag    420
ccgggcgtgg tggtgggtgc ctgtagtccc agctactcgg gaggctgagg caggagaatg    480
gcgtgaacct gggaggcgga gcttgcagtg agccgagatc gtgccactgc actccagcct    540
gggtgacaaa tggggactcc gtct                                          564
```

<210> SEQ ID NO 37
<211> LENGTH: 397
<212> TYPE: DNA
<213> ORGANISM: Homo sapiens
<220> FEATURE:
<221> NAME/KEY: modified_base
<222> LOCATION: (70)..(71)
<223> OTHER INFORMATION: a, c, t, g, unknown or other
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: modified_base
<222> LOCATION: (73)..(76)
<223> OTHER INFORMATION: a, c, t, g, unknown or other
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: modified_base
<222> LOCATION: (206)..(206)
<223> OTHER INFORMATION: a, c, t, g, unknown or other
<220> FEATURE:
<221> NAME/KEY: misc_feature
<222> LOCATION: (206)..(206)
<223> OTHER INFORMATION: n is a, c, g, or t

<400> SEQUENCE: 37

```
gattagccta gcatttgtcc tctttatata aaggacttct tatagcctga ttcctaatgc     60
agagttcagn nannnngaca tttatttggt aacagctttt gagaaatgtt actttatttc    120
```

| | | |
|---|---|---|
| taaataatta tatacttggc agtttattct tccagttaag tttactaata gttactgatt | 180 | |
| tgttaatata agtttgtaag ttgttnttga aagttaaaat gaagctgggt gtggtggctc | 240 | |
| acacctgtaa tcccagcgct ttgggaggcc aaggcgggca gatcaaggag tcaggagatg | 300 | |
| gagaccagcc tggccaacat agggaaaccc tatctctact aaaaacacaa aaattagctg | 360 | |
| ggtgtgatgg cgtgcacctg taagctgagc tactcag | 397 | |

<210> SEQ ID NO 38
<211> LENGTH: 409
<212> TYPE: DNA
<213> ORGANISM: Homo sapiens

<400> SEQUENCE: 38

| | | |
|---|---|---|
| gtggtatggc aacaggtacg taaacatact gataatgttt acattaatgc attaagtttt | 60 | |
| ggcctaaccct ggccccaacc atttcagtgg tctcttttga atagatatct tatgtttaca | 120 | |
| actcaataat ctttatagag cactggcccct gtgctttatt agatgcatag ctttcctatt | 180 | |
| tatctgctca tattggccat tttgcaggat gaattaagag ttttgtatgt aaatactgca | 240 | |
| tcacattaga ccttaaagtt ctttgggtta aatttcaacc agaaaaggaa ataagacca | 300 | |
| tttatggaaa ctgtatgatt ccacctagaa gctactgatt ttttagagta gttgcttaga | 360 | |
| aagaactcag aaacctcttc tactaaaaga ctattgtgtt tcaggattc | 409 | |

<210> SEQ ID NO 39
<211> LENGTH: 478
<212> TYPE: DNA
<213> ORGANISM: Homo sapiens

<400> SEQUENCE: 39

| | | |
|---|---|---|
| ttgataccct caccctttact acactgtatc ctccatttga atgttgtcaa gagctcttct | 60 | |
| cacaattgta aataataatt gtgtaatttt gttttttttt tcctacttta ggttgctcct | 120 | |
| tgagggcagg acagttctta tggctttatc cgttgcgtaa gcacagagag gtctgcgagg | 180 | |
| tcaaaactat tgtcatgata gcaagatgcc tgtcttttc atttattctc acggtgtgca | 240 | |
| gaggctacat gatgtgtgat gacatcctca ttgatgttaa tgaatggtgc tatacttgaa | 300 | |
| ttttctaagg tgtcattagg taggtttagg tatgcatact tgttttaga aattatttt | 360 | |
| ttccttttc ccatttttag aaatcaactc attttttagg ttatgccttc agtaatcttt | 420 | |
| gcaacctcaa tattgtgtaa tggttacttt aaaatactgt agttttcttt gtgcctaa | 478 | |

<210> SEQ ID NO 40
<211> LENGTH: 404
<212> TYPE: DNA
<213> ORGANISM: Homo sapiens

<400> SEQUENCE: 40

| | | |
|---|---|---|
| gcagagtgag caacttttct ccagaaacca cactacagat agccataagc aaacagtagc | 60 | |
| aacagactct catgaaggac ttacagaaaa tagagagcca gattctgttg atgagaaaat | 120 | |
| tactttccct tctgacattg atcctcaagt tttctatgaa ctaccagaag cagtacaaaa | 180 | |
| ggaactgctg gcagagtgga agagaacagg atcagatttc cacattggac ataaataagc | 240 | |
| atattcagca aaaaggtctg aaaagcaagg gaataccatt attttcggat tagcggttta | 300 | |
| ttaagctctt ctatattaaa cactaataga tattcaataa cggagtaaac tgttccagat | 360 | |
| aaagcaagaa tagttgcaag aagtaaattc tggcacaaag cgta | 404 | |

<210> SEQ ID NO 41
<211> LENGTH: 474
<212> TYPE: DNA
<213> ORGANISM: Homo sapiens
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: misc_feature
<222> LOCATION: (40)..(40)
<223> OTHER INFORMATION: n is a, c, g, or t

<400> SEQUENCE: 41
aaagctctat gaactagttg gtattatana ccttaggccn tttcaagtaa aaattacata    60
tcaatgttta ttaaatactg agttaatagc tgaatacctc tttcatatac aaataagtac   120
atttgcaatt ttttaaaaag tcttaattcc attagtaact gtggtttcat agttgccaaa   180
taactgtaag ctatggatgt tgcacaagac tgtgatttta tttaatcatt tcatatctat   240
ttaaacattt ccaaagcgca cattcatctt aatgttttca cactattttt gctcaacaaa   300
aagttatttt atgttaatgg atataagaag tattaataat atttcagtca aggcaagaga   360
acccgataaa gatcattgct agagacgttt aatgttacct gtagcggtac acttgttaaa   420
gaagtgatta agcagttaca taaaattctg atcatagctt tgattgatac catg         474

<210> SEQ ID NO 42
<211> LENGTH: 537
<212> TYPE: DNA
<213> ORGANISM: Homo sapiens
<220> FEATURE:
<221> NAME/KEY: modified_base
<222> LOCATION: (208)..(208)
<223> OTHER INFORMATION: a, c, t, g, unknown or other
<220> FEATURE:
<221> NAME/KEY: misc_feature
<222> LOCATION: (208)..(208)
<223> OTHER INFORMATION: n is a, c, g, or t

<400> SEQUENCE: 42
cagttttgca gagcatgtca ccaaaattta ttggatgaag aaattaaaat ggttaaatag    60
aagaagttct caacctcact aatgatcaga taagtgcaga ttgtaaaagt cctcatcccc   120
accaacacaa accagcagaa atttatgtg aatgtgaagt ttggataata ccagtattg    180 tcgcaggtgt gagaaaccgt attttcanat attgagaggg taaattagag aaagccatt    240 ttagagggca atgtggtgtt acctgtcagc attttgaata taattaccct ttgccacaat   300
tctacaccta gtcagttatg ttctcaaaaa gcacaagtgc agaaatatag atgcataagc   360
aaatgtgttg cagaattgtg aaaaatttgg aaaaaatgtt tagtgctatt aaagttatgg   420
gttacttaag ttacagaaaa tcagtttagt agatcactgt gtagttacgg aaaatgagat   480
ggatctctac tcaaagatgt cttgcagttt atgaactgag atgtaacttc atgacta      537

<210> SEQ ID NO 43
<211> LENGTH: 421
<212> TYPE: DNA
<213> ORGANISM: Homo sapiens
<220> FEATURE:

```
<221> NAME/KEY: modified_base
<222> LOCATION: (134)..(134)
<223> OTHER INFORMATION: a, c, t, g, unknown or other
<220> FEATURE:
<221> NAME/KEY: misc_feature
<222> LOCATION: (134)..(134)
<223> OTHER INFORMATION: n is a, c, g, or t

<400> SEQUENCE: 43
tacatttcac atttaccagc aagtcagtaa aaaatagtgc ttatttacat agtcaatata      60
atttaatgtt ctaaaaataa tatcttcgat ctgcccaata tttaatgtat catttgagat     120
ttttaaaaat gcanccgctc cattatgtaa acattaagat atgcctatgt ttctttaact     180
atacagcctc tttacaataa atttcttgat ttttgtgcac aggatagtat tgcaacctgc     240
tatttagcct ttggtgcctt agaattatta taaatattta acaatatgta cataatgtaa     300
atactgccaa gagatcagta aggccaaata ttttctctat tcactttta ttgctcttgc      360 tttctattgc tactaaagcc tcttttatcc agctttgtaa tagttccaac attgtagcga     420
a                                                                    421

<210> SEQ ID NO 44
<211> LENGTH: 325
<212> TYPE: DNA
<213> ORGANISM: Homo sapiens

<400> SEQUENCE: 44
gaagatcttc atcggtgtgc acttttaaca ggtttgaacc tattcatata gttttgtttt      60
agcataaaac tttgaatgga taaaaagaa gatgaggaaa ctaaaaagtc agattgaata     120
atatagggaa tgattattct agtagattgt gaaagagaac tgtatctact gcagagttc      180 aaacttttca ggtttgtttt aggtaagcct attttatatt agaaataat aaatgaaagt      240 ggtgattatc ttatatttaa cataaggatt taccttgtca tttgtttaaa tgtattgact     300
gtatgactca agttataacg gacag                                          325

<210> SEQ ID NO 45
<211> LENGTH: 513
<212> TYPE: DNA
<213> ORGANISM: Homo sapiens

<400> SEQUENCE: 45
aactgtcaga aacttctgtg catgtattta tatttgccag agtataaact tttatactct      60
gatttttatc cttcaatgat tgattatact aagaataaat ggtcacatat cctaaaagct     120
tcttcatgaa attattagca gaaaccatgt ttgtaaccaa agcacatttg ccaatgctaa     180
ctggctgttg taataataaa cagataaggc tgcatttgct tcatgccatg tgacctcaca     240
gtaaacatct ctgcctttgc ctgtgtgtgt tctggggag gggggacatg gaaaaatatt      300
gtttggacat tacttgggtg agtgcccatg aaaacatcag tgaacttgta actattgttt     360
tgttttggat ttaaggagat gttttagatc agtaacagct aataggaata tgcgagtaaa     420
ttcagaattg aaacaatttc tccttgttct acctatcacc acatttctc aaattgaact      480 ctttgttata tgtccatttc tattcatgta act                                 513

<210> SEQ ID NO 46
<211> LENGTH: 375
<212> TYPE: DNA
<213> ORGANISM: Homo sapiens
<220> FEATURE:
<221> NAME/KEY: modified_base
```

```
<222> LOCATION: (46)..(46)
<223> OTHER INFORMATION: a, c, t, g, unknown or other
<220> FEATURE:
<221> NAME/KEY: misc_feature
<222> LOCATION: (46)..(46)
<223> OTHER INFORMATION: n is a, c, g, or t

<400> SEQUENCE: 46
gagactggag acatgattgt gccactgtac tccagcctgg gtgacngagt gagaccctgt      60
ctcaaaaaca aacaaataaa taaaaccaca acaaggtaca tttaggcaaa aatataaagt     120
ctcacaatgc caattattgg tcaagatatg gaataacaga aactcatata ctccttggaa     180
ggctaaattg atagaatcat cttgtggaaa gtttgttatt acctatcagc gtatggatcc     240
aatactctaa gaagacctca taattttaca cctaggtaaa tattaatatt ttacaaactt     300
cacatatgtc cataaagaaa cacaagtaaa aatacttata gcaaaaaact ggaaataact     360
aggtccactg atagg                                                     375

<210> SEQ ID NO 47
<211> LENGTH: 298
<212> TYPE: DNA
<213> ORGANISM: Homo sapiens

<400> SEQUENCE: 47
ggaatctggg atgactctta gtaatctact attcttaatt caacgatggc caccagctac      60
ctgacacatt ttgtaaattt agcatctgtg tatgtgtgtt cgtgtatgtg tgtgtgcgtg     120
catgtgcaca ttactgcatt tattctcaaa tggatttata atttagtgtt tttgtacaag     180
tacttgagct attcatgtaa tgggataagt tgccataaag atgtacataa atgaccctta     240
atttggcacg ttttcacatt taattttta aaatacagct tttcatatac agttccta       298

<210> SEQ ID NO 48
<211> LENGTH: 511
<212> TYPE: DNA
<213> ORGANISM: Homo sapiens

<400> SEQUENCE: 48
ttgacttcaa aatcatggct tatatgtact ttctctattt cccagatgca aatataatta      60
attgacttta tttatctagg aaatgttact catatcttaa ttgtagtcat tggcttgagt     120
gacgggtttt ggtaattcaa ctactattac ttgaaagtag tagatttcat aggatactgt     180
tataaaatct tttaacctc tttctgatt tcaggagtaa ttagtaattg tggtttactg     240
gaaaattcaa tgaatagggt gttaaaggaa gcaattcatt aataatatat gtaatctatt     300
gggagactga ggcgggtgga tcacctgagt tcaggagttc gagaccagcc tggccaacat     360
ggcaaaactc cgtctctact gaaaatagaa aaattcgccg gcatggtgg tgcattcctg      420 tattcccagg tactcggaag gctgaggcag gagaatcacc tgaactccag aggtggaggt     480
tgcagcgagt caggatcgca gcactacact c                                   511

<210> SEQ ID NO 49
<211> LENGTH: 326
<212> TYPE: DNA
<213> ORGANISM: Homo sapiens
<220> FEATURE:
<221> NAME/KEY: modified_base
<222> LOCATION: (104)..(104)
<223> OTHER INFORMATION: a, c, t, g, unknown or other
<220> FEATURE:
<221> NAME/KEY: misc_feature
<222> LOCATION: (104)..(104)
```

<223> OTHER INFORMATION: n is a, c, g, or t

<400> SEQUENCE: 49

| | | |
|---|---|---|
| tcacccatac gtccaacatc gaaagaaaac cagtgttatg actttgttcc atttgaagac | 60 |
| taattgggag tccatctctc tattggcact gggttcgatt gccnctggct aatagagttc | 120 |
| aattagttct atccctgggt ttcctttctt agctatgggg tggaagatag gaggggaga | 180 |
| tctacaattt gaatatgtgt tacttaataa ggctaggctg gccatcagtt gcttatttca | 240 |
| gatgtgtcac taaatttttcc ttctagatgg tccttgagca aaacttaata attactgttt | 300 |
| tttatttcca ctgcctttat aaaatc | 326 |

<210> SEQ ID NO 50
<211> LENGTH: 381
<212> TYPE: DNA
<213> ORGANISM: Homo sapiens
<220> FEATURE:
<221> NAME/KEY: modified_base
<222> LOCATION: (83)..(87)
<223> OTHER INFORMATION: a, c, t, g, unknown or other
<220> FEATURE:
<221> NAME/KEY: misc_feature
<222> LOCATION: (83)..(87)
<223> OTHER INFORMATION: n is a, c, g, or t
<220> FEATURE:
<221> NAME/KEY: modified_base
<222> LOCATION: (98)..(98)
<223> OTHER INFORMATION: a, c, t, g, unknown or other
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: modified_base
<222> LOCATION: (323)..(323)
<223> OTHER INFORMATION: a, c, t, g, unknown or other
<220> FEATURE:
<221> NAME/KEY: misc_feature
<222> LOCATION: (323)..(323)
<223> OTHER INFORMATION: n is a, c, g, or t

<400> SEQUENCE: 50

| | | |
|---|---|---|
| aagacaccat atatgctcat gccttaaact tggacttccc agcctccaga accatgagaa | 60 |
| ataaatctgt gtgactgatt gannnnnacc cagtcttnta aatactccat actagtctct | 120 |
| ggtattttgt tataccatcc tgaatggact aagacacata gggtctatgt tacaactact | 180 |
| cagctctgct attatagcac aaaagaagcc agataatata ttaatattaa acaaatgggc | 240 |
| atggctatat ccaataaagc ttcatttaca aaaatagcca gcctatggac cacatttgac | 300 |
| taagttcaaa cagaaataat ccnctttaac aagaaataaa acaataccat ttaaaggaag | 360 |
| ataacataag ccagatgcct t | 381 |

<210> SEQ ID NO 51
<211> LENGTH: 479
<212> TYPE: DNA
<213> ORGANISM: Homo sapiens

<400> SEQUENCE: 51

| | | |
|---|---|---|
| gagtgatttc tgtttaatcg caatttgttg gtaataccaa tgtgtgaaat tagtgaaatc | 60 |
| ttagtacctt aacttcaaac atttctcttc agaaaagttc cctttctaa aattgagata | 120 |
| acatagttct tgaatatttt gctgtattta tagcctcata tttaggcatt tatgcactga | 180 |
| tgtgtcttca ataaaaatct tgtacagata tatttttata attatttata atttatattt | 240 |
| tgatattcta tttaagttat cctgattctt taaaagtagt tattgggagt agaagaacac | 300 |

```
aatataaata tttccgtgta atagccacca acttttcagg cataggtttt attacaactg      360
ttaaggaggt tttgcttctt ctttagataa caacttgttt gcccaaaaga atcctaattt      420
gtacacttaa catgtatttg tattaaactt tttaaataat tgctttctta tcaaaccaa       479
```

<210> SEQ ID NO 52
<211> LENGTH: 369
<212> TYPE: DNA
<213> ORGANISM: Homo sapiens

<400> SEQUENCE: 52

```
atctagatgc atccatagca cctagtgaag gctcaccata tggtcagaat actcgatgca       60
cactgataca actctctaca tccatctctg tgttagggac aaatgttact ttactcttgc      120
acagaacttg gacagtcact tttaatatct gtcttttctt tttctatttt cattactgat      180
accctctgcc ccttctttct gactaaaact ctcattcaat aaaattatag tcaaatcttg      240
caattggaaa agtattcaga cttttaaagt tatatttata tatctaaatg ttgctccatt      300
agggttttaa ttctaaattt aacctttaaa aagttatcat attttcttta tttccaggtt      360
cctaggaga                                                             369
```

<210> SEQ ID NO 53
<211> LENGTH: 502
<212> TYPE: DNA
<213> ORGANISM: Homo sapiens

<400> SEQUENCE: 53

```
aagcagcatg attgcacttc ttgtagtgca taccatcact aaaacatagt tactgtcttt       60
ctgtggtctt aagaaaaatt cagaaacagc ataccaatgt acatataaga taaataagct      120
tatgtggtac agtaagtgtt ctgttctgag aaataccttg attcgtatcc taatgtctga      180
tgttattggt agttctcaaa cttccccaat tctgctttca tctaaattca tcttatctat      240
ctattgttaa ataatctatc agtccatttt tatctatcat ctatatatct gtctttatca      300
atcattcgtc tgtaatctat ctgtgccgtt tggcataaga gacagaaggg catagcagtg      360
gaaactcaaa ggagttacct ccatgtgaat ggacagtggg gatggtgatc tgtgaggtgg      420
tgatgtatag aaagaaaaac tagaagagag catgccctaa ctcagggacc ttgtccagca      480
ggcactctgg ccttgttata ct                                              502
```

<210> SEQ ID NO 54
<211> LENGTH: 424
<212> TYPE: DNA
<213> ORGANISM: Homo sapiens
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: misc_feature
<222> LOCATION: (180)..(180)
<223> OTHER INFORMATION: n is a, c, g, or t

<400> SEQUENCE: 54

```
attgccaact tttgggagat ttcacatatt ttacctctat attttatttt tccaggattg       60
gtatggagga gtagtacctt ctattcttgg tttatttttta tttgctagac ataatttctt      120
aactacatat gtaagtataa attcataaaa atcacactga aagaataggt tgatttcaan      180 ccatttgag ggtactggta ggtaacacac tgttgggaa taaactaaag aatttctgat        240
```

```
ttctacaata gatttaagta tgaaatttga gtatactgtg tagctgtgta gatcaactta      300
atgcttaaaa aattacctcc ttaatgatta gattaataga acagtgttag attatcaagg      360
gaagagtttg gaatgtaaac ataaacatgc tgcataggtg gtggttattt gtgagtagga      420
ctac                                                                  424
```

```
<210> SEQ ID NO 55
<211> LENGTH: 468
<212> TYPE: DNA
<213> ORGANISM: Homo sapiens

<400> SEQUENCE: 55
ggcatagtaa cttgtaaata cgtctataaa tatttggaca atgacttaac tttagaattg       60
cttcaactag agtgtatgta tatatagata gatagataca tagtctctcc atatatctat      120
atacacacac aatggaatat tattctgcca caaaaagaag gaaatcttgt ttgtgccaac      180
gtggatgaac ctggaggaca ttaggctaag tgaataaggc aggcacagaa aggcacataa      240
ccacatgatc tcacttatat gtggaatcta aaaaagttga tctcgtagaa ctagattgta      300
gattaggggg tggggtaggt gtggtggggt ggaggttgtt ggtcagagga tacagtttca      360
gctggataga ataagttcta aagatcaatt gtgaaacgtg atgactataa taatacagtt      420
gacccttgaa caacataggt tttaactggg tggcgacatt atacatga                  468
```

```
<210> SEQ ID NO 56
<211> LENGTH: 452
<212> TYPE: DNA
<213> ORGANISM: Homo sapiens
<220> FEATURE:
<221> NAME/KEY: modified_base
<222> LOCATION: (390)..(390)
<223> OTHER INFORMATION: a, c, t, g, unknown or other
<220> FEATURE:
<221> NAME/KEY: misc_feature
<222> LOCATION: (390)..(390)
<223> OTHER INFORMATION: n is a, c, g, or t

<400> SEQUENCE: 56
attaattcca tatctggcaa caggtggact agatgtctgg cgaataacac ctaatataaa       60
acacctgtca cggtgattga aaaaaatcaa cagctatctc attaaatgca tggcaagtaa      120
aatatatctt ctggggccaa aaatagacca gaattatctg ctacttgaat gtttggcaaa      180
actctcctag aaaactgagt ctgatgtttg atttgtgtaa agacttcttt aacttttcta      240
actcaatttt tactaagtta taggactact cagattttgt ttctttttg ctcaattttg       300 gtcaattttg tttttgtcta tgtcacctaa gttttcaaat gtattggcat gaatattttc      360
ataatattcc cttattatct tttacatttn tgggatatct ttagcgatgt ttccctttt      420 atccctaaaa ttgtttattc atgctttctt tt                                   452
```

```
<210> SEQ ID NO 57
<211> LENGTH: 535
<212> TYPE: DNA
<213> ORGANISM: Homo sapiens
<220> FEATURE:
<221> NAME/KEY: modified_base
<222> LOCATION: (110)..(110)
<223> OTHER INFORMATION: a, c, t, g, unknown or other
<220> FEATURE:
<221> NAME/KEY: misc_feature
<222> LOCATION: (110)..(110)
<223> OTHER INFORMATION: n is a, c, g, or t

<400> SEQUENCE: 57
```

```
aacaggataa gtggtagccc attatataag aagaccgata agaatttctt aaatatgcca       60
aaaataatct gaacaatcag ccatttctgt gaactgtggc tttagtaccn tccaattgtc      120
tttcacaaat tctgttggtg aatgtgtaaa ctggcataaa catgtacaga aatcaattag      180
caatttatct gaattctctc cctcaggaag tactctgtga actaaacata atgcagagta      240
agtactttca cttgaaatga cagggcatct gagttttgct tcaaaataat gttggggcca      300
ggtgcagtag ctcacacctg taatcctagc actttgggag gccaagggag aaggatcacc      360
tgagctcagg agttcaagac cagcctaggc aacatagtga gatctcgtct ctaaataaaa      420
tatacaaaag agtattggga gggggtatga agaatgtata gggcaataat tgaaatctgt      480
tgaagctggg tacacaaaag ttcattatgt tgtttctcta catttatatc tattt          535

<210> SEQ ID NO 58
<211> LENGTH: 537
<212> TYPE: DNA
<213> ORGANISM: Homo sapiens

<400> SEQUENCE: 58
ggttacccca tttgttaatg agcattaatg ttttctgaac acttccaaag attaatcaaa       60
cataaatatt cattgtctga aaatgtcttt aagatacaat tcagaggtcc ctatttcctt      120
tgtacataca cacttagaaa gaaaagacag aaaaggaaga ggaaggaagg aaatattttg      180
agaatatatt gagaagaatt aagaaaactc ttcaatgaag tgttaacaac caaaccctac      240
agacggtatc agaaacagca aatagatatt cctctaccct ttcacagtga gtgagtgagt      300
acagaagaat gctcatgata gttttgcctt cattctactt tctgtggaca cagagtaatg      360
aatatttaat gggacattaa atatgcccct caaatctata attttacttt ggtaaacgag      420
atttaacatg atgtctttta tgctcctaaa acatcttttt tcaaactcca ttccttagaa      480
cattcttcta ctgagatgat ccaagaccaa aagtgttctt tggtacttgc ttataaa        537

<210> SEQ ID NO 59
<211> LENGTH: 455
<212> TYPE: DNA
<213> ORGANISM: Homo sapiens

<400> SEQUENCE: 59
aagcctttag gcagaatgta caccttgtta gtcatttgag aattcatact ggtgaaaaac       60
cctatgaatg taaagaatgt ggaaaagctt ttagaatcag ttcacagctg gctactcatc      120
agagaattca tactggagag aagccttatg aatgtattga atgtgaaat gctttcaaac       180 agagatcaca ccttgcccaa catcagaaaa ctcatacagg agagaaacct tatgagtgta      240
atgaatgcgg gaaagccttc agccaaactt ccaatcttac tcaacatcaa agaattcata      300
ctggagagaa accctataaa tgtactgaat gtggaaaggc ttttagtgat agctcatcct      360
gtgctcagca tcaaagactc cacactggcc aaaggcccta tcagtgtttt gaatgtggga      420
aggcgttcag aagaaagtta tccttaattt gtcat                                 455

<210> SEQ ID NO 60
<211> LENGTH: 369
<212> TYPE: DNA
<213> ORGANISM: Homo sapiens
<220> FEATURE:
<221> NAME/KEY: modified_base
<222> LOCATION: (79)..(79)
<223> OTHER INFORMATION: a, c, t, g, unknown or other
<220> FEATURE:
```

<221> NAME/KEY: misc_feature
<222> LOCATION: (79)..(79)
<223> OTHER INFORMATION: n is a, c, g, or t

<400> SEQUENCE: 60
gggcaaagag taaactaccc tgcaaatata tgcggataat ttaattggtt tcatattaca    60
ggaatctaga gggccaatna ctttttcagt aataaaaaaa taaaagggcc agatgcagtg   120
gctcatgcct gtaatcccag cactttggga gtccaaggca gagagatcgc ttgagctcag   180
cagtttgaaa ccaacttggg caaaatgaga aaacacccat ctctaaagaa atatataaat   240
tagacagaaa tggtgtcatg tgcatgtagt acttgtattc ccagctacct caggaggctg   300
aggtgtgaag atcatttgag cctggagagg tcaaggctga ttgagccatg atggtgccag   360
tgtacttca                                                          369

<210> SEQ ID NO 61
<211> LENGTH: 494
<212> TYPE: DNA
<213> ORGANISM: Homo sapiens
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: modified_base
<222> LOCATION: (73)..(73)
<223> OTHER INFORMATION: a, c, t, g, unknown or other
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: modified_base
<222> LOCATION: (116)..(117)
<223> OTHER INFORMATION: a, c, t, g, unknown or other
<220> FEATURE:
<221> NAME/KEY: misc_feature

```
<222> LOCATION: (116)..(117)
<223> OTHER INFORMATION: n is a, c, g, or t
<220> FEATURE:
<221> NAME/KEY: modified_base
<222> LOCATION: (128)..(128)
<223> OTHER INFORMATION: a, c, t, g, unknown or other
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: modified_base
<222> LOCATION: (205)..(205)
<223> OTHER INFORMATION: a, c, t, g, unknown or other
<220> FEATURE:
<221> NAME/KEY: misc_feature
<222> LOCATION: (205)..(205)
<223> OTHER INFORMATION: n is a, c, g, or t

<400> SEQUENCE: 61
ttggtcttta tctagaagtt tgatgatttt tttgtgacca gaaatatgcc gtagganctt    60
anctctngtt ttnancaatt agcctgtggt aaaaantggt ttcgttatcc atcttnnggc   120
ttaaagtngc aatttccaag aacttattga taacgttgag tgagtactta actgtatgtt   180
gcaatattgc attgttcttc tgttngacat cctacatttg tgtcatacat cctaatatct   240
ggtaggtaaa atagtgaaag aaactgtagg caattaatgg tagtgccaat gtatgaattc   300
tttcttcctg ttctttgtca gataaacaaa gatatttagt atacacaatt ttacgaaagt   360
agggcttagg aaaagcagag taatgatgcc tgtggtatag tagtgtggct tgtaattaca   420
ctgtgtttag cctgactctc catttcactc ttttgggttt aataatatac tctccatttg   480
gagaccaagg cagg                                                     494

<210> SEQ ID NO 62
<211> LENGTH: 497
<212> TYPE: DNA
<213> ORGANISM: Homo sapiens

<400> SEQUENCE: 62
ctgctgccat tttaatcttg ctcattaacc ttactccttt gagaattctt taacaatatt    60
taaaattggt aacaaaaata gtttagccat aattgtttag ccatgtgagt ttcaggttgg   120
tacacgttca gacagaactg ctgtatcaca ttccaatttt gaatagccag tgagcaatca   180
agtgtagaga aatgataaat ggcctaagaa ggcatacagt ggcataaacg atgctcttcc   240
tagtagctta ataggccaca agctagtttc tgttgcactc tgaaataaaa tatgctttaa   300
aaatgtaggg aacagtgctt agaaaagcaa aaactaggtg tgtcattgaa ataataggca   360
taaaaattaa atgttacata agaacactat ttggaaagag ggtccttta aaaactgaat   420 ttgtactaaa tcagatttgc catgtccagt acagaataat ttgtacttag tatttgcagc   480
agggtttgtc tttgtga                                                  497

<210> SEQ ID NO 63
<211> LENGTH: 521
<212> TYPE: DNA
<213> ORGANISM: Homo sapiens
<220> FEATURE:
<221> NAME/KEY: modified_base
<222> LOCATION: (151)..(151)
<223> OTHER INFORMATION: a, c, t, g, unknown or other
<220> FEATURE:
<221> NAME/KEY: misc_feature
<222> LOCATION: (151)..(151)
<223> OTHER INFORMATION: n is a, c, g, or t
```

<400> SEQUENCE: 63

```
tttcttcaac cttttttcaa gcagtgtcag ctaaatggtg ccatttgctt atcactcttc     60
tttttggtta tttatcctaa agataagaac attagtaagc cgtaaatgcc cattttgtaa    120
aaactgcata gctagacaga tttgcaatcc ntattagggt aataatccat ctgttatgga    180
actggatcaa ttttgtaaat taaatagatt aaaaaggggg aaaaagggcc atgacttttc    240
ccacagtaag ccttttctca aatgctaaaa agatttggga agactcaaac tatttgccat    300
tcttcctctc tttgcttaac tcagagagaa ggccaaatat ctattaaaaa gaggggtggg    360
tgcagttgtt ttttttttta attcttcagg gtctgattgc tcctggaagt ttcatatttt    420
tgacagagtt tattgttaaa accttttgat gactaccaga acatttctgc tgttctcact    480
gatcagttta gtaaatgtgt gactatgttt gaattttctt c                        521
```

<210> SEQ ID NO 64
<211> LENGTH: 511
<212> TYPE: DNA
<213> ORGANISM: Homo sapiens
<220> FEATURE:
<221> NAME/KEY: modified_base
<222> LOCATION: (473)..(473)
<223> OTHER INFORMATION: a, c, t, g, unknown or other
<220> FEATURE:
<221> NAME/KEY: misc_feature
<222> LOCATION: (473)..(473)
<223> OTHER INFORMATION: n is a, c, g, or t

<400> SEQUENCE: 64

```
actcaggtgg attcataatt tgttctgttt ccttgctctt aggaaaagta ctgacagctc     60
ataattggtt gtatttctta ggatatttgc atttaaacta gaagcaatgc tttctttttct   120
tggtataatt tgtcttacat ttttgaaagt aatagctatt cattaaatta catttgaaaa    180
tgcaggaaga aagaaaaaat tgtctataat tctactactc atataaaacc actattcaca    240
tatgtgtact ttcctctatt aacctttcaa agcatgcctc aattttaatt gtattcacac    300
aaatacaatt ttatgccata catttttactt attaatatgc tattagcatc accaatgtca   360
atataaactc cttgtaaaca tcaatttaat ggttgcaaag tattacatca actggatatg    420
ccatggctta tttaatcact gtatttattg ttaaatattt gcattgttta cantgtttag    480
tattgaaaac cacgctgcaa taaatatctt t                                   511
```

<210> SEQ ID NO 65
<211> LENGTH: 481
<212> TYPE: DNA
<213> ORGANISM: Homo sapiens
<220> FEATURE:
<221> NAME/KEY: modified_base
<222> LOCATION: (325)..(325)
<223> OTHER INFORMATION: a, c, t, g, unknown or other
<220> FEATURE:
<221> NAME/KEY: misc_feature
<222> LOCATION: (325)..(325)
<223> OTHER INFORMATION: n is a, c, g, or t

<400> SEQUENCE: 65

```
taatattcat tgtcacatgg tgtgaagacc tatcaatcaa ttttttgttaa acaagtaaat    60
caggaaaaat atttttttgtc attattacat taagaaaatt tattatccag gtgacagtac   120
atactggagt ttttggaaga agtgaggagc catgacctaa aaaagcttgt gtttcctgcc    180
agcagcacat cttaaccaaa gatgttccag ctaagttaac ccagaatatt agacaggaaa    240
gaaatctgaa aacagatgat gcacttgcaa attgtgcaag gcttgttctg taatgcaaat    300
```

```
aggatgtctt ctttgaaatg taaangcact gagcctaagc atgaggaatt ttaatgtcta    360
atgatgaagc tatagagaga aatttcagtt aatgaccagg taggtataag atggtgtcct    420
tagataattc tgatatcaga actgatgtta attgtagttt aagacaactc tcctgagaca    480
g                                                                   481
```

<210> SEQ ID NO 66
<211> LENGTH: 520
<212> TYPE: DNA
<213> ORGANISM: Homo sapiens
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: n is a, c, g, or t

<400> SEQUENCE: 66

```
cactactcta ctatctgtgt gatattagac aaaatntttg cttcttggta cctcagctgt     60
aaaatgaaac acacctaaaa gtgtggttgt ttccaacatg tataatacag caacaactat    120
ctggcccaaa ctgctttgga ttaatattgg atattactgt ttttattatc atcaacatta    180
ttattagtgg atttcttaat aggaagatgc aatggagatg acaaatttgg aaaaaccact    240
catcacttac atttcatgaa gtacttcttt gataaaatct gttatgggct gaatgtttgt    300
gttcccgtaa caattcctat gttgaaacac gaatcccaag gtgatggtat ttgaaggtag    360
ggcctttagg aggaaattag gtcatgaggg tggagccttc atgagtggaa ttactgcctt    420
tataagaaga agccaaagag ccagctagct cttcaaccca catgaggtta cagcaagaag    480
tcagcagtct acagtgcaaa agagggcctt caccagaacc                          520
```

<210> SEQ ID NO 67
<211> LENGTH: 447
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: misc_feature
<222> LOCATION: (48)..(48)
<223> OTHER INFORMATION: n is a, c, g, or t

<400> SEQUENCE: 67

```
ggagaaatac atcatgacca agtagggtgt attcccagaa atttatcnga aaatctatca     60
ttgcagtgta cacgtgaaat gattgtagaa gaacagcatt atattcattt tggattcaga    120
gaggtatttg agaaatttga ccactcaata acttagtaaa gggctattta tcaaaccttt    180
ggcaaacata gttaagggtg aatatttagc agccttacca ttaatggtgg aacattctg     240 gggcagaccc atgctcagta attcagaaat gaggcataag aactggaaag aaagcaacga    300
gactgattca attgtctgta taaagaaacc agagaatgta caacagattg ttagacctaa    360
taagagttca acaatttgaa agttgttcaa acaaaatcaa catactaaga taattgtttt    420
tctatgcccc agtgataacc agttgaa                                        447
```

<210> SEQ ID NO 68
<211> LENGTH: 131
<212> TYPE: DNA

<213> ORGANISM: Homo sapiens

<400> SEQUENCE: 68

```
ccttctaact taatgctttc ggacggggat ccccggcaaa taacgtaaga ggattttat      60
ttgtgcatgt gttcctgcaa ttgatctctt tgatgacatt ctcattcata gaaagcgttt     120
gatttatgag c                                                          131
```

<210> SEQ ID NO 69
<211> LENGTH: 395
<212> TYPE: DNA
<213> ORGANISM: Homo sapiens

<400> SEQUENCE: 69

```
aagtcttgtt gtctagtctc attcacctgc ctcaacatgc tttctttcat tctatttgca      60
tacaaaatgt tcttatttca gttttgtaga caggatatga gttagcatac tcgtgtttgt     120
tcagctgtcc atcctgcatc gttactacaa tgccttttc tgccatttaa tggtgttgt      180
atcaatgttc ccatatctgc tgcattttaa ctccataaaa aggaaatgtg atttcgtatt    240
aatagttttg ttgatcaact caatatttct gcaccaatca gcatacctat atgcatgtag    300
tagtctgtac aattgttcaa catcaaaata cttgtttact ttatgtcaaa atgtctataa    360
aattgctggc attgttctcc atttcagtct ggtag                               395
```

<210> SEQ ID NO 70
<211> LENGTH: 413
<212> TYPE: DNA
<213> ORGANISM: Homo sapiens
<220> FEATURE:
<221> NAME/KEY: modified_base
<222> LOCATION: (166)..(166)
<223> OTHER INFORMATION: a, c, t, g, unknown or other
<220> FEATURE:
<221> NAME/KEY: misc_feature
<222> LOCATION: (166)..(166)
<223> OTHER INFORMATION: n is a, c, g, or t

<400> SEQUENCE: 70

```
taaggtagca tttcatccac acgatggagt gtgttttatt cagtaattga tttaaaaatg      60
gaatcaacct aagtgtctaa caggagggag ttttataaat tgttcacaga gcatctgttc    120
caaggagacc ttgatgttca tagatttgta aagaatgctg cttacntagc acactgactc    180
ctctgcaaat gtctgagggt tcctccactt ggggcaagtt ggggggtttga tcgcagagta    240
aataaatggt gcatttata atgtaatata ttctagcaag atgcagccca caaactgtat     300
agatactctt atgtaccacg taaagttcat ctactacttt aaccagaact tgatactgta    360
tgtatgtttt ttttagatt tggataaaat gacaactcat tgttatttcc agt            413
```

<210> SEQ ID NO 71
<211> LENGTH: 363
<212> TYPE: DNA
<213> ORGANISM: Homo sapiens
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: misc_feature
<222> LOCATION: (256)..(256)
<223> OTHER INFORMATION: n is a, c, g, or t

<400> SEQUENCE: 71

```
gaacatggac gaaggaattc ctcatttgca agagagacag ttactggaac atagagattt      60
```

```
tataggactg gactattcct ctttgtatat gtgtaaaccc aaaaggagca tgaaacgaga    120
cgacaccaag gatacctaca aattaccgca cagattaata gaaaagaaaa gaagagaccg    180
aattaatgaa tgcattgctc agctgaaaga tttactgcct gaacatctga aattgacaac    240
tctgggacat ctgganaaag ctgtagtctt ggaattaact ttgaaacact taaaagcttt    300
aaccgcctta accgagcaac agcatcagaa gataattgct ttacagaatg gggagcgatc    360
tct                                                                  363
```

<210> SEQ ID NO 72
<211> LENGTH: 410
<212> TYPE: DNA
<213> ORGANISM: Homo sapiens

<400> SEQUENCE: 72

```
gcatgtgtaa aaagtccttc agccacaaaa ccaacctgcg gtctcatgag agaatccaca     60
caggagaaaa gccttataca tgtccctttt gtaagacaag ctaccgccag tcatccacat    120
accaccgcca tatgaggact catgagaaaa ttaccctgcc aagtgttccc tccacaccag    180
aagcttccta agctgctggt ctgataatgt gtataaatat gtatgcaagt atgtatattc    240
ctatagtatt tatctactta ggatataaga tataatctcc tgattatgct ttcaatttat    300
tgtcttgctt cattaaaatg taaggctaag gagagcatgg aatttgtcag ttttgttcac    360
taaagtattc caagtggttg ggaaagtgga acatttccaa gaaccaataa               410
```

<210> SEQ ID NO 73
<211> LENGTH: 545
<212> TYPE: DNA
<213> ORGANISM: Homo sapiens
<220> FEATURE:
<221> NAME/KEY: modified_base
<222> LOCATION: (205)..(205)
<223> OTHER INFORMATION: a, c, t, g, unknown or other
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: modified_base
<222> LOCATION: (236)..(236)
<223> OTHER INFORMATION: a, c, t, g, unknown or other
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: modified_base
<222> LOCATION: (296)..(296)
<223> OTHER INFORMATION: a, c, t, g, unknown or other
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: misc_feature
<222> LOCATION: (419)..(419)
<223> OTHER INFORMATION: n is a, c, g, or t

<400> SEQUENCE: 73

```
gacatatcac tgcttgatgt atagttaaaa agagatgcca tcatcacaat tattcaaata     60
gtttacagtg tatgtttaac caagtataga tatattttta aatatgatta tttctaccta    120
```

-continued

```
gtattttcag aattgagttt agaatgattt acttgggatg tgcggcgatt cttttttaga    180
taagtggggg atgttaggaa gacantgttc aagtgcttga aactttaatt tggacnaata    240
cattgaacca catgctggaa tgttttaagt gactacctta tagttttagt atgagnccta    300
cccttggaag aaagtaaggt gatactaaat tagaaaaact atgtgaaact ggagtggtgg    360
tatactttgg accatatcaa ataggtagag tattataagc ataaagaat aaaattggnc     420
tcgctttgga aattttaaac atatatgtgt atgtgtgtat atatatgcat atacatacac    480
atatgtgtat atacacacac acaatggttt ggaagtggaa caggaaatga taactctact    540
gacat                                                                545
```

<210> SEQ ID NO 74
<211> LENGTH: 466
<212> TYPE: DNA
<213> ORGANISM: Homo sapiens

<400> SEQUENCE: 74

```
gtggttgatt ttgacatagc tgcaattaca gttttcttct attttttcaag ccacaataag    60
gaaaataaac tactcatggt ctaaatacta gagataaagt agattcatgg cttggtaagg   120
aaattttaag cattccttca aagattgacg tgctaaaata agcattgatg ttttgagttt   180
ttttacacct aggattttta gcttgggtgt gtaggtgaag gccaagactc tctgcaggaa   240
aaagcttatt ttcaaactca gaaaataaaa tgtcaatcat aaaaatctac ttcaacttta   300
gcaaaaagaa aaaaaaatca acaaaaagta tactctgtat gctgggattc cgaggttcca   360
acacactgtt acaaatctgt gggggggtttc tttcttctga taattctaga gcctgttacc   420
atagaaaggc atttcttcaa tggctggttg tagttagttc atgttt                  466
```

<210> SEQ ID NO 75
<211> LENGTH: 494
<212> TYPE: DNA
<213> ORGANISM: Homo sapiens
<220> FEATURE:
<221> NAME/KEY: modified_base
<222> LOCATION: (45)..(45)
<223> OTHER INFORMATION: a, c, t, g, unknown or other45
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: modified_base
<222> LOCATION: (47)..(47)
<223> OTHER INFORMATION: a, c, t, g, unknown or other45
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: modified_base
<222> LOCATION: (60)..(60)
<223> OTHER INFORMATION: a, c, t, g, unknown or other45
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: modified_base
<222> LOCATION: (75)..(75)
<223> OTHER INFORMATION: a, c, t, g, unknown or other45
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: modified_base
<222> LOCATION: (339)..(339)
<223> OTHER INFORMATION: a, c, t, g, unknown or other45
<220> FEATURE:
<221> NAME/KEY: misc_feature
<222> LOCATION: (339)..(339)
<223> OTHER INFORMATION: n is a, c, g, or t

<400> SEQUENCE: 75

```
aagcaccagg gcacggacag gaataaggcc taaactcaca gagcntnttc atggtctgcn      60
tttttctgtg tgtgncagag ttatttcaca tccagaagac gcatatttac aggggaaaag    120
tactgaatta gccactttct ccatagccaa gttgcgaatg gatcccaaag ggccccggca    180
agttggacaa catgtgagct ttgggcgaca gttgctacaa acaagatggc cactctgaca    240
ttgaagaatg ggcggtaaca catagtcaaa gcagactgga cactcaaaaa gactcgccaa    300
gtcattgttg gatgcagttg tgccagtcag ggcaggcanc ctctgggatg gtggacactt    360
cgaggtaccg gtaggtaatg ctgtagcagt ctgacggctc atttctgaaa taaatacata    420
aggaggcagg agaaaaataa ttataaccat gacttacttt ataaataatg tttacatgcc    480
ataagtcctt ttaa                                                      494
```

<210> SEQ ID NO 76
<211> LENGTH: 307
<212> TYPE: DNA
<213> ORGANISM: Homo sapiens

<400> SEQUENCE: 76

```
ggttgtccaa ctctgaatgt actggaaacc attgaagtat acattttaaa tgggtgtgct     60
aaatggtata tgaattattt ctcaataagt gtgttttttt aaaaaagcta ttgattattt    120
ccatcagtct cattcctctt gacaaaaatc tgagttgatg gtgagcatgt acttcattcc    180
tgactccaaa gggtacaata tttacaatat ttgaatttgg gagtgacttt actattacaa    240
ccttccccctt gaagacctgg aagacccagc aacataagga caaacagtag tctcagcctt    300
gtactaa                                                              307
```

<210> SEQ ID NO 77
<211> LENGTH: 452
<212> TYPE: DNA
<213> ORGANISM: Homo sapiens
<220> FEATURE:
<221> NAME/KEY: modified_base
<222> LOCATION: (377)..(377)
<223> OTHER INFORMATION: a, c, t, g, unknown or other
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: modified_base
<222> LOCATION: (382)..(383)
<223> OTHER INFORMATION: a, c, t, g, unknown or other
<220> FEATURE:
<221> NAME/KEY: misc_feature
<222> LOCATION: (382)..(383)
<223> OTHER INFORMATION: n is a, c, g, or t
<220> FEATURE:
<221> NAME/KEY: modified_base
<222> LOCATION: (395)..(395)
<223> OTHER INFORMATION: a, c, t, g, unknown or other
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: modified_base
<222> LOCATION: (409)..(413)

<223> OTHER INFORMATION: a, c, t, g, unknown or other
<220> FEATURE:
<221> NAME/KEY: misc_feature
<222> LOCATION: (409)..(413)
<223> OTHER INFORMATION: n is a, c, g, or t
<220> FEATURE:
<221> NAME/KEY: modified_base
<222> LOCATION: (415)..(417)
<223> OTHER INFORMATION: a, c, t, g, unknown or other
<220> FEATURE:
<221> NAME/KEY: misc_feature
<222> LOCATION: (415)..(417)
<223> OTHER INFORMATION: n is a, c, g, or t

<400> SEQUENCE: 77

| | | | | | |
|---|---|---|---|---|---|
| gtctgattga | ggaagctatg | gctgactata | accaagcact | tgatcttgaa | gactatgcct | 60 |
| cagttatatg | attacataga | ctgtggttgc | tatagtagtt | tacacagctg | ttctctctga | 120 |
| aacggaaaca | tatttgttgt | ctaaaaggtt | ctaccatttt | cattattgta | ttcgttatgc | 180 |
| ttagtcttcc | atataacctt | ctatgcattt | taataaaatg | tttgttatac | attaattata | 240 |
| aaacatatat | catttgctgc | atatttggaa | taccttgaga | actgaatttt | tccaaggttg | 300 |
| cagaatctca | aggaaaatgt | ttcttaagga | attaaatagg | aatgtctctt | aacatttaaa | 360 |
| atattttctt | taattcnttt | tnnaataata | ctatncattg | tagaaaaann | nnnannnacc | 420 |
| ttttcatcag | tccttgctga | caatgtatta | aa | | | 452 |

<210> SEQ ID NO 78
<211> LENGTH: 472
<212> TYPE: DNA
<213> ORGANISM: Homo sapiens
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: modified_base
<222> LOCATION: (155)..(155)
<223> OTHER INFORMATION: a, c, t, g, unknown or other
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: modified_base
<222> LOCATION: (181)..(182)
<223> OTHER INFORMATION: a, c, t, g, unknown or other
<220> FEATURE:
<221> NAME/KEY: misc_feature
<222> LOCATION: (181)..(182)
<223> OTHER INFORMATION: n is a, c, g, or t

<400> SEQUENCE: 78

| | | | | | |
|---|---|---|---|---|---|
| cattcttcca | aaataggttg | tcctgttgta | gaaagtgaaa | atagttttc | cccagtaaca | 60 |
| tgacnactca | aatgttntta | cattttaatt | tgttgggttc | ttattaaaag | aagcagggga | 120 |
| aagaatattt | ttctaaccac | catcgatttt | tcatnttcag | tgtatacatc | ttcatttttg | 180 |
| nnactttgc | aattttttcc | cctcccccct | taagtttaca | ttttaaaaag | cttatctgtg | 240 |

```
gttttcttgg taagacctac atatacccaa ggtggaaagt aaacatttgt tttaaggaag      300
tcctgtcata gtgtgctcaa gatagttcct ctgcccttac cttccctgtg aagcagaagg      360
aagaaatttt ctgattagca agatttggag tgtgaacata aagatacct atctgaaagc      420 ttctctagca gtttacaatt ctatgatatc attagttatt ccctagatta tc              472

<210> SEQ ID NO 79
<211> LENGTH: 553
<212> TYPE: DNA
<213> ORGANISM: Homo sapiens

<400> SEQUENCE: 79
agtatctact tcactgtcag ttcaagagaa tgtgaaacag tatgtgttag catttgagca       60
cttatttaat gagccatatc caaagttaga aatcatgcct tatggcacct agtcagttgt      120
gcagatggtt agtttgcttc taatattagt atatgagcat ttgtaatttc tagatgttgt      180
gcactcaaac ttggtataat ttaattctga acagtaaaca gtgtaaccaa ggtcttttaa      240
atactcaagt ttaaggtata atcttaatta tggctcagtc tttaaaaaag tataaatgtc      300
cttttacttt atcacaaaaa taaactcata tgaatactgt tccacatttg tttcttttgg      360
gaatagtttg cagaaaaata atttattcct aaattcaccc atcattttaa gaagtgccca      420
aatgtattta acaaaataat atatatgctg tattacttta aaacatcttt ttgtccaaaa      480
taagaacaat tgtcattatt ttgtctatgc ccaaataact attcaaataa tagcattcat      540
atgtactttc att                                                        553

<210> SEQ ID NO 80
<211> LENGTH: 372
<212> TYPE: DNA
<213> ORGANISM: Homo sapiens

<400> SEQUENCE: 80
ggaggctgag aatctaacag gtgtgaccaa ttctgctact gaatgagagc agaagcctgt       60
gaacttccag ttaatagacc acttaattgg gggaacgctt cacacgttat aaaaaagcac      120
tagaatgttt tgaaagcgag aaacaacagc tgtgtagggt agctagcagt tagtgttgta      180
cagaagacag atatttgtgc atttctgcat tttctaagtt tgctgcaatg agcatgtatt      240
actttcatag ttataaaaca catgcaaaat gcccttttaa aatgaaaaaa aagtccatga      300
gtgtaagtga tatatatgct ttggaaagcc tgggacggtc attgtttact ctcaatagta      360
tgtgtttgcc tt                                                         372

<210> SEQ ID NO 81
<211> LENGTH: 493
<212> TYPE: DNA
<213> ORGANISM: Homo sapiens

<400> SEQUENCE: 81
tcaactcttc gttttccag gttatttatt tcataagatg actatccata aatcttccga       60
tgaacgaacc tctttatgac cagagctcct ggggttaaag gagaaaggtt ttataatggc      120
tgtcttaatt tgtttggtgg ttttccaggt attaatgcca aatttgcctt tgtttagttt      180
ctgtttctta tcacactgtt ttcaggttac atcattatct taaaaaggca gaggctttat      240
tttcttcgtt gtgatataac ctaattctta gaggtttctt accagatcca ctttgcttgt      300
tttgcttaat tttatttct aaattttaca aattaatatt ttccaccaaa aggtggaacg      360
```

-continued

```
aaacaaagac agcaaaatat caaactgttt agtaatagtt aaaaaagtca agtgggaagg      420
aaggttgagg ctgaggcagg agaatcgctt gaacccagga ggtggaggtt tcagtgagct      480
gaggctgcgt cac                                                        493
```

<210> SEQ ID NO 82
<211> LENGTH: 490
<212> TYPE: DNA
<213> ORGANISM: Homo sapiens

<400> SEQUENCE: 82

```
gtgacacacg actgctcata caagcggagc agacttctga cggtccaaat ccttgtgaca       60
tggttaagca acctagatac cgaaaagggc ctgatgtctg ctttgataac aatgtcttgg      120
aggattatac tgactgtggt ggtgtttctg gattaaatcc ctccctgtgg tatatcattg      180
gaatccagtt tctactactt tggctggtat ctggcagcac acaccggctg ttatgacctt      240
ctaaaaacca aatctgcata gttaaactcc agaccctgcc aaaacatgag ccctgccctc      300
aattacagta acgtagggtc agctataaaa tcagacaaac attagctggg cctgttccat      360
ggcataacac taaggcgcag actcctaagg cacccactgg ctgcatgtca gggtgtcaga      420
tccttaaacg tgtgtgaatg ctgcatcatc tatgtgtaac atcaaagcaa aatcctatac      480
gtgtcctcta                                                            490
```

<210> SEQ ID NO 83
<211> LENGTH: 594
<212> TYPE: DNA
<213> ORGANISM: Homo sapiens
<220> FEATURE:
<221> NAME/KEY: modified_base
<222> LOCATION: (166)..(166)
<223> OTHER INFORMATION: a, c, t, g, unknown or other
<220> FEATURE:
<221> NAME/KEY: misc_feature
<222> LOCATION: (166)..(166)
<223> OTHER INFORMATION: n is a, c, g, or t

<400> SEQUENCE: 83

```
taaccatgac aatcaacgag gacatggcgc tggaggagcc tctatactta ccttctggga       60
tgctaggctg tacaaaatgg cagttggatt tatgcttgct catccttatg gatttacacg      120
agtaatgtca agctaccgtt ggccaagata ttttgaaaat ggaaangatg ttaatgattg      180
ggttgggcca ccaaatgata atggagtaac taaagaagtt actattaatc cagacactac      240
ttgtggcaat gactgggtct gtgaacatcg atggcgccaa ataaggaaca tggttaattt      300
ccgcaatgta gtgatggcc agccttttac aaactggtat gataatggga gcaaccaagt      360
ggcttttggg agaggaaaca gaggattcat tgttttcaac aatgatgact ggacattttc      420
tttaactttg caaactggtc ttcctgctgg cacatactgt gatgtcattt ctggagataa      480
aattaatggc aactgcacag gcattaaaat ctacgtttct gatgatggca agctcattt       540 ttctattagt aactctgctg aagatccatt tattgcaatt catgctgaat ctaa            594
```

<210> SEQ ID NO 84
<211> LENGTH: 527
<212> TYPE: DNA
<213> ORGANISM: Homo sapiens
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: misc_feature

```
<222> LOCATION: (87)..(87)
<223> OTHER INFORMATION: n is a, c, g, or t
<220> FEATURE:
<221> NAME/KEY: modified_base
<222> LOCATION: (375)..(404)
<223> OTHER INFORMATION: a, c, t, g, unknown or other
<220> FEATURE:
<221> NAME/KEY: misc_feature
<222> LOCATION: (375)..(404)
<223> OTHER INFORMATION: n is a, c, g, or t

<400> SEQUENCE: 84
atatatatct cccatgcact gttcttcaga aagccttggg agaatgtacc ctaccaaaag     60
agggagtaat aaactaggaa aagttgnatt tgggaaatgg aatcaactta gaaagaagca    120
aagaggcctg taatgataaa ggggttttct aggatgacag ctccatagct ggaatggggg    180
acaaccagac cagaatggag ctttagtaga tatattctag agcaggaaat tcgagaatat    240
ataaagtagc taaaatagaa gaaatgtag acaattgagt gagagttcaa gggtgaaata     300
acaatgttaa atactaaaaa atcaaagtaa aggaaaaagg acaattatta acttcaggaa    360
agacaaagtt atgcnnnnnn nnnnnnnnnn nnnnnnnnnn nnnnttgaat attgattgaa    420
ccacaattat gctctaacta tattgggaag aagaaagaaa gctgaaaata tgaaagagcg    480
ctaaatattt actcctacag gaaagagtca gtgatctcca aaacaga                 527

<210> SEQ ID NO 85
<211> LENGTH: 436
<212> TYPE: DNA
<213> ORGANISM: Homo sapiens
<220> FEATURE:
<221> NAME/KEY: modified_base
<222> LOCATION: (103)..(103)
<223> OTHER INFORMATION: a, c, t, g, unknown or other
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: modified_base
<222> LOCATION: (115)..(115)
<223> OTHER INFORMATION: a, c, t, g, unknown or other
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: modified_base
<222> LOCATION: (137)..(137)
<223> OTHER INFORMATION: a, c, t, g, unknown or other
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: modified_base
<222> LOCATION: (173)..(173)
<223> OTHER INFORMATION: a, c, t, g, unknown or other
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: modified_base
<222> LOCATION: (189)..(189)
```

<223> OTHER INFORMATION: a, c, t, g, unknown or other
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: modified_base
<222> LOCATION: (224)..(224)
<223> OTHER INFORMATION: a, c, t, g, unknown or other
<220> FEATURE:
<221> NAME/KEY: misc_feature
<222> LOCATION: (224)..(224)
<223> OTHER INFORMATION: n is a, c, g, or t

<400> SEQUENCE: 85

| | | | | | |
|---|---|---|---|---|---|
| gatgtaatgc | atatcacctg | tcatgtaaag | ggacggtatg | gatggtggaa | aagttatgct | 60 |
| aaaatatgga | ttgcagatat | ttttgtatgt | aatataggca | atnataatga | aacanccgag | 120 |
| tttttttaaag | tgaaagncat | gcaaaatcgt | agncttttaa | atgtacagac | atncccactc | 180 |
| aaaaatatnc | taaactgata | gtgggaaaaa | catttgagac | ctantaacat | catgaaatgc | 240 |
| actgaatttg | gaattctggc | ctagaaaggc | tgtggcttat | gttgggattg | atgatggaat | 300 |
| ctgccagaac | attttcatct | tattcttctt | gacttttgga | tttttttctt | ttctttttt | 360 |
| ctggaaatat | ttcggaaata | aagtgacttc | attttcagc | ataaagtat | attctaacca | 420 |
| cagggtaaca | catcgt | | | | | 436 |

<210> SEQ ID NO 86
<211> LENGTH: 390
<212> TYPE: DNA
<213> ORGANISM: Homo sapiens
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: misc_feature
<222> LOCATION: (96)..(96)
<223> OTHER INFORMATION: n is a, c, g, or t

<400> SEQUENCE: 86

| | | | | | |
|---|---|---|---|---|---|
| attgtttccc | atagcagaat | gtcaatattc | acagtacatt | tctgtaaaga | gcaaaccaat | 60 |
| ataatgtttt | gagtgttgaa | aaaaattcca | gatttntgaa | gaattagaca | actcttcatc | 120 |
| taccttattt | ctagttcaca | cagtatctc | aaattccact | gaaactaatg | ggatactgtc | 180 |
| ttgtgtagat | gccagttgag | tttataatgt | gacctagtaa | agctgtcttt | tttgttgtgt | 240 |
| tgtatgagtg | tcggatcatg | cttttaggaa | tacttttatt | aaaatggtgt | gcattcatgc | 300 |
| aaaaggccaa | ctggcttttg | tgaacaatag | atcttttctc | cccttttattt | tgttctcttg | 360 |
| acacttttgt | gaaaattacc | tagcctgata | | | | 390 |

<210> SEQ ID NO 87
<211> LENGTH: 280
<212> TYPE: DNA
<213> ORGANISM: Homo sapiens
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (31)..(31)
<223> OTHER INFORMATION: a, c, t, g, unknown or other

```
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: misc_feature
<222> LOCATION: (47)..(47)
<223> OTHER INFORMATION: n is a, c, g, or t

<400> SEQUENCE: 87
tgaggagact ctgtaattta aagcagnagg nacgagagga ggnaagnaaa cttccatgtt      60
aacatggcct actctcactc ctttctaaac gagccacttt tggcgtcaga agttgactgg     120
agagagataa acaaactccc agtcaaagcc cctaaagcga cagtgcccag agttctttta    180
ttttttgctg caaccaacgt aaacctgtaa aagaccaaca gtgaagatta gtgtattagt    240
gaatgcatgg aggccaatgc tgccctaatg agacgtgata                          280

<210> SEQ ID NO 88
<211> LENGTH: 505
<212> TYPE: DNA
<213> ORGANISM: Homo sapiens

<400> SEQUENCE: 88
gtgggtgttt gtagggctca taggctaaca agcactttag ttgctggttt acattcaatg     60
aaggaggatt catacccatg gcattacaag gctaagcatg tgtatgacta aggaactatc    120
tgaaaaacat gcagcaaggt aagaaaatgt accactcaac aagccagtga tgccaccttt    180
tgtgcgcggg gaggagagtg actaccattg ttttttgtgt gacaaagcta tcatggacta    240
ttttaatctt ggttttattg cttaaaatat attattttc cctatgtgtt gacaaggtat     300
ttctaatatc acactattaa atatatgcac taatctaaat aaaggtgtct gtattttctg    360
taatgcttat tttaggggg aaatttgttt tctttatgct tcagggtaga gggattccct    420
tgagtatagg tcagcaaact ctggcctgca gcctgtgtgt gcacgcccca tgagccgaaa   480
agtgggtctt atgttttcaa atggt                                          505

<210> SEQ ID NO 89
<211> LENGTH: 509
<212> TYPE: DNA
<213> ORGANISM: Homo sapiens

<400> SEQUENCE: 89
ttactatggt tgtacgtgcc tcaaataaac aagaatgata tttcctgttt tatttactta     60
tgttgggtaa atatgcttat tgaattttta agagaggatt ttttaccatc tccattttc    120 ttgtcattat gttttgtagc ttatttgagg gtgtctaaat ataatttcat attttattgg    180
ttcaactttc actctgaaga aatccgtatg ttagtacatt ttgaggtatt tttcttgttc    240
ttgtgttgtt taactatgac tcctaactga gtagtcttat atttcaatta caaatacat    300 tttttaagaa agggaataga gcagcaaaaa tgataaggaa aatgttaaaa gttgtaatat    360
```

```
ttcctttact cttaacagga ttatatatag aacatgctca cttacaaaaa taggatgatg      420
aagtttagag cataaggcag gcttcttgta tatacttatg ctgtcaaatg ttatattgtt      480
tttaatggag tcccattgtg taatattta                                        509
```

<210> SEQ ID NO 90
<211> LENGTH: 570
<212> TYPE: DNA
<213> ORGANISM: Homo sapiens
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: misc_feature
<222> LOCATION: (540)..(540)
<223> OTHER INFORMATION: n is a, c, g, or t

<400> SEQUENCE: 90

```
gaaaatgtgc tcaatcttac cagtcattat aaggaaataa tgaaatttgt gtatatatga       60
aatacttaaa atatatataa aataaaacaa ttatttgcct ttttttcacct atcagattaa     120 cagattatat gtgttaacaa ggtggggaga atttacaact cctgatatgt taaaatcttt     180
caggaaggta gtagaaaata tatgtaagat ggaaattagc acttttgacc aacaatttta     240
gttttagata tttacctata aggatataat aggaggtgtt caaagatgca tgtaactcaa     300
tgtagtatta attataattg taaaatagta ataacatttt ttgtcaaatc ataatgttag     360
gaaaattagt gatggcacat ttaaccaatt gaattatatt cagttctgaa taccgtgatg     420
catgttcaaa ttaattgata caaaaatcca acaactttag cagtttgttt accagttatt     480
gagtaccaac tgtgttcaac attgttattt cactcatatg aaatgataaa tgtatgtgcn     540
tgttatgata cggtcaataa aaccactttt                                       570
```

<210> SEQ ID NO 91
<211> LENGTH: 520
<212> TYPE: DNA
<213> ORGANISM: Homo sapiens

<400> SEQUENCE: 91

```
gtgagattgg ctatgtccag atcctagctt ttgtatttac tagttgcatg aacttgtgca       60
gtctggcctt cagtgcatat acctgtaaca taagctgcat agacatgtct gttttatagg     120
gttagtgaaa ttatccaaat ggcgattatc caaatcacga tggtgattta tggaaagaca     180
tcacaggcaa agtatacaag tttcttaaa gaagttaaca agaactgaac tgggtagaaa      240
tggttgtaca aagccagaag cttttccacat tattcctatt agaggagcaa atatcccatg     300
ccattcaagt atgtcaaatg tgccctagca tttattggac cattaggttt ttcttggtgt     360
ttctttatca ttcttctgtg atgtcttaaa ccctttggt ttgttttaat atttatgtat      420
ttcttaagag gtacatgtaa ctggtaggcg cactgccaac acattactga attttctca      480 aggttaccat accaagtgta ctatccttta gcaggccaaa                             520
```

<210> SEQ ID NO 92
<211> LENGTH: 428
<212> TYPE: DNA
<213> ORGANISM: Homo sapiens
<220> FEATURE:
<221> NAME/KEY: modified_base
<222> LOCATION: (130)..(130)
<223> OTHER INFORMATION: a, c, t, g, unknown or other
<220> FEATURE:
<221> NAME/KEY: misc_feature

```
<222> LOCATION: (130)..(130)
<223> OTHER INFORMATION: n is a, c, g, or t
<220> FEATURE:
<221> NAME/KEY: modified_base
<222> LOCATION: (241)..(241)
<223> OTHER INFORMATION: a, c, t, g, unknown or other
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: modified_base
<222> LOCATION: (243)..(243)
<223> OTHER INFORMATION: a, c, t, g, unknown or other
<220> FEATURE:
<221> NAME/KEY: misc_feature
<222> LOCATION: (243)..(243)
<223> OTHER INFORMATION: n is a, c, g, or t

<400> SEQUENCE: 92
ggctggtttg cagtgttgtg atcatggctc acagcagcct cagtttctca aactcagaag     60
attctctcat ttcagcctct caggtagctg ggttacaagt gtgtagcatc acacctagct    120
agttttttn gtatttatgg ttgagacagt tttgccgcgt tgccaaggct ggtctcaaac    180
ttctgagatc cagtgatcag cccatcttaa cctctcaaag tcctgagatt atatttttt    240
ntnttaagta gtttaattta tatttaaaat tatttattaa aaatgaagtt actacttta    300
ttgtgattgt tttatgtgtt cctcagtggt atttttata tgttggttta ttgccttaaa    360
tttcatttta attgtgtagt gatgtgcttc aattatttt tatatcttgt tttgcatagt    420
ttctataa                                                             428

<210> SEQ ID NO 93
<211> LENGTH: 485
<212> TYPE: DNA
<213> ORGANISM: Homo sapiens

<400> SEQUENCE: 93
gcaaattata acgaccagta ctatttttt ttggaattga aaacccaaga agccctaaaa     60
taagaacagt gagatcaaag gctggtttct aaaacaatgc agaaaataga accatgttgg    120
aattcctaaa ttctagcttt caaatactac tgtttccaac agtgaatcct tgacagagac    180
tgaatgcaga tggaattttg aaacattttc agtagctacc tcctctcctg aaattcctat    240
aagtggcaga ggaaaatcca atcctttaa tataacatgt ccatctcatg actcctgctt    300
acacacattt gtgttgattt gcttcatttc tggaggatgg gaatttgcag agctggtgac    360
atttccttca ttagacacca gaaattcacc agagagagac agatctgtgc cttctctttt    420
taggatctgg ttattgatac tttaataaat gtggtgtaaa gaaaatccat ggctacagtc    480
tgtat                                                                485

<210> SEQ ID NO 94
<211> LENGTH: 475
<212> TYPE: DNA
<213> ORGANISM: Homo sapiens
<220> FEATURE:
<221> NAME/KEY: modified_base
<222> LOCATION: (206)..(206)
<223> OTHER INFORMATION: a, c, t, g, unknown or other
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: modified_base
<222> LOCATION: (267)..(267)
```

<223> OTHER INFORMATION: a, c, t, g, unknown or other
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: misc_feature
<222> LOCATION: (342)..(342)
<223> OTHER INFORMATION: n is a, c, g, or t

<400> SEQUENCE: 94

```
taaaacttta cctgtgacaa ggaataaatt catgattaga agaattatac tgttttttctt      60 gtgcaaataa tacttaaggc agatgttcag tctcacagtg atgttggaaa gcatattta      120 tgcagtctaa acactatttc tgtattagat atttaaatgc atgaggataa attctaattg     180 cttttttgttt aaaacagaaa catagnagaa gcattagccc cagtttgtat aaaatgtctg    240
ctgcaactga attcatgata gttcatnaaa actgaaaatc attccaattt tgtaaaactg    300
ctgctactgg ttttatcaat aaagtttttag cagatggctt anaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aactcaaggg gcaacccaat gcccattata acaaa         475
```

<210> SEQ ID NO 95
<211> LENGTH: 507
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: misc_feature
<222> LOCATION: (32)..(32)
<223> OTHER INFORMATION: n is a, c, g, or t

<400> SEQUENCE: 95

```
agacatatga atccaggctg actgcnttaa gntgcccatc tcgtttgata taaactgtag      60
aaaaggcaag cactttgttc tgagtctttt atctccaaat acatagttgt ctcaaaccaa    120
gcaagcttta tcaaaatggc ttatttgcag aatagttcca atgatataaa tgccaactgg    180
caagtcattc caaactgctt gaaggagtag atgaaccaga atctgagaat ttggaaatag    240
gtcacagaaa aagcctccat ttggctaaat atgacaatta tctgagtatg gttaaataca    300
tacaattaaa tgtctgaagc caatgagttg tttattctaa cttgaaatat attttttgtga   360 gaataaatgt tagaaaagtt agtttatttt ggaaacctgc cgtgaaagga aattctaaag   420
gcttaacatg aaactgtctg catttctacc tgttagacaa tggttgctct tgggctcttg   480
ttatacagtc atatggctac acgttta                                        507
```

<210> SEQ ID NO 96
<211> LENGTH: 440
<212> TYPE: DNA
<213> ORGANISM: Homo sapiens

<400> SEQUENCE: 96

```
aagcgagaac gctttcatta cttgccagag caaaactgct atggttttaa actcaacaca      60
cacattattc acatcctatt ggtatactgg tatgttgact tgggaatacg tcaggtttac     120
acggcagttc agaatagtaa atatttggaa gtttacaaac tcttgcttcc ttaaaggtca     180
gaacatcagg ccaaagtaca acgtttaatt tcagaacttg ccttccaatt tacgcatttt    240
caatttgctc tccccatttg ttgagtcaga agaagcagca ttgcccagaa acaggtatta    300
cgtaacatgc acatactcta aaaagtactc atcccttgtt ttctgctcat tcttccagc     360
ctgaggaaca gacgtcagaa aaaaagcaac cacccagaca acttcccctt ttagctgagc    420
tgtcttctga ccaatcaaca                                                440
```

<210> SEQ ID NO 97
<211> LENGTH: 350
<212> TYPE: DNA
<213> ORGANISM: Homo sapiens
<220> FEATURE:
<221> NAME/KEY: modified_base
<222> LOCATION: (251)..(251)
<223> OTHER INFORMATION: a, c, t, g, unknown or other
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: modified_base
<222> LOCATION: (253)..(253)
<223> OTHER INFORMATION: a, c, t, g, unknown or other
<220> FEATURE:
<221> NAME/KEY: misc_feature
<222> LOCATION: (253)..(254)
<223> OTHER INFORMATION: n is a, c, g, or t
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: modified_base
<222> LOCATION: (284)..(284)
<223> OTHER INFORMATION: a, c, t, g, unknown or other
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: modified_base
<222> LOCATION: (292)..(292)
<223> OTHER INFORMATION: a, c, t, g, unknown or other
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: misc_feature
<222> LOCATION: (303)..(303)

```
<223> OTHER INFORMATION: n is a, c, g, or t
<220> FEATURE:
<221> NAME/KEY: modified_base
<222> LOCATION: (305)..(306)
<223> OTHER INFORMATION: a, c, t, g, unknown or other
<220> FEATURE:
<221> NAME/KEY: misc_feature
<222> LOCATION: (305)..(306)
<223> OTHER INFORMATION: n is a, c, g, or t
<220> FEATURE:
<221> NAME/KEY: modified_base
<222> LOCATION: (308)..(309)
<223> OTHER INFORMATION: a, c, t, g, unknown or other
<220> FEATURE:
<221> NAME/KEY: misc_feature
<222> LOCATION: (308)..(309)
<223> OTHER INFORMATION: n is a, c, g, or t

<400> SEQUENCE: 97
caccatgcct aactatcgtt gctactttct attggaagag aaggcagccc tgatttagtc    60
tgtttacagt ctgcattatg tggagaatag agagccatca tagtccctaa aactttcctt   120
gccagttaac ccagcaggac aacctgtctt tgtctcttga caactgttaa ctgagaacag   180
ggcccttgct cctctaggtg tgcacattaa ggactttgca cagtgtggat gtagctcatg   240
ctgctctgcc ntnnagtaca tgctgcttga attttcatca tnancctcca cnccttncac   300
ctncnngnna aaaaaaagc gtgcaggaag tagcatttca gatccttctc              350

<210> SEQ ID NO 98
<211> LENGTH: 136
<212> TYPE: DNA
<213> ORGANISM: Homo sapiens
<220> FEATURE:
<221> NAME/KEY: modified_base
<222> LOCATION: (68)..(69)
<223> OTHER INFORMATION: a, c, t, g, unknown or other
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: misc_feature
<222> LOCATION: (91)..(91)
<223> OTHER INFORMATION: n is a, c, g, or t

<400> SEQUENCE: 98
gccccaaggt ctttaagtat ctctgtcact tattagctca ccagagaaga cacaggaatg    60
agaggccnnt tgtttgtccc gagtgtcaaa naaggcttct tccagatatc agacctacgg   120
gtgcatcaga taattc                                                  136

<210> SEQ ID NO 99
<211> LENGTH: 494
<212> TYPE: DNA
<213> ORGANISM: Homo sapiens
<220> FEATURE:
<221> NAME/KEY: modified_base
<222> LOCATION: (101)..(101)
<223> OTHER INFORMATION: a, c, t, g, unknown or other
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: modified_base
<222> LOCATION: (110)..(110)
<223> OTHER INFORMATION: a, c, t, g, unknown or other
```

```
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: modified_base
<222> LOCATION: (367)..(367)
<223> OTHER INFORMATION: a, c, t, g, unknown or other
<220> FEATURE:
<221> NAME/KEY: misc_feature
<222> LOCATION: (367)..(367)
<223> OTHER INFORMATION: n is a, c, g, or t

<400> SEQUENCE: 99
tgaacttgtt ttatatttgc atatcaagag tcaagtatga tgttttttta agttgactt       60 ttttacttca ttatttttag gaataaatgt aagattttac naatcttttn atttccccac    120
aagatctgaa gtttggtatt tttgcattat gacagttgtt gagactagga ttttaagcta    180
ggatatgatt atatttccta tataactaaa aattttgttt cataaatttt aaaataatta    240
tttttgacta tgaacattag tccaaattta atatttgaca cagttcatac cagcttgcta    300
caataatgat aatttattag tctttctgtt atttaaagaa taaaacatg cttataaaag     360 acttttnaat gaaatgttgc ctttttaaaa taattatact tgcacatgaa aataaaatat    420
aaagtcaata atagtccttg tagcccaatg ggaattgatt ctgtttattg tctgtaccat    480
tttgctacca gtta                                                       494

<210> SEQ ID NO 100
<211> LENGTH: 548
<212> TYPE: DNA
<213> ORGANISM: Homo sapiens

<400> SEQUENCE: 100
gaacgaaagc atttaactgg ccagttttga ttgcaaatgc tgtaaagata tagaatgaag     60
tcctgtgagg ccttcctatc tccaagtcta tgtattttct ggagaccaaa ccagatacca    120
gataatcaca aagaaagctt ttttaataag gcttaaacca agaccttgtc tagatatttt    180
tagtttgttg ccaaggtagc actgtgagaa atctcacttg gatgttatgt aagggtgag    240 acacaacagt ctgactatga gtgaggaaaa tatctgggtc ttttcgtcag tttggtgcat    300
ttgctgctgc tgttgctact gtttgcctca aacgctgtgt ttaaacaacg ttaaactctt    360
agcctacaag gtggctctta tgtacatagt tgttaataca tccaattaat gatgtctgac    420
atgctatttt tgtagggaga aaatatgtgc taatgatatt tgagttaaa atatctttg     480 gggaggattt gctgaaaagt tgcactttg ttacaatgct tatgcttggt acaagcttat     540
gctgtctt                                                              548

<210> SEQ ID NO 101
<211> LENGTH: 504
<212> TYPE: DNA
<213> ORGANISM: Homo sapiens

<400> SEQUENCE: 101
tggtttattg ccgtgtgcta tgcctttgtg ttctcagctc tgattgagtt tgccacagta     60
aactatttca ctaagagagg ttatgcatgg gatggcaaaa gtgtggttcc agaaaagcca    120
aagaaagtaa aggatcctct tattaagaaa acaacacttt acgctccaac agcaaccagc    180
tacaccccta atttggccag gggcgacccg ggcttagcca ccattgctaa aagtgcaacc    240
atagaaccta aagaggtcaa gcccgaaaca aaaccaccag aacccaagaa aacctttaac    300
```

```
agtgtcagca aaattgaccg actgtcaaga atagccttcc cgctgctatt tggaatctttt    360 aacttagtct actgggctac gtatttaaac agagagcctc agctaaaagc ccccacacca    420
catcaataga tcttttactc acattctgtt gttcagttcc tctgcactgg gaatttattt    480
atgttctcaa cgcagtaatt ccca                                           504
```

<210> SEQ ID NO 102
<211> LENGTH: 517
<212> TYPE: DNA
<213> ORGANISM: Homo sapiens

<400> SEQUENCE: 102

```
aacagattca tgcttgtatc ttgcattcag aaaacaaact gtcctactaa tcaaagctgc     60
atatctcatc agagataatg gttgaatttt attgcaacca tattggcaat ctgaaactgg    120
caaacacaaa ggattgtttt cactaggctt accatttttgc tttgcttttt taacacactg   180
agccaaagat gcagtgtaat tattgggctt ttgccttatg ttgagttcag gtaagcatg    240 gaagctagtg attctgaatg atatatatat ccattgcatg ttgaactcct ttagaatttt    300
gttcttaaac aaacttagaa tttcaaaaga aaacatatga tccattaagt tgggagtgttt   360 atgattattg ctagaaagaa ggcagacttc atattctcat cgcccatttt tcaaacttgt    420
tacattgatc tgtacattat tttaagccac atgtttgtaa ttgttttaaaa caaagtggaa   480 acattacaca atgtccttaa taaataggcc catgtaa                             517
```

<210> SEQ ID NO 103
<211> LENGTH: 369
<212> TYPE: DNA
<213> ORGANISM: Homo sapiens
<220> FEATURE:
<221> NAME/KEY: modified_base
<222> LOCATION: (323)..(331)
<223> OTHER INFORMATION: a, c, t, g, unknown or other
<220> FEATURE:
<221> NAME/KEY: misc_feature
<222> LOCATION: (323)..(331)
<223> OTHER INFORMATION: n is a, c, g, or t

<400> SEQUENCE: 103

```
tgctcagaat ccacaagtca cggtctaaac acacttagaa tactacagca taaatctgtt     60
agcattattg ccaaataaga cagttgggat ccaaacccaa gtcttgagca atgttttttct   120 caaaaagctg ctatccaatg atataggaaa atacattgtg ttttcctaaa cacacttttc    180
tttttaaatg tgcttcattg tttgatttgg tcctgcctaa atttcacaag ctaggccaat    240
gaaggctgaa tcaaagacat ttcatccacc aatatcatgt gtagatatta tgtatagaaa    300
ataaaataaa ttatggctct aannnnnnnn ntgctggtta tcttggttat tttcggcgtt    360
atactaatg                                                             369
```

<210> SEQ ID NO 104
<211> LENGTH: 562
<212> TYPE: DNA
<213> ORGANISM: Homo sapiens

<400> SEQUENCE: 104

```
gagctctatc ttcatgtact catcctgaat ccttattttt ctaaaatagc acccttgtt     60 aattatttttt atggaaatta ttactctgtc ataattaaat catagctagt ataactttac   120
agataaccta aaaagaatag aaaagaagag agagtggctt tgtcagtata aaaccatgta    180
aagtcatcat caagtcatct ggatgaatct tgaaacacat ttagctgcca gttttacaaa    240
```

```
cctttaatat atcagtgctc cagtatataa cctcaaacaa atgtaaatag aacgaattat    300
tttcttgttt tgaattgtca atatattaaa tgttgactct ttgggagagt tgttggcaag    360
tttcaatggt gagaaacatt attgtcaact tgaaatgtgt tctgtaatgg ggacactaca    420
aaaagctagc tttccaatgt gtgcatagta ttggcaatat gaatatatat tatatataat    480
ctaatactta ttataagctg ctccctgtct atgtatttgg aaacctttc acaaagggaa     540 ttgcctaaca tgtggacttt ta                                             562

<210> SEQ ID NO 105
<211> LENGTH: 20
<212> TYPE: DNA
<213> ORGANISM: Artificial Sequence
<220> FEATURE:
<223> OTHER INFORMATION: Foward RT-PCR primer for human GAPDH

<400> SEQUENCE: 105
tggaaatccc atcaccatct                                                 20

<210> SEQ ID NO 106
<211> LENGTH: 20
<212> TYPE: DNA
<213> ORGANISM: Artificial Sequence
<220> FEATURE:
<223> OTHER INFORMATION: Reverse RT-PCR primer for human GAPDH

<400> SEQUENCE: 106
gtcttctggg tggcagtgat                                                 20

<210> SEQ ID NO 107
<211> LENGTH: 21
<212> TYPE: DNA
<213> ORGANISM: Artificial Sequence
<220> FEATURE:
<223> OTHER INFORMATION: Forward RT-PCR primer for human CDH26

<400> SEQUENCE: 107 tgcttttct gttgcgatgc t                                                21

<210> SEQ ID NO 108
<211> LENGTH: 19
<212> TYPE: DNA
<213> ORGANISM: Artificial Sequence
<220> FEATURE:
<223> OTHER INFORMATION: Reverse RT-PCR primer for CDH26

<400> SEQUENCE: 108
cttgccataa ccccagctc                                                  19

<210> SEQ ID NO 109
<211> LENGTH: 19
<212> TYPE: DNA
<213> ORGANISM: Artificial Sequence
<220> FEATURE:
<223> OTHER INFORMATION: Forward RT-PCR primer for human IL-4

<400> SEQUENCE: 109
acatctttgc tgcctccaa                                                  19

<210> SEQ ID NO 110
<211> LENGTH: 19
<212> TYPE: DNA
<213> ORGANISM: Artificial Sequence
<220> FEATURE:
```

<223> OTHER INFORMATION: Reverse RT-PCR primer for IL-4

<400> SEQUENCE: 110
aggcagcgag tgtccttct                                                  19

<210> SEQ ID NO 111
<211> LENGTH: 25
<212> TYPE: DNA
<213> ORGANISM: Artificial Sequence
<220> FEATURE:
<223> OTHER INFORMATION: RT-PCR primer for human IL-5

<400> SEQUENCE: 111
gcttctgcat ttgagtttgc tagct                                           25

<210> SEQ ID NO 112
<211> LENGTH: 27
<212> TYPE: DNA
<213> ORGANISM: Artificial Sequence
<220> FEATURE:
<223> OTHER INFORMATION: Reverse RT-PCR primer for human IL-5

<400> SEQUENCE: 112
tggccgtcaa tgtatttctt tattaag                                         27

<210> SEQ ID NO 113
<211> LENGTH: 20
<212> TYPE: DNA
<213> ORGANISM: Artificial Sequence
<220> FEATURE:
<223> OTHER INFORMATION: Forward RT-PCR primer for human IL-13

<400> SEQUENCE: 113
acagccctca gggagctcat                                                 20

<210> SEQ ID NO 114
<211> LENGTH: 22
<212> TYPE: DNA
<213> ORGANISM: Artificial Sequence
<220> FEATURE:
<223> OTHER INFORMATION: Reverse RT-PCR primer for human IL-13

<400> SEQUENCE: 114
tcaggttgat gctccatacc at                                              22

<210> SEQ ID NO 115
<211> LENGTH: 23
<212> TYPE: DNA
<213> ORGANISM: Artificial Sequence
<220> FEATURE:
<223> OTHER INFORMATION: Forward RT-PCR primer for human IFN-gamma

<400> SEQUENCE: 115
gttttgggtt ctcttggctg tta                                             23

<210> SEQ ID NO 116
<211> LENGTH: 26
<212> TYPE: DNA
<213> ORGANISM: Artificial Sequence
<220> FEATURE:
<223> OTHER INFORMATION: Reverse RT-PCR primer for human IFN-gamma

<400> SEQUENCE: 116
aaaagagttc cattatccgc tacatc                                          26

-continued

```
<210> SEQ ID NO 117
<211> LENGTH: 22
<212> TYPE: DNA
<213> ORGANISM: Artificial Sequence
<220> FEATURE:
<223> OTHER INFORMATION: Forward RT-PCR primer for human TNF-alpha

<400> SEQUENCE: 117
ccccagggac ctctctctaa tc                                              22

<210> SEQ ID NO 118
<211> LENGTH: 23
<212> TYPE: DNA
<213> ORGANISM: Artificial Sequence
<220> FEATURE:
<223> OTHER INFORMATION: Reverse RT-PCR primer for human TNF-alpha

<400> SEQUENCE: 118
ggtttgctac aacatgggct aca                                             23

<210> SEQ ID NO 119
<211> LENGTH: 20
<212> TYPE: DNA
<213> ORGANISM: Artificial Sequence
<220> FEATURE:
<223> OTHER INFORMATION: Forward RT-PCR primer for human  IL-17A

<400> SEQUENCE: 119
aatctccacc gcaatgagga                                                 20

<210> SEQ ID NO 120
<211> LENGTH: 19
<212> TYPE: DNA
<213> ORGANISM: Artificial Sequence
<220> FEATURE:
<223> OTHER INFORMATION: Reverse RT-PCR primer for human IL-17A

<400> SEQUENCE: 120
acgttcccat cagcgttga                                                  19

<210> SEQ ID NO 121
<211> LENGTH: 23
<212> TYPE: DNA
<213> ORGANISM: Artificial Sequence
<220> FEATURE:
<223> OTHER INFORMATION: Forward RT-PCR primer for human IL-17F

<400> SEQUENCE: 121
tgccaggagg tagtatgaag ctt                                             23

<210> SEQ ID NO 122
<211> LENGTH: 22
<212> TYPE: DNA
<213> ORGANISM: Artificial Sequence
<220> FEATURE:
<223> OTHER INFORMATION: Reverse RT-PCR primer for human IL-17F

<400> SEQUENCE: 122
atgcagccca agttcctaca ct                                              22

<210> SEQ ID NO 123
<211> LENGTH: 20
<212> TYPE: DNA
<213> ORGANISM: Artificial Sequence
<220> FEATURE:
<223> OTHER INFORMATION: Forward RT-PCR primer for human IL-25
```

<400> SEQUENCE: 123
tgaagtgctg tctggagcag                                          20

<210> SEQ ID NO 124
<211> LENGTH: 20
<212> TYPE: DNA
<213> ORGANISM: Artificial Sequence
<220> FEATURE:
<223> OTHER INFORMATION: Reverse RT-PCR primer for human IL-25

<400> SEQUENCE: 124
tcctcagaat catccatgtc                                          20

<210> SEQ ID NO 125
<211> LENGTH: 20
<212> TYPE: DNA
<213> ORGANISM: Artificial Sequence
<220> FEATURE:
<223> OTHER INFORMATION: Forward RT-PCR primer for human IL-33

<400> SEQUENCE: 125
cacccctcaa atgaatcagg                                          20

<210> SEQ ID NO 126
<211> LENGTH: 20
<212> TYPE: DNA
<213> ORGANISM: Artificial Sequence
<220> FEATURE:
<223> OTHER INFORMATION: Reverse RT-PCR primer for human IL-33

<400> SEQUENCE: 126
ggagctccac agagtgttcc                                          20

<210> SEQ ID NO 127
<211> LENGTH: 31
<212> TYPE: DNA
<213> ORGANISM: Artificial Sequence
<220> FEATURE:
<223> OTHER INFORMATION: Primer containing EcoRI site to generate
      expression construct

<400> SEQUENCE: 127
ggaattcacc atggccatga gatccgggag g                             31

<210> SEQ ID NO 128
<211> LENGTH: 36
<212> TYPE: DNA
<213> ORGANISM: Artificial Sequence
<220> FEATURE:
<223> OTHER INFORMATION: primer containing NotI site to generate
      expression construct

<400> SEQUENCE: 128
ataagaatgc ggccgcttag gaaggaacac ctgact                        36

<210> SEQ ID NO 129
<211> LENGTH: 58
<212> TYPE: DNA
<213> ORGANISM: Artificial Sequence
<220> FEATURE:
<223> OTHER INFORMATION: primer containing KpnI site to generate
      expresson construct

<400> SEQUENCE: 129
ggggtacctt acaggtcctc ctcgctgatc agcttctgct cggaaggaac acctgact    58

<210> SEQ ID NO 130
<211> LENGTH: 55
<212> TYPE: DNA
<213> ORGANISM: Artificial Sequence
<220> FEATURE:
<223> OTHER INFORMATION: primer containing KpnI site to generate expressoin construct

<400> SEQUENCE: 130
ggggtacctt aggcgtagtc gggcacgtcg tagggggtagg aaggaacacc tgact        55

<210> SEQ ID NO 131
<211> LENGTH: 33
<212> TYPE: DNA
<213> ORGANISM: Artificial Sequence
<220> FEATURE:
<223> OTHER INFORMATION: primer containing XbaI site to generate expression construct

<400> SEQUENCE: 131
gctctagaca ccatggctac tcaagctgat ttg        33

<210> SEQ ID NO 132
<211> LENGTH: 28
<212> TYPE: DNA
<213> ORGANISM: Artificial Sequence
<220> FEATURE:
<223> OTHER INFORMATION: primer containing KpnI site to generate expression construct

<400> SEQUENCE: 132
ggggtacctt acaggtcagt atcaaacc        28

<210> SEQ ID NO 133
<211> LENGTH: 30
<212> TYPE: DNA
<213> ORGANISM: Artificial Sequence
<220> FEATURE:
<223> OTHER INFORMATION: pirmer containing EcoRI site to generate expression construct

<400> SEQUENCE: 133
ggaattcacc atgactgctg tccatgcagg        30

<210> SEQ ID NO 134
<211> LENGTH: 60
<212> TYPE: DNA
<213> ORGANISM: Artificial Sequence
<220> FEATURE:
<223> OTHER INFORMATION: primer containing XbaI site to generate expression construct

<400> SEQUENCE: 134
gctctagaca ccatgtaccc ctacgacgtg cccgactacg ccgctactca agctgatttg        60

<210> SEQ ID NO 135
<211> LENGTH: 55
<212> TYPE: DNA
<213> ORGANISM: Artificial Sequence
<220> FEATURE:
<223> OTHER INFORMATION: primer containing  KpnI site to generate expression construct

<400> SEQUENCE: 135
ggggtacctt aggcgtagtc gggcacgtcg taggggtaca ggtcagtatc aaacc        55

-continued

```
<210> SEQ ID NO 136
<211> LENGTH: 57
<212> TYPE: DNA
<213> ORGANISM: Artificial Sequence
<220> FEATURE:
<223> OTHER INFORMATION: primer containing KpnI site to generate
      expression construct

<400> SEQUENCE: 136
ggggtacctt aggcgtagtc gggcacgtcg tagggggtaga tgctgtccat agctttg      57

<210> SEQ ID NO 137
<211> LENGTH: 29
<212> TYPE: DNA
<213> ORGANISM: Artificial Sequence
<220> FEATURE:
<223> OTHER INFORMATION: primer continuing EcoRI site to generate
      expression construct

<400> SEQUENCE: 137
ggaattcacc atggacgact cagaggtgg                                      29

<210> SEQ ID NO 138
<211> LENGTH: 28
<212> TYPE: DNA
<213> ORGANISM: Artificial Sequence
<220> FEATURE:
<223> OTHER INFORMATION: primer containing KpnI site to generate
      expression construct

<400> SEQUENCE: 138
ggggtaccct aaatcttctg catggagg                                       28

<210> SEQ ID NO 139
<211> LENGTH: 31
<212> TYPE: PRT
<213> ORGANISM: Artificial Sequence
<220> FEATURE:
<223> OTHER INFORMATION: Amino acid residues 832-862 of human E-cadherin

<400> SEQUENCE: 139

Val Phe Asp Tyr Glu Gly Ser Gly Ser Glu Ala Ala Ser Leu Ser Ser
1               5                   10                  15

Leu Asn Ser Ser Glu Ser Asp Lys Asp Gln Asp Tyr Asp Tyr Leu
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Amino acid residues 783 - 814 of CDH26

<400> SEQUENCE: 140

Val Tyr Ser Glu Glu Gly Glu Cys Gly Gly Ala Pro Ser Leu Ser Ser
1               5                   10                  15

Leu Ala Ser Leu Glu Gln Glu Leu Gln Pro Asp Leu Leu Asp Ser Leu
            20                  25                  30

<210> SEQ ID NO 141
<211> LENGTH: 383
<212> TYPE: DNA
<213> ORGANISM: Artificial Sequence
<220> FEATURE:
<223> OTHER INFORMATION: CDH26 3' UTR sequence with poly(A) signal at 5'

<400> SEQUENCE: 141
```

-continued

```
aaaaaaaagt ctattttgga gaattgaaat aattcatgga agggaatcac tattcaggga        60
tttttcccct ttgctcttct tttccctcct taaaagaaaa attaccttct agtcctagga       120
tgaggacaca ctattagttt gaattaaatg ctttgatatt ctcagatcag ccatcttgaa       180
ccaaagcaaa accacaagtt acactttctt aaaatttgat ttgtcatatt ttctagagaa       240
acttgaattt aattgtgtta ttcttagctt ccactggcag cctagctttg agggtaaatg       300
aaaatataac ccatagatta cccagccact tgggaacagc aggtaatact gaagaaaaat       360
aaaaatagat tttgaaaacg tta                                              383
```